US008883995B2

(12) United States Patent
tenOever

(10) Patent No.: US 8,883,995 B2
(45) Date of Patent: Nov. 11, 2014

(54) LIVE ATTENUATED INFLUENZA VIRUS VACCINES COMPRISING MICRORNA RESPONSE ELEMENTS

(75) Inventor: Benjamin tenOever, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 71 days.

(21) Appl. No.: 13/255,040

(22) PCT Filed: Mar. 8, 2010

(86) PCT No.: PCT/US2010/000709
§ 371 (c)(1),
(2), (4) Date: Feb. 23, 2012

(87) PCT Pub. No.: WO2010/101663
PCT Pub. Date: Sep. 10, 2010

(65) Prior Publication Data
US 2012/0148622 A1 Jun. 14, 2012

Related U.S. Application Data

(60) Provisional application No. 61/158,233, filed on Mar. 6, 2009.

(51) Int. Cl.
C07H 21/04 (2006.01)
C12N 15/113 (2010.01)
C12N 7/00 (2006.01)
A61K 39/145 (2006.01)
A61K 39/00 (2006.01)

(52) U.S. Cl.
CPC .......... A61K 39/145 (2013.01); C12N 15/1131 (2013.01); C12N 2310/113 (2013.01); C12N 2320/30 (2013.01); C12N 7/00 (2013.01); C12N 2310/141 (2013.01); C12N 2760/16134 (2013.01); C12N 2760/16361 (2013.01); C12N 2760/16161 (2013.01); C12N 2760/16261 (2013.01); C12N 2760/16334 (2013.01); A61K 2039/5254 (2013.01); C12N 2760/16234 (2013.01)
USPC ...................................................... 536/24.5

(58) Field of Classification Search
USPC ...................................................... 536/24.5
See application file for complete search history.

(56) References Cited

U.S. PATENT DOCUMENTS

| 2004/0152112 | A1 | 8/2004 | Croce et al. | |
|---|---|---|---|---|
| 2005/0075492 | A1 | 4/2005 | Chen et al. | |
| 2007/0026403 | A1* | 2/2007 | Hatzigeorgiou et al. | 435/6 |
| 2007/0054872 | A1* | 3/2007 | Reppen et al. | 514/44 |
| 2007/0213293 | A1 | 9/2007 | McSwiggen et al. | |
| 2007/0253978 | A1 | 11/2007 | Niman | |
| 2008/0045472 | A1 | 2/2008 | Brahmachari et al. | |
| 2008/0076116 | A1 | 3/2008 | Pekosz et al. | |
| 2008/0118531 | A1 | 5/2008 | Hoffmann et al. | |
| 2008/0201801 | A1 | 8/2008 | Allen et al. | |
| 2009/0203136 | A1* | 8/2009 | Baltimore et al. | 435/375 |
| 2010/0173312 | A1* | 7/2010 | Slack et al. | 435/6 |

FOREIGN PATENT DOCUMENTS

WO   WO2009/111892 A1 * 9/2009

OTHER PUBLICATIONS

Kruger et al. Nucleic Acid Research 2006 vol. 34, W451-W454.*
Barnes, et al., Harnessing Endogenous miRNAs to Control Virus Tissue Tropism as a Strategy for Developing Attenuated Virus Vaccines, Cell Host & Microbe, vol. 4, pp. 239-248, 2008.
Brown, et al., Endogenous microRNA regulation suppresses transgene expression in hematopoietic lineages and enables stable gene transfer, Nature Medicine, vol. 12, No. 5, pp. 585-591, 2006.
Burnside, et al., Deep Sequencing of Chicken microRNAs, BMC Genomics, vol. 9:185, 2008.
Glazov et al., Origin, Evolution, and Biological Role of miRNA Cluster in DLK-DIO3 Genomic Region in Placental Mammals, Mol Biol Evol, vol. 25(5), pp. 939-948, 2008.
Hoffmann, et al., Modulation of influenza virus replication by alteration of sodium ion transport and protein kinase C activity, Antiviral Research, vol. 80, pp. 124-134, 2008.
Hsu et al., ViTa—Virus mRNA Target, XP002683988, Retrieved from the Internet URL: http://vita.mbc.nctu.edu.tw/search_target.php?hh=0&mirna=hsa-mir-16&mfe=-12&score=120&target=influenza+A&choice=score&B4= [retrieved on Sep. 24, 2012].
Hsu et al., ViTa: prediction of host microRNAs targets on viruses, Nucleic Acids Research, vol. 35, Database issue, pp. D381-D385, 2007.
International Preliminary Report on Patentability for International Patent Application No. PCT/US10/00709, dated Sep. 6, 2011.
International Search Report for International Patent Application No. PCT/US10/00709, dated Aug. 30, 2010.
Kelly, et al., Engineering microRNA responsiveness to decrease virus pathogenicity, Nature Medicine, vol. 14, No. 11, pp. 1278-1283, 2008.
Landgraf, et al., A Mammalian microRNA Expression Atlas Based on Small RNA Library Sequencing, Cell, vol. 129, pp. 1401-1414, 2007.
Makeyev, et al., The MicroRNA miR-124 Promotes Neuronal Differentiation by Triggering Brain-Specific Alternative Pre-mRNA Splicing, Molecular Cell, vol. 27, pp. 435-448, 2007.
Muramoto, et al., Hierarchy among Viral RNA (vRNA) Segments in Their Role in vRNA Incorporation into Influenza A Virions, J. Virol., vol. 80, No. 5, pp. 2318-2325, 2006.

(Continued)

Primary Examiner — Brian Whiteman
(74) Attorney, Agent, or Firm — Fish & Richardson P.C.

(57) ABSTRACT

The invention is directed to novel live attenuated influenza virus (LAIV) vaccines comprising one or more microRNA (miRNA) Response Element(s) (MRE) within an influenza virus genome. The MREs useful for the present invention can be derived from any miRNA which is highly expressed in influenza-targeted cells of an animal in need of vaccination but are not expressed or are expressed at very low levels in species (e.g., embryonated chicken eggs) or cell lines used for a large-scale vaccine production. This allows efficient vaccine production but renders the vaccine virus susceptible to attenuation in the influenza-targeted cells of vaccinated animals expressing a cognate miRNA.

65 Claims, 19 Drawing Sheets

(56) References Cited

OTHER PUBLICATIONS

Park, et al., Engineered viral vaccine constructs with dual specificity: Avian influenza and Newcastle disease, Proc Natl Acad Sci U.S.A., vol. 103, No. 21, pp. 8203-8208, 2006.

Perez, et al., Influenza A virus-generated small RNAs regulate the switch from transcription to replication, Proc Natl Acad Sci U.S.A., vol. 107, No. 25, pp. 11525-11530, 2010.

Perez, et al., MicroRNA-mediated species-specific attenuation of influenza A virus, Nature Biotechnology, vol. 27, No. 6, pp. 572-578, 2009.

Pleschka, et al., A plasmid-based reverse genetics system for influenza A virus, J. Virol., vol. 70 No. 6, pp. 4188-4192, 1996.

Quinlivan, et al., Attenuation of Equine Influenza Viruses through Truncations of the NS1 Protein, J. Virol., vol. 79, No. 13, pp. 8431-8439, 2005.

Shapiro, et al., Noncanonical cytoplasmic processing of viral microRNAs, RNA, vol. 16, pp. 2068-2074, 2010.

Sivasubramanian et al., Sequence analysis of the polymerase 1 gene and the secondary structure prediction of polymerase 1 protein of human influenza virus A/WSN/33, J. Virol., vol. 44, No. 1, pp. 321-329, 1982.

Song et al., Cellular MicroRNAs Inhibit Replication of the H1N1 Influenza A Virus in Infected Cells, J. Virol., vol. 84, No. 17, pp. 8849-8860, 2010.

Subbarao et al., Characterization of an Avian Influenza A (H5N1) Virus Isolated from a Child with a Fatal Respiratory Illness, Science, vol. 279, No. 5349, pp. 393-396, 1998.

Supplementary European Search Report and Communication pursuant to Rules 70(2) and 70a(2) for European Patent Application No. 10749069, dated Oct. 15, 2012.

tenOever et al., Multiple Functions of the IKK-Related Kinase IKKξ in Interferon-Mediated Antiviral Immunity, Science, vol. 315, pp. 1274-1278, 2007.

Treanor, et al., Safety and Immunogenicity of an Inactivated Subvirion Influenza A (H5N1) Vaccine, N Engl J Med, vol. 354, No. 13, pp. 1343-1351, 2006.

Tumpey et al., Characterization of the Reconstructed 1918 Spanish Influenza Pandemic Virus, Science, vol. 310, pp. 77-80, 2005.

Varble, et al., Engineered RNA viral synthesis of microRNAs, Proc Natl Acad Sci U.S.A., vol. 107, No. 25, pp. 11519-11524, 2010.

Office Action in Japanese Application No. 2011-552950, mailed Jul. 29, 2014, 13 pages (with English translation).

'Vita' [online], "Virus-targeted by miRNAs:hsa-miR-16," [retrieved from the internet on Jul. 29, 2014],Retrieved from the Internet: http://vita.mbcnctu.edu.tw/search_target.php?hh=0&mirna=hsa-mir-16&mfe=-12&score=120&target=influenza+A&choice=score&B4=, 4 pages.

'Vita' [online], "Virus-targeted by miRNAs-hsa-miR-93," [retrieved from the Internet on Jul. 29, 2014]. Retrieved from the Internet: http://vita.mbc.nctu.edu.tw/search_target.php?hh=0&mirna=hsa-mir-93&mfe=-12&score=120&target=influenza+A&choice=score&B4=, 4 pages.

GenBank Accession No. J02178.1, dated Jun. 2006, 2 pages.

Guan et al., "H5N1 influenza: a protean pandemic threat," Proc Natl Acad Sci U S A. May 25, 2004;101(21):8156-61.

* cited by examiner

| | | Site 1 | Site 2 |
|---|---|---|---|
| PRNTL1/2 | Passage 0 | ACCUAGAGAGGAUGGUCCUAUCU | UUUCUAGCCAGAACUGCACUCUUA |
| PRNTL1/2 | Passage 1 | ACCUAGAGAGGAUGGUCCUAUCU | UUUCUAGCCAGAACUGCACUCUUA |
| PRNTL1/2 | Passage 10 | ACCUAGAGAGGAUGGUCCUAUCU | UUUCUAGCCAGAACUGCACUCUUA |
| 93NP2 | Passage 0 | | UUCCUUGCACGGACAGCACUUUUA |
| 93NP2 | Passage 1 | | UUCCUUGCACGGACAGCACUUUUA |
| 93NP2 | Passage 10 | | UUCCUUGCACGGACAGCACUUUUA |
| 93NP1/2 | Passage 0 | ACACUUGAACGAAUGGUACUUUCU | UUCCUUGCACGGACAGCACUUUUA |
| 93NP1/2 | Passage 1 | ACACUUGAACGAAUGGUACUUUCU | UUCCUUGCACGGACAGCACUUUUA |
| 93NP1/2 | Passage 10 | ACACUUGAACGAAUGGUACUUUCU | UUCCUUGCACGGACAGCACUUUUA | ex vivo

| | | | |
|---|---|---|---|
| 93NP2 | Day 5 | | UUCCUUGCACGGACAGCACUUUUA |
| 93NP1/2 | Day 5 | ACACUUGAACGAAUGGUACUUUCU | UUCCUUGCACGGACAGCACUUUUA | in vivo

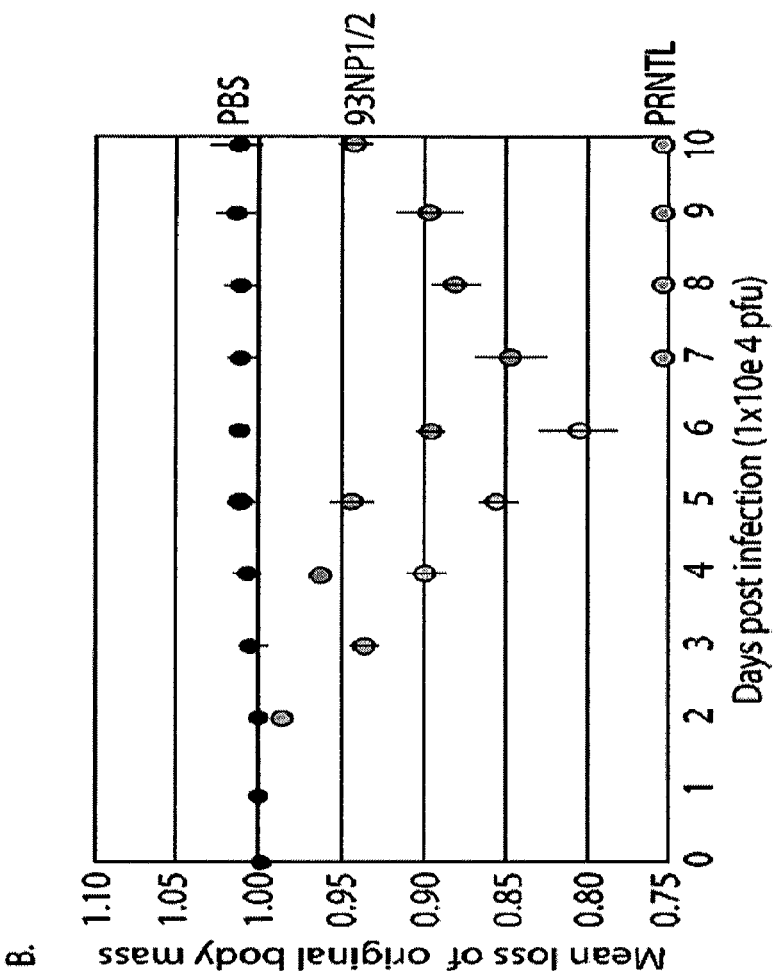
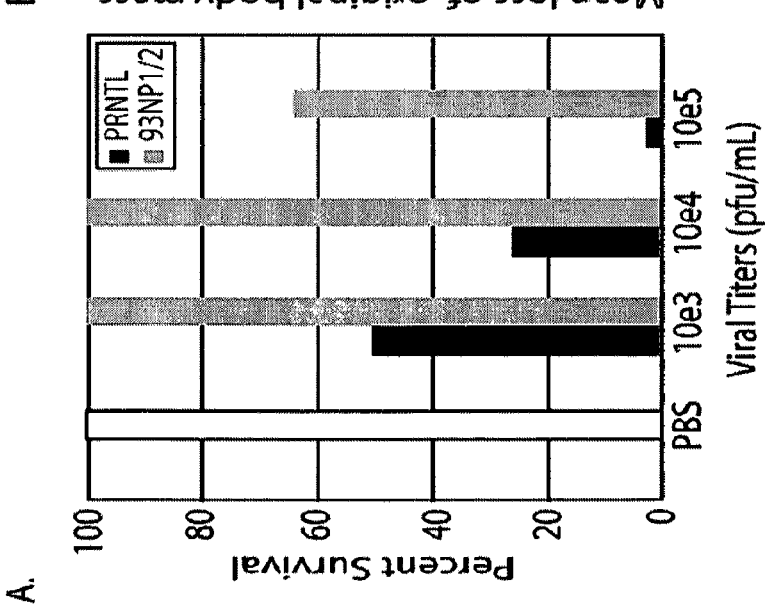
Figure 4B
Figure 4A

LIVE ATTENUATED INFLUENZA VIRUS VACCINES COMPRISING MICRORNA RESPONSE ELEMENTS

CROSS REFERENCE TO PRIOR APPLICATIONS

This is a U.S. National Phase application under 35 U.S.C. §371 of International Patent Application No. PCT/US2010/000709, filed Mar. 8, 2010, and claims the priority of U.S. Provisional Patent Application No. 61/158,233, filed Mar. 6, 2009, both of which are incorporated by reference herein. The International Application published in English on Sep. 10, 2010 as WO 2010/101663A2 under PCT Article 21(2).

GOVERNMENT SPONSORED RESEARCH OR DEVELOPMENT

This invention was made with government support under award number W911NF-08-1-0413, awarded by the Department of Defense. The government has certain rights in the invention.

REFERENCE TO SEQUENCE LISTING

Pursuant to 37 C.F.R. 1.821(c), an electronic version of the substitute sequence listing has been submitted as an ASCII compliant text file named "SubstituteSequenceListing2.txt" that was created on Feb. 5, 2014, and has a size of 31,696 bytes. The content of this file is incorporated herein by reference in its entirety.

TECHNICAL FIELD OF THE INVENTION

The present invention is directed, generally, to prevention of influenza virus infections, in particular, to prevention of infections by seasonal strains of influenza virus and those with pandemic potential. More specifically, disclosed herein are novel live attenuated influenza virus (LAIV) vaccines comprising one or more microRNA Response Element(s) (MRE).

BACKGROUND OF THE INVENTION

Influenza virus infection in humans is a respiratory disease that ranges in severity from subclinical infection to primary viral pneumonia that can result in death. Influenza-associated complications include, among others, Reye's syndrome, myocarditis, pericarditis, myositis, encephalopathy and transverse myelitis. The persistence and unfettered nature of influenza virus leads to yearly epidemics as well as sporadic pandemics with potential to cause catastrophic loss of life. Palese et al., Nature Medicine 8(9):927 (2002). Seasonal influenza is the seventh leading cause of death in the United States and the leading cause of death in children ages 1 to 4 years. Ninety percent of deaths in people 65 and older are the result of influenza virus infection with associated pneumonia. Every year in the United States, approximately 36,000 people die, 114,000 are hospitalized, and the country incurs more than $1 billion in direct economic costs.

Three types of influenza viruses (A, B, and C) are distinguishable by antigenic reactivities of their internal antigens. Influenza A, B and C belong to the family Orthomyxoviridae and have a segmented negative strand RNA genome that is replicated in the nucleus of the infected cell and consists of eight negative-sense RNA (nsRNA) gene segments that encode 10 polypeptides, including RNA-directed RNA polymerase proteins (PB2, PB1 and PA), nucleoprotein (NP), neuraminidase (NA), hemagglutinin (HA, which after enzymatic cleavage is made up of the association of subunits HA1 and HA2), the matrix proteins (M1 and M2) and the non-structural proteins (NS1 and NS2, also referred to as Nuclear Export Protein (NEP)). Krug et al., In The Influenza Viruses, R. M. Krug, ed., Plenum Press, New York, 1989, pp. 89-152. The HA and NA proteins embedded in the viral envelope are the primary antigenic determinants of the influenza virus (Air et al., Structure, Function, and Genetics, 1989, 6:341-356; Wharton et al., In The Influenza Viruses, R. M. Krug, ed., Plenum Press, New York, 1989, pp. 153-174). Due to the possible reassortment of the influenza virus' segmented genome (antigenic shift) and the accumulation of genomic polymorphisms (antigenic drift), new HA and NA variants are constantly created for which a newly infected organism has no anamnestic immune response. Such constant generation of new antigenic variants from a vast number of circulating strains creates enhanced danger of emergence of new highly pathogenic strains (such as, e.g., H5N1 and H1N1 influenza A virus transmitted directly from avian or swine species to humans) and creates the need for annual vaccination and development of antiviral agents that are effective against many or all strains. Palese, Nature Medicine 10(12 Suppl):S82 (2004); Garcia-Sastre and Biron, Science 312 (5775):879 (2006); Li et al., Nature 2004, 430:209; Kuiken et al., Science 2004, 306:241. This has forced the World Health Organization to monitor current strains and constantly update the composition of the annual vaccine. For the production of a safe and effective vaccine it is important that the selected vaccine strains are closely related to the circulating strains, thereby ensuring that the antibodies in the vaccinated population are able to neutralize the antigenetically similar virus.

Among the three types of influenza viruses, influenza A and B viruses cause significant morbidity and mortality in humans. Fields et al., Lippincott Williams & Wilkins, Philadelphia, Pa., 2007. Thus, annual vaccines used to combat influenza virus infection include a combination of two influenza A strains with a single influenza B strain. Palese, Nature Medicine 10(12 Suppl):582 (2004).

Propagation of these viral strains is usually performed in embryonated chicken eggs, where the virus can grow to very high titers. The virus particles generated in eggs are subsequently purified and used as stocks for vaccine preparations. Recently, mammalian cell culture systems for large-scale influenza vaccine production have been also established. Reviewed in, e.g., Genzel and Reichl, Expert Review of Vaccines, 2009, 8(12):1681-1692. Currently, vaccines produced in three different mammalian cell lines (Madin-Darby Canine Kidney [MDCK], Vero and PER.C6) are in clinical trials.

Recently developed reverse-genetics systems have allowed the manipulation of the influenza viral genome (Palese et al., Proc. Natl. Acad. Sci. USA 1996, 93:11354; Neumann and Kawaoka, Adv. Virus Res. 1999, 53:265; Neumann et al., Proc. Natl. Acad. Sci. USA 1999, 96:9345; Fodor et al., J. Virol. 1999, 73:9679; U.S. Patent Publication No. 20040029251). For example, it has been demonstrated that the plasmid-driven expression of eight influenza vRNAs from a pol I promoter and all mRNAs from a pol II promoter result in the formation of infectious influenza A virus (Hoffmann et al., Proc. Natl. Acad. Sci. USA 2000, 97:6108; Hoffmann et al., Vaccine 2002, 20:3165; U.S. Pat. No. 6,951,754).

The influenza vaccines currently licensed by public health authorities for use in the United States and Europe are inactivated influenza vaccines as well as the live attenuated FLU-MIST vaccine in the United States.

Inactivated vaccines are produced by chemical inactivation of the virus grown either in cell culture or in embryonated chicken eggs. Chemical inactivation is usually followed by detergent-mediated fragmentation. Typical inactivation/fragmentation treatments involve such agents as formalin+Triton, formaldehyde, beta-propiolactone, ether, ether+Tween-80, cetyl trimethyl ammonium bromide (CTAB)+Triton N101, sodium deoxycholate and tri(n-butyl) phosphate. Nicholson, Webster and May (eds.), Textbook of Influenza, Chapters 23, 24, 27, pp. 317-332 and 358-372. For the virus produced in eggs, inactivation can occur after or prior to clarification of allantoic fluid. Although inactivation dramatically increases the safety of the vaccine, it reduces vaccine potency. Also, vaccine testing to ensure loss of replicative activity is time-consuming and labor-intensive, which increases vaccine cost and decreases the usefulness of the vaccine during rapidly spreading seasonal infections and pandemics.

Current vaccine strategies focus on live attenuated influenza virus (LAIV) strains through the development of temperature-sensitive mutants or the removal of pathogenic factors such as the NS1 protein. Talon, J. et al., Proc. Natl. Acad. Sci. USA, 97:4309-4314 (2000); Nichol, Vaccine, 19:4373-4377 (2001); Palese et al., J. Infect. Dis., 1997, 176 Suppl 1:S45-9. For example, FLUMIST (Influenza Virus Vaccine Live, Intranasal) contains influenza virus strains which are (a) cold-adapted (i.e., they replicate efficiently at 25° C., a temperature that is restrictive for replication of many wild-type influenza viruses); (b) temperature-sensitive (i.e., they are restricted in replication at 37° C. (Type B strains) or 39° C. (Type A strains), temperatures at which many wild-type influenza viruses grow efficiently); and (c) attenuated (they do not produce classic influenza-like illness in the ferret model of human influenza infection).

As compared to traditional inactivated vaccines, LAIV vaccines are well suited for mucosal (e.g., intranasal) administration and generate a more robust immune response by inducing local, mucosal, cell-mediated and humoral immunity. Treanor et al., New England J. Med. 354(13):1343 (2006) Still, current LAIV vaccines are too attenuated to stimulate a strong immune response in elderly people, the major group of the 20,000-40,000 individuals in the US dying each year as a result of influenza infection. Most importantly, present LAIV vaccines are subject to replicative impairment in embryonated chicken eggs because they have been adapted to growth at suboptimal temperatures required for proper egg development, thereby limiting the subsequent scale of vaccine production. Such impediment on global scale production must be overcome should a highly pathogenic pandemic strain emerge. Li et al., Nature 430(6996):209 (2004) and Krug, Science 311(5767):1562 (2006).

Thus, there is a great need in the art for new influenza vaccines that are safe, efficient for generating protective immunity and are amenable to rapid large-scale production in chicken eggs and/or cell culture. In particular, there is a great need in the art for new more efficient LAIV vaccines.

SUMMARY OF THE INVENTION

The present invention addresses these and other needs in the art by providing novel live attenuated influenza virus (LAIV) vaccines comprising one or more species-specific and/or tissue/cell-specific microRNA (miRNA) Response Element(s) (MRE). Tissue/cell- and species-specific MREs useful in LAIV vaccines of the present invention bind, and are post-transcriptionally inhibited by, miRNAs which are expressed at high levels in a particular cell or tissue type targeted by the influenza virus in an animal to be vaccinated (including, e.g., epithelial, secretory [Clara], ciliated, apical, goblet [mucous], hematopoietic [e.g., dendritic cells, macrophages, lymphocytes], bronchial, and other cells of the lung and upper respiratory tract targeted by the influenza virus) and/or miRNAs which are expressed at high levels in a select species to be vaccinated (e.g., human, mouse, canine, chicken), but are not expressed or are expressed at very low levels in a cell line or species (e.g., embryonated chicken eggs [*Gallus gallus*]) used for a large-scale vaccine production. While MRE insertion in coding regions of the influenza genome is preferred as it increases vaccine safety by preventing emergence of escape mutants, the present invention also encompasses the incorporation of MREs in other parts of influenza genome and in artificially generated influenza virus 3' UTRs. The MRE-based live attenuated vaccine strategy of the present invention provides the versatility, safety, and efficacy required for rapid generation of large quantities of vaccines for newly emerging seasonal and pandemic influenza strains.

In a more general aspect, the present invention is applicable to any virus amenable to recombinant production. By insertion of species- and/or tissue/cell-specific MREs into the viral genome, the present invention allows generation of recombinant viruses which can be used as live attenuated vaccines and can be efficiently propagated in another species or cell line derived from tissues/cells not targeted by these viruses.

Specifically, in the first aspect, the present invention provides a composition comprising a recombinant influenza virus wherein said influenza virus contains one or more MRE sequences. In a preferred embodiment, the influenza virus contains two or more MRE sequences. Such two or more MREs can have identical sequences, can differ in several nucleotide positions while maintaining the same MRE seed sequence (i.e., 5' positions 1-7 or 2-8 of the miRNA sequence), or can even correspond to two or more different miRNAs.

In a preferred embodiment, such one or more MRE sequences are inserted within a coding region of one or more influenza virus genes. Such one or more MREs can be inserted regardless of a reading frame so long as the number of amino acid changes is kept to a minimum to preserve the viral protein function. An MRE can be inserted into a coding region of any influenza virus protein, including HA, NA, PB1, PB2, PA, M1, M2, NP, NS1, and NEP. Preferably, an MRE is inserted into a coding region of an influenza virus protein which is conserved between different influenza strains such as, for example, PB1, PB2, PA, M1, M2, NP, NS1, and NEP.

In another specific embodiment, MRE sequence is inserted in an artificially generated influenza virus 3' UTR.

In a specific embodiment, the MRE inserted in an influenza virus genome corresponds to a miRNA which is expressed in a species-specific and/or tissue/cell-specific manner. In one embodiment, the MRE inserted in an influenza virus genome corresponds to a miRNA which is highly expressed in mammalian cells but is not expressed or is expressed at very low levels in the regions where influenza viral propagation occurs within embryonated chicken eggs. In a specific embodiment, the MRE corresponds to miRNA selected from the group consisting of miR-16, miR-17, miR-19, miR-25, miR-34, miR-92, and miR-93. For example, such MRE can correspond to miRNA selected from the group consisting of miR-16 having sequence 5'-UAGCAGCACGUAAAUAUUG-GCG-3' (SEQ ID NO: 1), miR-17 having sequence 5'-CAAAGUGCUUACAGUGCAGGUAG-3' (SEQ ID NO: 2), miR-19 having sequence 5'-UGUGCAAAUCUAUG-CAAAACUGA-3' (SEQ ID NO: 3), miR-25 having sequence 5'-CAUUGCACUUGUCUCGGUCUGA-3' (SEQ ID NO: 4), miR-34 having sequence 5'-UGGCAGUGUCU-UAGCUGGUUGU-3' (SEQ ID NO: 5), miR-92 having sequence 5'-UAUUGCACUUGUCCCGGCCUG-3' (SEQ ID NO: 6), and miR-93 having sequence 5'-CAAAGUGCU-GUUCGUGCAGGUAG-3' (SEQ ID NO: 7).

In another embodiment, the MRE inserted in an influenza virus genome corresponds to a miRNA which is highly expressed in tissues targeted by the influenza virus in an animal to be vaccinated but is not expressed or is expressed at very low levels in the cell lines used for influenza virus propagation and large-scale production. In a specific embodiment, the MRE corresponds to miRNA selected from the group consisting of miR-142, miR-222, miR-149, miR-1977, miR-181b-2, miR-1259, and miR-1978. For example, such MRE can correspond to miRNA selected from the group consisting of miR-142 having sequence 5'-UGUAGUGU-UUCCUACUUUAUGGA-3' (SEQ ID NO: 141), miR-222 having sequence 5'-AGCUACAUCUGGCUACUGGU-3' (SEQ ID NO: 142), miR-149 having sequence 5'-UCUG-GUCCGUGUCUUCACUCCC-3' (SEQ ID NO: 143), miR-1977 having sequence 5'-GAUUAGGGUGCUUAGCUG-UUAA-3' (SEQ ID NO: 144), miR-181b-2 having sequence 5'-AACAUUCAUUGCUGUCGGUGGGU-3' (SEQ ID NO: 145), miR-1259 having sequence 5'-AUAUAUGAUGACU-UAGCUUUU-3' (SEQ ID NO: 146), and miR-1978 having sequence 5'-GGUUUGGUCCUAGCCUUUCUA-3' (SEQ ID NO: 147).

In a specific embodiment, the recombinant attenuated influenza virus of the invention is derived from an influenza subtype selected from the group consisting of H5N1, H1N1, H2N2, and H3N2. In one embodiment, the recombinant attenuated influenza virus of the invention is derived from an isolate selected from the group consisting of A/Vietnam/1203/04, A/chicken/Scotland/59, A/duck/Hong Kong/308/78, A/PuertoRico/8/1934, A/NewYork/616/1995, A/California/04/2009, A/HongKong/16/68, A/USSR/039/68, A/Yokohama/C5/85, A/Leningrad/134/17/57, A/Leningrad/134/47/57, and A/Ann Arbor/6/60.

In conjunction with the virus-containing compositions, the present invention also provides recombinant nucleic acids which can be used for production of MRE-containing influenza viruses. Thus, in a separate embodiment, the invention provides an isolated nucleic acid molecule comprising an influenza virus sequence containing one or more MRE sequence(s) inserted within said sequence. In a specific embodiment, the nucleic acid of the invention is such that the mean free energy (MFE) of MRE interaction with its corresponding miRNA is less than −20 kcal/mol. In another embodiment, the nucleic acid of the invention is such that the mean free energy (MFE) of MRE interaction with its corresponding miRNA is less than −35 kcal/mol. Further provided herein are the following specific non-limiting examples of the nucleic acid molecules of the invention:

1. A nucleic acid molecule which comprises two MREs which correspond to miR-93 and are inserted into the coding sequence of influenza virus protein NP, wherein the first MRE sequence is at the nucleotide sequence encoding NP amino acids 62-69 and the second MRE sequence is at the nucleotide sequence encoding NP amino acids 258-265. For example, the first MRE sequence can comprise the nucleotide sequence 5'-ACAATTGAACGAATGGTACTTTCT-3' (SEQ ID NO: 107) and the second MRE sequence can comprise the nucleotide sequence 5'-TTCCTTGCACGGTCAGCACTTATA-3' (SEQ ID NO: 111).

2. A nucleic acid molecule which comprises two MREs which correspond to miR-92 and are inserted into the coding sequence of influenza virus protein NS1, wherein the first MRE sequence is at the nucleotide sequence encoding NS1 amino acids 131-137 and the second MRE sequence is at the nucleotide sequence encoding NS1 amino acids 150-156. For example, the first MRE sequence can comprise the nucleotide sequence 5'-AAGGCCAACTTCAGTGTAATA-3' (SEQ ID NO: 97) and the second MRE sequence can comprise the nucleotide sequence 5'-TTCACCGAGGAAGGTGCAATA-3' (SEQ ID NO: 101).

3. A nucleic acid molecule which comprises three MREs which correspond to miR-92 and are inserted into the coding sequence of influenza virus protein HA, wherein the first MRE sequence is at the nucleotide sequence encoding HA amino acids 68-74, the second MRE sequence is at the nucleotide sequence encoding HA amino acids 195-201, and the third MRE sequence is at the nucleotide sequence encoding HA amino acids 526-532. For example, the first MRE sequence can comprise the nucleotide sequence 5'-CTA-CAGTTGGGGAAGTGCAAT-3' (SEQ ID NO: 83), the second MRE sequence can comprise the nucleotide sequence 5'-AACGCCTATGTAAGTGTAGTA-3' (SEQ ID NO: 87), and the third MRE sequence can comprise the nucleotide sequence 5'-TTGGTCAGTTTAGGTGCAATA-3' (SEQ ID NO: 91).

4. The nucleic acid molecule which comprises three MREs which correspond to miR-19 and are inserted into the coding sequence of influenza virus protein HA, wherein the first MRE sequence is at the nucleotide sequence encoding HA amino acids 15-22, the second MRE sequence is at the nucleotide sequence encoding HA amino acids 561-568, and the third MRE sequence is at the nucleotide sequence encoding HA amino acids 327-334. For example, the first MRE sequence can comprise the nucleotide sequence 5'-GCCAGT-GCTGACACAATTTGCATA-3' (SEQ ID NO: 45), the second MRE sequence can comprise the nucleotide sequence 5'-TCTTTGCAGTGCAGGATTTGCATA-3' (SEQ ID NO: 49), and the third MRE sequence can comprise the nucleotide sequence 5'-TTGCGUATGGTCACAGGTTTGCGC-3' (SEQ ID NO: 53).

5. The nucleic acid molecule which comprises two MREs which correspond to miR-16 and are inserted into the coding sequence of influenza virus protein HA, wherein the first MRE sequence is at the nucleotide sequence encoding HA amino acids 2-9 and the second MRE sequence is at the nucleotide sequence encoding HA amino acids 439-445. For example, the first MRE sequence can comprise the nucleotide sequence 5'-AAGGCCAACCTATTAGTGCTGCTA-3' (SEQ ID NO: 21) and the second MRE sequence can comprise the nucleotide sequence 5'-AACGCCGAACTATT-AGTGCTGCTA-3' (SEQ ID NO: 25).

6. The nucleic acid molecule which comprises three MREs which correspond to miR-34 and are inserted into the coding sequence of influenza virus protein PA, wherein the first MRE sequence is at the nucleotide sequence encoding PA amino acids 426-433, the second MRE sequence is at the nucleotide sequence encoding PA amino acids 634-641, and the third MRE sequence is at the nucleotide sequence encoding PA amino acids 709-716. For example, the first MRE sequence can comprise the nucleotide sequence 5'-GATGAGATCG-GTGAAGACGTTGCC-3' (SEQ ID NO: 69), the second MRE sequence can comprise the nucleotide sequence 5'-GGCAAGGTATGTAGGACACTGTTA-3' (SEQ ID NO: 73), and the third MRE sequence can comprise the nucleotide sequence 5'-TTCTTCCTGACTCATGCACTGTCA-3' (SEQ ID NO: 77).

7. The nucleic acid molecule which comprises two MREs which correspond to miR-25 and are inserted into the coding sequence of influenza virus protein M1, wherein the first MRE sequence is at the nucleotide sequence encoding M1 amino acids 111-118 and the second MRE sequence is at the nucleotide sequence encoding M1 amino acids 127-134. For example, the first MRE sequence can comprise the nucleotide sequence 5'-GGTGCCAAAGAGATAAGTGCAAGT-3' (SEQ ID NO: 59) and the second MRE sequence can comprise the nucleotide sequence 5'-ATATACAACAG-GATGGGTGCAGTG-3' (SEQ ID NO: 63).

8. The nucleic acid molecule which comprises three MREs which correspond to miR-17 and are inserted into the coding sequence of influenza virus protein PB 1, wherein the first MRE sequence is at the nucleotide sequence encoding PB1 amino acids 374-381, the second MRE sequence is at the nucleotide sequence encoding PB1 amino acids 418-424, and the third MRE sequence is at the nucleotide sequence encoding PB1 amino acids 677-683. For example, the first MRE sequence can comprise the nucleotide sequence 5'-GCCAG-CATTGATCTTAAGTACTTT-3' (SEQ ID NO: 31), the second MRE sequence can comprise the nucleotide sequence 5'-GTGTTGGGTGTAAGCATTTTG-3' (SEQ ID NO: 35), and the third MRE sequence can comprise the nucleotide sequence 5'-ACCAGCCAAAGAGGCGTTTTG-3' (SEQ ID NO: 39).

9. The nucleic acid molecule which comprises four MREs which correspond to miR-142 and are inserted into an artificial 3' UTR of influenza virus protein NP, wherein the MRE sequence is found between the viral stop codon and the polyA tail sequence. For example, the repetitive four MREs can comprise the nucleotide sequence 5'-TCCATAAAGTAG-GAAACACTACA-3' (SEQ ID NO: 159).

10. The nucleic acid molecule which comprises four MREs which correspond to miR-142 and are inserted into an artificial 3' UTR of influenza virus protein NS1, wherein the MRE sequence is found between the viral stop codon and the polyA tail sequence but before a duplicated NS2/NEP ORF. For example, the repetitive four MREs can comprise the nucleotide sequence 5'-TCCATAAAGTAGGAAACACTACA-3' (SEQ ID NO: 159).

Influenza nucleotide and amino acid positions provided in the above specific examples correspond to Influenza A virus strain A/Puerto Rico/8/34/Mount Sinai (H1N1). Specifically, these positions correspond to the following GenBank Accession Numbers:

| Influenza coding region | GenBank Accession No. for nucleotide sequence | GenBank Accession No. for protein sequence |
|---|---|---|
| NP | AF389119.1 | AAM75159.1 |
| NS1 | AF389122.1 | AAM75164.1 |
| HA | AF389118.1 | AAM75158.1 |
| PA | AF389117.1 | AAM75157.1 |
| M1 | AF389121.1 | AAM75161.1 |
| PB1 | AF389116.1 | AAM75156.1 |

In a specific embodiment, the recombinant viruses of the invention further comprise additional attenuating mutations. In one embodiment, such mutation results in a temperature-sensitive viral propagation (e.g., a mutation which is used in FLUMIST). In another embodiment, such mutation, is the removal of a pathogenic factor (e.g., removal of NS1 protein).

In a preferred embodiment, the composition of the invention is a vaccine composition. Such vaccine composition may further comprise an adjuvant.

In conjunction with the vaccine compositions, the present invention also provides a method of inducing a protective immune response to an influenza infection in an animal, said method comprising administering to said animal the MRE-containing recombinant influenza vaccine composition of the invention. In a preferred embodiment, the animal is human. In another embodiment, the animal is a bird (e.g., water fowl or chicken). In yet another embodiment, the animal is a pig. In a specific embodiment, the vaccine composition is administered mucosally. In another specific embodiment, the vaccine composition is administered conjointly with an adjuvant.

BRIEF DESCRIPTION OF THE FIGURES

FIGS. 8A-D. MRE-seeded influenza A viruses as live-attenuated vaccines. (A) Graphs showing average mean loss of original body weight for mice vaccinated intranasally with 10e3 PFU of PRNTL or MRE-seeded 93NP1/2 H1N1 viruses, and challenged 21 Days post infection (dpi) with 5×10e3 PFU of WT A/PR8/34. Data represents the mean of each cohort (n=4), errors bars are +/−SD. Right panel displays antibody response post challenge, as determined by lowest serum dilution to obtain positive hemagglutination inhibition and immunoglobulin response as measured by ELISA. (B) Table of segment disributions for the described H5N1 reassortant viruses. (C) Bar diagram showing viral titers from PRNTL and MRE-seeded H5N1 influenza A virus reassortant infections of 10-day old embryonated eggs. Titers determined by hemagglutination and plaque assay from allantoic fluid 2 days post infection and expressed as pfu/mL. Data are the means of four independent infections. (D) Same as in (A), with H5N1 reassortant PRNTL or MRE-seeded 93NP1/2 vaccinations.

DETAILED DESCRIPTION OF THE INVENTION

Figures 1A, 1B:
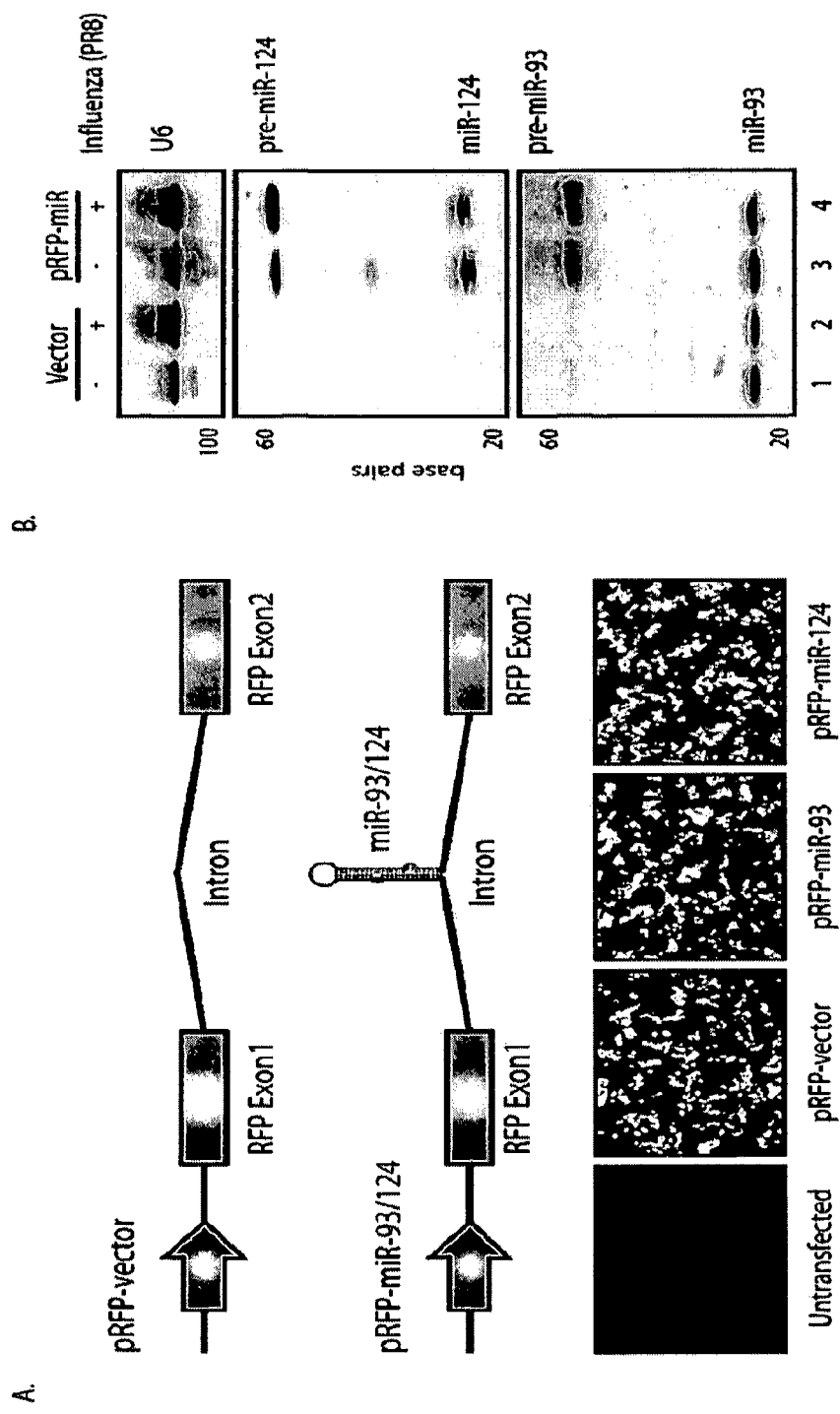
FIG. 1. (A) Top: Schematic of the red fluorescent protein (RFP) minigene containing a single intron (pRFP) used for the exogenous delivery of miRNAs (miR-93 or miR-124). Bottom: Fluorescence-microscopy of pRFP-transfected HEK-293 cells. (B) Northern blot of miR-93, miR-124, and U6 snRNA following mock or influenza virus infection of HEK-293 cells. (C) HEK-293 cells co-transfected with miR-124 and luciferase reporter constructs containing an SV40 or a miR-124 target 3' UTR. 6 hrs post-transfection, cells were infected with influenza virus (A/Puerto Rico/8/34 (H1N1)) at an MOI of 1.0 and luciferase activity was measured 18 hrs post-infection. (D) HEK-293 cells co-transfected with influenza virus NS1, miR-124, and luciferase reporter constructs containing the SV40 or a miR-124 target 3' UTR described in (C); luciferase activity was measured 24 hrs post-transfection. For (C) and (D), luciferase activity was normalized to a *Renilla* control vector. Data are the means of three independent transfections, each done in triplicate, error bars represent +/−SD. Western blots beneath each graph depict the expression of influenza matrix and NS1 proteins as measured by a polyclonal antibody to A/Puerto Rico/8/34 (H1N1).

The present invention is based on the unexpected discovery that effective and safe live attenuated viral vaccines can be generated that exploit a cell's microRNA (miRNA) processing machinery to induce viral attenuation in a species-specific and/or tissue/cell-specific manner. Specifically, the present invention provides novel live attenuated influenza virus (LAIV) vaccines comprising one or more miRNA Response Elements (MRE) inserted within a coding region and/or an artificial 3' UTR of one or more influenza virus genes.

miRNAs are small 19-25 base pair (bp) endogenous single stranded RNAs that regulate the expression of target mRNAs either by mRNA cleavage, translational repression/inhibition or heterochromatic silencing and thus affect global protein production. Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28. miRNAs regulate target mRNAs via a 7 bp "seed" sequence (i.e., sequence at 5' positions 1-7 or 2-8 of miRNA). Complementarity of an mRNA sequence to the "seed" is normally found in the 3' untranslated region (3' UTR). Bartel, Cell 116(2):281 (2004).

MREs corresponding to tissue-restricted miRNAs have been inserted into pre-existing untranslated regions (UTRs) of lentiviruses, picornoviruses, and rhabdoviruses to achieve tissue-specific viral attenuation. Brown et al., Nature Medicine 12(5):585 (2006); Barnes et al., Cell Host & Microbe 4(3):239 (2008); and Kelly et al., Nature Medicine 14(11): 1278 (2008).

Although these strategies lead to viral attenuation in particular tissues, their application for influenza vaccine production is hindered by the fact that influenza virus does not produce 3' UTRs that are of sufficient length for MRE insertion, where MREs are most effective, and any addition or change to the RNA ends of the influenza viral genomic segments results in replication and packaging defects. Muramoto et al., J. Virol. 80(5):2318 (2006). Furthermore, since untranslated sequences are subject to less selective pressure than protein coding sequences, as evident by the greater degree of evolutionary conservation in protein coding sequences, insertion of MREs into non-coding regions creates a high chance of emergence of "escape" mutants making such recombinant viruses unsafe for vaccine production.

The present invention constitutes a novel approach which overcomes the deficiencies of applying any previously described attenuation strategies for the generation of influenza A virus vaccines. This approach is based upon the incorporation of one or more species-specific and/or tissue/cell-specific MREs into strategic locations within the influenza virus genome (preferably, within viral protein coding sequences or within artificial 3' UTRs [generated, e.g., by the duplication of the viral packaging sequence and genetic insertion between the stop codon and the poly A tail]), which results in species-specific and/or tissue/cell-specific viral attenuation. By employing MREs corresponding to miRNAs that are highly expressed in cells and tissues targeted by influenza virus in an animal to be vaccinated but are not expressed or are expressed at very low levels in embryonated chicken eggs or cell lines used for large-scale vaccine production, high viral titers may be achieved during vaccine production with the retention of viral attenuation in cells expressing a cognate miRNA. Insertion of MREs within influenza coding regions prevents generation of escape mutants and thus increases vaccine safety.

The MREs useful for the present invention can be derived from any miRNA which is highly expressed in influenza-targeted cells (including, e.g., epithelial, secretory [Clara], ciliated, apical, goblet [mucous], bronchial, hematopoietic [e.g., dendritic cells, macrophages, lymphocytes], and other cells of the lung and upper respiratory tract targeted by the influenza virus) of an animal in need of vaccination (e.g., human) but are not expressed or are expressed at very low levels in species (e.g., embryonated chicken eggs [*Gallus gallus*]) or a cell line used for large-scale vaccine production.

Examples of useful human miRNAs include without limitation miR-16, miR-17, miR-19, miR-25, miR-34, miR-92, miR-93, miR-142, miR-222, miR-149, miR-1977, miR-181b-2, miR-1259, and miR-1978 such as miR-16 having sequence 5'-UAGCAGCACGUAAAUAUUGGCG-3' (SEQ ID NO: 1), miR-17 having sequence 5'-CAAAGUGCUUA-CAGUGCAGGUAG-3' (SEQ ID NO: 2), miR-19 having sequence 5'-UGUGCAAAUCUAUGCAAAACUGA-3' (SEQ ID NO: 3), miR-25 having sequence 5'-CAUUG-CACUUGUCUCGGUCUGA-3' (SEQ ID NO: 4), miR-34 having sequence 5'-UGGCAGUGUCUUAGCUGGUUGU-3' (SEQ ID NO: 5), miR-92 having sequence 5'-UAUUG-CACUUGUCCCGGCCUG-3' (SEQ ID NO: 6), and miR-93 having sequence 5'-CAAAGUGCUGUUCGUGCAG-GUAG-3' (SEQ ID NO: 7). miR-142 having sequence 5'-UGUAGUGUUUCCUACUUUAUGGA-3' (SEQ ID NO: 141), miR-222 having sequence 5'-AGCUACAUCUGGC-UACUGGU-3' (SEQ ID NO: 142), miR-149 having sequence 5'-UCUGGUCCGUGUCUUCACUCCC-3' (SEQ ID NO: 143), miR-1977 having sequence 5'-GAUUAGGGUGCU-UAGCUGUUAA-3' (SEQ ID NO: 144), miR-181b-2 having sequence 5'-AACAUUCAUUGCUGUCGGUGGGU-3' (SEQ ID NO: 145), miR-1259 having sequence 5'-AUAUAUGAUGACUUAGCUUUU-3' (SEQ ID NO: 146), and miR-1978 having sequence 5'-GGUUUGGUC-CUAGCCUUUCUA-3' (SEQ ID NO: 147). Additional useful miRNAs can be identified by parallel sequencing and determination of the relative expression levels between the two species or tissues/cells. See the current database of miRNA sequences (miRBase) on the WorldWideWeb at mirbase.org (miRBase) and Burside et al., BMC Genomics 9:185 (2008); Williams et al., BMC Genomics 8:172 (2007); Landgraf et al., Cell 129:1401 (2007).

In a preferred embodiment, at least two MREs are inserted in an influenza genomic segment. Such two or more MREs can have identical sequences, can differ in several nucleotide positions while maintaining the same MRE seed sequence (i.e., 5' positions 1-7 or 2-8 of the miRNA sequence), or can even correspond to two or more different miRNAs, wherein each miRNA is highly expressed in influenza-targeted cells of an animal in need of vaccination but are not expressed or are expressed at very low levels in the regions where viral propagation occurs within embryonated chicken eggs or a cell line used for large-scale vaccine production. Such two or more MREs can be inserted regardless of reading frame so long as the number of amino acid changes is kept to a minimum to preserve the viral protein function.

According to the present invention, the MRE(s) are preferably inserted within a protein coding region of an influenza virus gene. Insertion of MRE(s) within coding region(s) (as opposed to non-coding regions such as 5' or 3' untranslated regions (UTRs)) prevents generation of escape mutants and thus increases vaccine safety. While all influenza genes can be used for MRE insertion, it is preferable to use open reading frames of the influenza proteins which are more conserved, because it makes the emergence of escape mutants less likely and increases the safety of the vaccine. Thus, the preferred influenza genes for MRE insertion are PB1, PB2, PA, M1, M2, NP, NS1 and NEP.

The present invention also encompasses MRE insertions in other parts of influenza genome. In one specific embodiment, the invention provides MRE insertion in an artificial 3' UTR whereby MREs is inserted between the stop codon and the poly A tail sequence of the resulting viral mRNA. In one embodiment, such MRE insertion between the stop codon and the poly A tail sequence is accompanied by further adding sequences required for efficient viral strand packaging into the virion.

An MRE of the present invention is preferably 19-25 nucleotides long and contains a perfect complement of at least the "seed" sequence of the corresponding miRNA (i.e., 5' positions 1-7 or 2-8 of the miRNA sequence). Any additional complementarity can be used to further increase attenuation. Alternatively (or in addition), the attenuation may be enhanced by increasing the number of inserted MREs.

The MREs according to the invention can be designed, for example, by using partial or complete inverted and complementary sequence of the miRNA of interest whereby the miRNA can bind by standard Watson:Crick base pairing the nucleotides comprising the MRE. The use of shorter regions of complementarity increases the number of potential sites and reduces the number of needed nucleotide changes. Complementarity on the 3' end of the MRE (the seed sequence) should be maintained from position 1-7 or 2-8 at a minimum.

The live attenuated MRE-containing viruses of the invention can be produced recombinantly in cultured cells (e.g., in human embryonic kidney HEK-293 cells [ATCC Catalog No. CRL-1573], chicken fibroblasts DF1 [ATCC Catalog No. CRL-12203], Madin-Darby Canine Kidney (MCK) cells [ATCC Catalog Nos. CCL-34, CRL-2285, CRL-2286, CRL-2935, or CRL-2936], African green monkey kidney cells (Vero) [ATCC Catalog Nos. CCL-81, CRL-1586, CRL-1587, or CRL-2783], or human PER-C6 cells [Pau et al., Vaccine, 2001, 19(17-19):2716]) followed (if needed) by propagation in embryonated chicken eggs to obtain higher titers.

As disclosed in the Examples section, below, the H1N1- and H5N1-based attenuated influenza virus vaccines of the invention comprising two MREs corresponding to miR-93 inserted in NP open reading frame exhibit high stability (no revertants) when propagated in cell culture and produce protection from lethal dose of H1N1 and H5N1 respectively, when administered to mice.

Taken together, the novel MRE-based live attenuated vaccine strategy of the present invention provides the versatility, safety, and efficacy required for rapid generation of large quantities of vaccines for newly emerging influenza strains.

In a more general aspect, the present invention is applicable to any virus amenable to recombinant production. By insertion of species-specific and/or tissue/cell-specific MREs into viral genomes, the present invention allows generation of viruses which can be used as live attenuated vaccines in one species and/or tissue/cell and can be efficiently propagated in another species and/or tissue/cell.

DEFINITIONS

The term "influenza virus" is used herein to define a viral species of which pathogenic strains cause the disease known as influenza or flu. The term influenza is meant to include any strain or serotype of the influenza virus, including any combination of HA, e.g., H1, H2, H3, H4, H5, H6, H7, H8, H9, H10, H11, H12, H13, H14, H15, H16; and NA, e.g., N1, N2, N3, N4, N5, N6, N7, N8 or N9 genes. In one embodiment, influenza refers to H5N1 influenza (bird flu or pandemic influenza). In one embodiment, influenza refers to other strains or subtypes of the influenza virus, including but not limited to H1N1, H2N2, and H3N2.

In the context of influenza virus biology, "coding region" refers to areas of viral RNA which encode amino acids that are represented in the mature viral proteins.

The terms "microRNA" or "miRNA" as used herein refer to a small 19-25 bp endogenous single stranded RNA that regulates the expression of target mRNAs via a 7 bp "seed" sequence (i.e., sequence at 5' positions 1-7 or 2-8 of miRNA). Complementarity of an mRNA sequence to the "seed" is normally found in the 3' untranslated region (3' UTR). Bartel, Cell 116(2):281 (2004). miRNA regulation moderately affects global protein production resulting in a "fine tuning" of the cellular transcriptome. Baek et al., Nature 455(7209): 64 (2008) and Selbach et al., Nature 455(7209):58 (2008).

The term "complementarity" means that a nucleic acid can form hydrogen bond(s) with another nucleic acid sequence by either traditional Watson-Crick or other non-traditional types of interactions such as Wobble-base pairing which permits binding of guanine and uracil. A percent complementarity indicates the percentage of residues in a nucleic acid molecule that can form hydrogen bonds with a second nucleic acid sequence.

In reference to the nucleic acid molecules of the present invention, the binding free energy for a nucleic acid molecule with its complementary sequence is sufficient to allow the relevant function of the nucleic acid to proceed, e.g., miRNA activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J Am. Chem. Soc. 109:3783-3785). "Perfectly complementary" means that all the contiguous residues of a nucleic acid sequence will hydrogen bond with the same number of contiguous residues in a second nucleic acid sequence. In one embodiment, the human miRNA has partial complementarity (i.e., less than 100% complementarity) with the corresponding target influenza nucleic acid molecule.

The term "microRNA (miRNA) Response Element" or "MRE" is used herein to refer to a nucleotide sequence within an mRNA that can bind to a specific miRNA and result in a measurable amount of post-transcriptional silencing of such mRNA (determined, e.g., by a decrease in mRNA and/or protein content). For post-transcriptional silencing to occur, MRE-miRNA sequence complementarity should, at minimum, include the seed sequence of the miRNA with is comprised of nucleotides 1-7 or 2-8 and the 3' end of the MRE.

As specified herein, the species-specific and/or tissue/cell-specific MRE useful in the recombinant attenuated viruses of the invention can be derived from any miRNA which is highly expressed in influenza-targeted cells of an animal in need of vaccination but are not expressed or are expressed at very low levels in species (e.g., embryonated chicken eggs [*Gallus gallus*]) or cell lines used for large-scale vaccine production. Within the meaning of the present invention, "tissue/cell- and species-specific MREs" are defined as those MREs that bind, and are post-transcriptionally inhibited by, miRNAs which are expressed at high levels in a particular cell or tissue type targeted by the relevant virus in an animal to be vaccinated and/or miRNAs which are expressed at high levels in a select species to be vaccinated, but are not expressed or are expressed at very low levels in a cell line or species used for a large-scale vaccine production.

The terms "highly expressed" and "expressed at high levels" as used herein in conjunction with miRNA expression refer to miRNAs that are detectable by standard Northern blot analysis (Pall et al., Nature Protocols 3(6) 1077 (2008)). Preferably, such highly expressed miRNAs represent greater than or equal to 0.1% of the total cellular miRNA found in the tissue or cell of interest as measured by RNA deep sequencing (Hafner et al., Methods 44(1)₃ (2008)).

The term "expressed at very low levels" as used herein refers to those miRNAs that are undetectable by standard Northern blot analysis. Preferably, such miRNAs expressed at very low levels represent equal to or less than 0.01% of the total cellular miRNA found in the tissue or cell of interest as measured by RNA deep sequencing.

The terms "artificial 3'UTR" and "artificial 3' non-coding region (NCR)" as used herein in connection with recombinant attenuated influenza viruses refer to an insertion of a genetic element that is encoded in the mature RNA transcript but does not encode any protein information. "Artificial" refers to the fact that influenza viruses does not encode endogenous 3' UTRs capable of MRE insertion and therefore, the only means of utilizing this target location for MRE insertion is to generate a novel 3' UTR/NCR. Artificial 3' UTRs/NCRs in the recombinant attenuated influenza viruses of the present invention can be generated by the introduction of genetic material between the stop codon and the poly A tail. Furthermore, because all influenza viral segments have packaging information encoded within the 5' end of the vRNA (which overlaps with the genetic information encoding the stop codon and poly A tail), artificial 3' UTRs also demand the duplication of the 5' vRNA end. In this instance, the required material (usually 80 nt-200 nt depending on the segment), can be duplicated and inserted just beyond the poly A tail sequence.

As used herein, the term "infectious" refers to the ability of a virus to replicate in a cell and produce viral particles. Infectivity can be evaluated either by detecting virus, (i.e., viral load), or by observing disease progression in an animal.

An "individual" or "subject" or "animal", as used herein, refers to vertebrates that support a negative strand RNA virus infection, specifically influenza virus infection, including, but not limited to, birds (such as water fowl and chickens) and members of the mammalian species, such as canine, feline, lupine, mustela, rodent (racine, murine, etc.), equine, bovine, ovine, caprine, porcine species, and primates, the latter including humans. In a specific embodiment, the subject is a ferret, which is a good animal model for studying influenza. In another embodiment, the subject is a human.

As used herein, the term "immunogenic" means that an agent is capable of eliciting a humoral or cellular immune response, and preferably both. An immunogenic entity is also antigenic. An immunogenic composition is a composition that elicits a humoral or cellular immune response, or both, when administered to an animal having an immune system.

The term "vaccine" refers to a composition (e.g., a live attenuated influenza virus with or without an adjuvant) that can be used to elicit protective immunity in a recipient. It should be noted that to be effective, a vaccine of the invention can elicit immunity in a portion of the immunized population, as some individuals may fail to mount a robust or protective immune response, or, in some cases, any immune response. This inability may stem from the individual's genetic background or because of an immunodeficiency condition (either acquired or congenital) or immunosuppression (e.g., due to treatment with chemotherapy or use of immunosuppressive drugs). Vaccine efficacy can be established in animal models.

The term "adjuvant" refers to a compound or composition that augments the host's immune response to another antigen (e.g., live attenuated influenza virus) when administered conjointly with that antigen. Adjuvants useful in the vaccine compositions of the present invention include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, Bacille Calmette-Guerin (BCG), and *Corynebacterium parvum*. Preferably, the adjuvant is pharmaceutically acceptable.

Within the meaning of the present invention, the term "conjoint administration" is used to refer to administration of an immune adjuvant and an antigen simultaneously in one composition, or simultaneously in different compositions, or sequentially within a specified time period (e.g., 24 hours).

The term "protect" is used herein to mean prevent or treat, or both, as appropriate, development or continuance of a disease (e.g., flu) in a subject.

The terms "protective immune response" or "protective immunity" comprise a humoral (antibody) immunity or cellular immunity, or both, effective to, e.g., eliminate or reduce the load of a pathogen (e.g., influenza virus) or infected cell or produce any other measurable alleviation of the infection in an immunized (vaccinated) subject.

The term "therapeutically effective amount/dose" is used herein interchangeably with the term "immunogenically effective amount/dose" and refers to that quantity of a live attenuated influenza virus or a pharmaceutical composition or vaccine comprising such virus that is sufficient to produce a protective immune response upon administration to a mammal.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" applied to pharmaceutical or vaccine compositions of the invention refers to a diluent, excipient, or vehicle with which a compound (e.g., a live attenuated influenza virus) is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

As used herein, the term "isolated" means that the referenced material (e.g., a cell or virus) is removed from its native environment. Thus, an isolated biological material can be free of some or all cellular components, i.e., components of the cells in which the native material occurs naturally (e.g., cytoplasmic or membrane component). A material shall be deemed isolated if it is present in a cell extract or supernatant. In the case of nucleic acid molecules, an isolated nucleic acid includes, without limitation, a PCR product, an isolated RNA (e.g., mRNA or miRNA), a DNA (e.g., cDNA), or a restriction fragment. In another embodiment, an isolated nucleic acid is preferably excised from the cellular or viral genome in which it may be found, and, e.g., is no longer joined or proximal to other genes or regulatory sequences located upstream or downstream of this nucleic acid. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified virus is preferably substantially free of host cell or culture components, including tissue culture or egg proteins, non-specific pathogens, and the like. As used herein, the term "substantially free" is used operationally, in the context of analytical testing of the material. Preferably, purified material substantially free of contaminants is at least 50% pure; more preferably, at least 90% pure, and still more preferably at least 99% pure. Purity can be evaluated by chromatography, gel electrophoresis, immunoassay, composition analysis, biological assay, and other methods known in the art.

Methods for purification are well-known in the art. Viral particles can be purified by ultrafiltration through sucrose cushions or by ultracentrifugation, preferably continuous centrifugation (see Furminger, In: Nicholson, Webster and May (eds.), Textbook of Influenza, Chapter 24, pp. 324-332). Other purification methods are possible and contemplated herein. A purified material may contain less than about 50%, preferably less than about 75%, and most preferably less than about 90%, of the cellular components, media, proteins, or other undesirable components or impurities (as context requires), with which it was originally associated. The term "substantially pure" indicates the highest degree of purity which can be achieved using conventional purification techniques known in the art.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 428-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nuc. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

Selection of microRNA Response Elements (MREs) for Incorporation into the Viral Genome The present invention is exemplified by the incorporation of two ubiquitous MREs for miR-93 into the open reading frame (ORF) of the conserved influenza nucleocapsid (NP) protein to yield a highly attenuated influenza virus vaccine strain. As discussed below, the NP gene is characterized by little genetic drift between strains thus making the emergence of escape mutants unlikely. It will be understood, however, that MREs may be incorporated within coding or non-coding (e.g., artificial 3'UTRs) regions of other influenza mRNAs. While all influenza genes can be used for MRE insertion, it is preferable to use ORFs of the influenza proteins which are more conserved, because it makes the emergence of escape mutants less likely and increases the safety of the vaccine. Thus, the preferred influenza genes for MRE insertion are PB1, PB2, PA, M1, M2, NP, NS1 and NEP.

While one MRE may be sufficient for creating an effective LAIV vaccine, it is preferable to use at least two MREs to ensure an efficient attenuation in vaccinated animals and to decrease the possibility of escape mutants. Such two or more MREs can have an identical sequence or can differ in several nucleotide positions or can even correspond to two or more different miRNAs, wherein each miRNA is highly expressed in tissues/cells targeted by influenza viruses in animals to be vaccinated but is not expressed or is expressed at very low levels in species and/or tissues/cells used for large-scale vaccine production (e.g., regions where viral propagation occurs within embryonated chicken eggs [e.g., chorioallantoic membrane] or a suitable cell line [e.g., MDCK cells]). Such two or more MREs can be inserted into one or more positions in the influenza virus genome.

Incorporation of MRE sequences within the coding regions can be achieved by altering the coding region of an influenza virus gene with the goal of minimizing nucleotide sequence changes, in particular those nucleotide sequence changes that result in amino acid substitutions. Thus, the original identity of the amino acid is typically retained; however, if an amino acid substitution is required, it is preferred that it conform to the same hierarchical clustering (e.g., nonpolar (G, A, V, L, M, I); polar (S, T, C, P, N, E); aromatic (F, Y, W); positively charged (K, R, H); or negatively charged (D, E)).

Nucleotide changes can be introduced using any of the methods of site directed mutagenesis known in the art. See, e.g., Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 428-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nuc. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

For efficient attenuation, MRE sequence needs to be perfectly complementary to at least the miRNA "seed" sequence (i.e., miRNA 5' and MRE 3' nucleotides 1-7 or 2-8). Any additional complementarity helps further enhance viral attenuation. The MREs according to the invention can be designed, e.g., by using partial or complete inverted and complementary sequence of the miRNA of interest. The use of shorter regions of complementarity increases the number of potential sites and reduces the number of needed nucleotide changes.

RNA binding provides the ability to substitute cytosine (C) with uracil (U) and adenosine (A) with guanine (G) and still maintain a favorable mean free energy (MFE). Crick, *J Mol Biol* 19(2):548-555 (1966). As a result, codons such as 5'-UCU-3' (which encodes for Serine (S)) and 5'-UUU-3' (which encodes for phenylalanine (F)) can both hybridize to 5'-AGA-3'. Therefore, MRE targeting miRNA 5'-AGA-3' sequence, could be inserted in the influenza sequence that codes for either S or F. Examples of this are further depicted in Table 1.

adenosine (A) with guanine (G) in each of these putative MRE sequences allows any open reading frame that encodes for VLL, RAA, RVV, RAV, RVA, CAA, CVV, CAV, or CVA to be manipulated to become responsive to miR-16.

In the specific examples provided herein, the viral sequences are derived from Influenza A virus strain A/Puerto Rico/8/34/Mount Sinai(H1N1). Specifically, the specified nucleotide and amino acid positions correspond to the following GenBank Accession Nos.:

| Influenza coding region | GenBank Accession No. for nucleotide sequence | GenBank Accession No. for protein sequence |
|---|---|---|
| NP | AF389119.1 | AAM75159.1 |
| NS | AF389122.1 | AAM75164.1 |
| HA | AF389118.1 | AAM75158.1 |
| PA | AF389117.1 | AAM75157.1 |
| M | AF389121.1 | AAM75161.1 |
| PB1 | AF389116.1 | AAM75156.1 |
| PB2 | AF389115.1 | AAM75155.1 |
| NA | AF389120.1 | AAM75160.1 |

For each example, the mean free energy (MFE) may be further decreased by non-hierarchical amino acid substitutions (e.g., as described below for miR-93). Ideally, MFE of an MRE/miRNA interaction will be less than –20 kcal/mol, less than –25 kcal/mol, less than –30 kcal/mol, or less than –35 kcal/mol. For MFE calculation methods, see Dawson and Yamamoto, J. Theor. Biol., 1999, 201(2): 113-140.

It will be understood, however, that nucleotide substitutions that result in rare codon triplets such as ACG, UCG, CGU, or CGA (Lamer et al. *Gene* 345:127-138 (2005)) should be avoided unless this triplet is already represented in the viral region used for MRE insertion.

As exemplified herein, for influenza NP, it was found that positions 225 (site one) and 818 (site two) of segment five exhibit a high degree of sequence similarity to MRE sequences for miR-93. Thus, the sequence 5'-ACAAUA-

TABLE 1

"MRE Genetic Code"

| | | Second position | | | | |
|---|---|---|---|---|---|---|
| | | U | C | A | G | |
| First position (5'End) | U | UUU-F | UCU-S,F | UAU-Y,C | UGU-C | U  Third position |
| | | UUC-F | UCC-S | UAC-C,Y | UGC-C | C |
| | | UUA-L | UCA-S,L | UAA-W | UGA-*,W | A |
| | | UUG-L | UCG-S,L | UAG-*,W | UGG-* | G |
| | C | CUU-L,F | CCU-P,S,F,L | CAU-H,Y,C,R | CGU-R,C | U |
| | | CUC-L,F | CCC-P,S,F,L | CAC-H,R,Y,C | CGC-R,C | C |
| | | CUA-L | CCA-P,S,L | CAA-Q,W,R | CGA-R,W | A |
| | | CUG-L | CCG-P,L,S | CAG-R,Q | CGG-R | G |
| | A | AUU-I,V | ACU-I,V,A,T | AAU-N,V,G,M | AGU-S,G | U |
| | | AUC-I,V | ACC-A,T,I | AAC-N,G,S | AGC-S,G | C |
| | | AUA-I,V,M | ACA-V,A,M,I,T | AAA-K, L,N,G,E,R | AGA-R, G | A |
| | | AUG-I,V,M | ACG-T,A,M,V | AAG-K,E,G,R | AGG--R,G | G |
| | G | GUU-V,A | GCU-A,V | GAU-D,G | GGU-G | U |
| | | GUC-V | GCC-A,V | GAC-D,G | GGC-G | C |
| | | GUA-L | GCA-A,V | GAA-E,G | GGA-G | A |
| | | GUG-L | GCG-A,V | GAG-E | GGG-G | G |

For example, for miR-16 sequence: 5'-UAGCAG-CACGUAAAUAUUGGCG-3' (SEQ ID NO: 1), the minimal "seed" sequence can be viewed as either 5'-UAGCAGCAC-3' (SEQ ID NO: 8) or 5'-AGCAGCAGC-3' (SEQ ID NO: 9) making the complementary MRE sequence 5'-GTGCT-GCTA-3' (SEQ ID NO: 10) or 5'-CGTGCTGCTA-3' (SEQ ID NO: 11). Substituting cytosine (C) with uracil (U) and/or GAGAGAAUGGUGCUCUCU-3' (SEQ ID NO: 12) at site one was replaced with 5'-ACACUUGAACGAAUG-GUACUUUCU-3 (SEQ ID NO: 13) to create influenza 93NP1 and the sequence 5'-UUUCUAGCACGGUCUG-CACUCAUA-3' (SEQ ID NO: 14) at site two was replaced with 5'-UUCCUUGCACGGACAGCACUU UUA-3' (SEQ ID NO: 15) to create influenza 93NP2.

Tables 2-9, below, depict exemplary influenza A coding regions that can be modified at the nucleotide sequence level (without causing any changes in the target influenza amino acid sequences) to incorporate two or more MREs. Each of the disclosed MRE pairs or triplets is achieved by minimizing nucleotide sequence changes and by restricting amino acid substitutions according to the parameters depicted in Table 1, above.

TABLE 2 miR-16 MRE Sequences Incorporated within an Influenza A HA Coding Region

| | | SEQ ID |
|---|---|---|
| miR-16 | 5'-UAG CAG CAC GUA AAU AUU GGC G-3' | 1 |
| miR-16 MRE Nucleotide Sequence | 5'-C GCC AAT ATT TAC GTG CTG CTA-3' | 16 |
| miR-16 MRE + 1 Nucleotide Sequence | 5'-CGC CAA TAT TTA CGT GCT GCT A-3' | 17 |
| Influenza HA Site 1 (Amino Acids 2-9) | K A N L L V L L | 18 |
| Influenza HA Site 1 (Coding Strand) | 5'-AAG GCA AAC CTA CTG GTC CTG TTA-3' | 19 |
| Influenza HA Site 1 (Amino Acid Sequence Encoded by MRE-Strand) | K A N L L L L L | 20 |
| Influenza HA Site 1 (MRE-Strand) | 5'-AAG GCC AAC CTA TTA GTG CTG CTA-3' | 21 |
| Mean Free Energy | -29.2 kcal/mol | |
| Influenza HA Site 2 (Amino Acids 439-445) | N A E L L V L L | 22 |
| Influenza HA Site 2 (Coding Strand) | 5'-AAT GCA GAA TTG TTA GTT CTA CTG-3' | 23 |
| Influenza HA Site 2 (Amino Acid Sequence Encoded by MRE-Strand) | N A E L L V L L | 24 |
| Influenza HA Site 2 (MRE-Strand) | 5'-AAC GCC GAA CTA TTA GTG CTG CTA-3' | 25 |
| Mean Free Energy | -30.1 kcal/mol | |

TABLE 3 miR-17 MRE Sequences Incorporated within an Influenza A PB1 Coding Region

| | | SEQ ID |
|---|---|---|
| miR-17 | 5'-CAA AGU GCU UAC AGU GCA GGU AG-3' | 2 |
| miR-17 MRE Nucleotide Sequence | 5'-CT ACC TGC ACT GTA AGC ACT TTG-3' | 26 |
| miR-17 MRE + 1 Nucleotide Sequence | 5'-C TAC CTG CAC TGT AAG CAC TTT G-3' | 27 |
| Influenza PB1 Site 1 (Amino Acids 374-381) | A S I D L K Y F | 28 |
| Influenza PB1 Site 1 (Coding Strand) | 5'-GCA AGC ATT GAT TTG AAA TAT TTC-3' | 29 |
| Influenza PB1 Site 1 (Amino Acid Sequence Encoded by MRE-Strand) | A S I D L K Y F | 30 |
| Influenza PB1 Site 1 (MRE-Strand) | 5'-GCC AGC ATT GAT CTT AAG TAC TTT-3' | 31 |

TABLE 3-continued miR-17 MRE Sequences Incorporated within an
Influenza A PB1 Coding Region

| | | SEQ ID |
|---|---|---|
| Mean Free Energy | -26.3 kcal/mol | |
| Influenza PB1 Site 2 (Amino Acids 418-424) | V L G V S I L | 32 |
| Influenza PB1 Site 2 (Coding Strand) | 5'-GTA TTA GGC GTC TCC ATC CTG-3' | 33 |
| Influenza PB1 Site 2 (Amino Acid Sequence Encoded by MRE-Strand) | V L G V S I L | 34 |
| Influenza PB1 Site 2 (MRE-Strand) | 5'-GTG TTG GGT GTA AGC ATT TTG-3' | 35 |
| Mean Free Energy | -23.2 kcal/mol | |
| Influenza PB1 Site 3 (Amino Acids 677-683) | T S Q R G V L | 36 |
| Influenza PB1 Site 3 (Coding Strand) | 5'-ACA AGT CAA AGA GGA GTA CTT-3' | 37 |
| Influenza PB1 Site 3 (Amino Acid Sequence Encoded by MRE-Strand) | T S Q R G V L | 38 |
| Influenza PB1 Site 3 (MRE-Strand) | 5'-ACC AGC CAA AGA GGC GTT TTG-3' | 39 |
| Mean Free Energy | -20.0 kcal/mol | |

TABLE 4 miR-19 MRE Sequences Incorporated within an Influenza A HA Coding Region

| | | SEQ ID |
|---|---|---|
| miR-19 | 5'-UGU GCA AAU CUA UGC AAA ACU GA-3' | 3 |
| miR-19 MRE Nucleotide Sequence | 5'-TC AGT TTT GCA TAG ATT TGC ACA-3' | 40 |
| miR-19 MRE + 1 Nucleotide Sequence | 5'-T CAG TTT TGC ATA GAT TTG CAC A-3' | 41 |
| Influenza HA Site 1 (Amino Acids 15-22) | A D A D T I C I | 42 |
| Influenza HA Site 1 (Coding Strand) | 5'-GCA GAT GCA GAC ACA ATA TGT ATA-3' | 43 |
| Influenza HA Site 1 (Amino Acid Sequence Encoded by MRE-Strand) | A D A D T I C I | 44 |
| Influenza HA Site 1 (MRE-Strand) | 5'-gcc agt gct gac aca att tgc ata-3' | 45 |
| Mean Free Energy | -19.3 kcal/mol | |
| Influenza HA Site 2 (Amino Acids 561-568) | S L Q C R I C I | 46 |
| Influenza HA Site 2 (Coding Strand) | 5'-TCT TTG CAG TGC AGA ATA TGC ATC-3' | 47 |
| Influenza HA Site 2 (Amino Acid Sequence Encoded by MRE-Strand) | S L Q C R I C I | 48 |

TABLE 4-continued miR-19 MRE Sequences Incorporated within an Influenza A HA Coding Region

| | | SEQ ID |
|---|---|---|
| Influenza HA Site 2 (ARE-Strand) | 5'-tct ttg cag tgc agg att tgc ata-3' | 49 |
| Mean Free Energy | -24.2 kcal/mol | |
| Influenza HA Site 3 (Amino Acids 327-334) | L R M V T G L R | 50 |
| Influenza HA Site 3 (Coding Strand) | 5'-TTG AGG ATG GTT ACA GGA CTA AGG-3' | 51 |
| Influenza HA Site 3 (Amino Acid Sequence Encoded by MRE-Strand) | L R M V T G L R | 52 |
| Influenza HA Site 3 (MRE-Strand) | 5'-ttg cgu atg gtC aca ggt ttg cgc-3' | 53 |
| Mean Free Energy | -22.4 kcal/mol | |

TABLE 5 miR-25 MRE Sequences Incorporated within an Influenza A M1 Coding Region

| | | SEQ ID |
|---|---|---|
| miR-25 | 5'-CAU UGC ACU UGU CUC GGU CUG A-3' | 4 |
| miR-25 MRE Nucleotide Sequence | 5'-T CAG ACC GAG ACA AGT GCA ATG-3' | 54 |
| miR-25 MRE + 1 Nucleotide Sequence | 5'-TCA GAC CGG GAC AAG TGC AAT G-3' | 55 |
| Influenza M1 Site 1 (Amino Acids 111-118) | G A K E I S L S | 56 |
| Influenza M1 Site 1 (Coding Strand) | 5'-GGG GCC AAA GAA ATC TCA CTC AGT-3' | 57 |
| Influenza M1 Site 1 (Amino Acid Sequence Encoded by MRE-Strand) | G A K E I S L S | 58 |
| Influenza M1 Site 1 (MRE-Strand) | 5'-ggt gcc aaa gag ata agt gca agt-3' | 59 |
| Mean Free Energy WIIIIIMINIMMINEIM | -27.7 cal/mol | |
| Influenza M1 Site 2 (Amino Acids 127-134) | I Y N R M G A V | 60 |
| Influenza rn Site 2 (Coding Strand) | 5'-ATA TAC AAC AGG ATG GGG GCT GTG-3' | 61 |
| Influenza M1 Site 2 (Amino Acid Sequence Encoded by MRE-Strand) | I Y N R M G A V | 62 |
| Influenza M1 Site 2 (MRE-Strand) | 5'-ata tac aac agg atg ggt gca gtg-3' | 63 |
| Mean Free Energy | -24.0 kcal/mol | |

TABLE 6 miR-34 MRE Sequences Incorporated within an Influenza A PA1 Coding Region

| | | SEQ ID |
|---|---|---|
| miR-34 | 5'-UGG CAG UGU CUU AGC UGG UUG U-3' | 5 |
| miR-34 MRE Nucleotide Sequence | 5'-A CAA CCA GCT AAG ACA CTG CCA-3' | 64 |
| miR-34 MRE + 1 Nucleotide Sequence | 5'-ACA ACC AGC TAA GAC ACT GCC A-3' | 65 |
| Influenza PA1 Site 1 (Amino Acids 426-433) | D E I G E D V A | 66 |
| Influenza PA1 Site 1 (Coding Strand) | 5'-GAT GAG ATT GGA GAA GAT GTG GCT-3' | 67 |
| Influenza PA1 Site 1 (Amino Acid Sequence Encoded by MRE-Strand) | D E I G E D V A | 68 |
| Influenza PA1 Site 1 (MRE-Strand) | 5'-gat gag atc ggt gaa gac gtt gcc-3' | 69 |
| Mean Free Energy | −27.4 kcal/mol | |
| Influenza PA1 Site 2 (Amino Acids 634-641) | G K V C R T L L | 70 |
| Influenza PA1 Site 2 (Coding Strand) | 5'-GGG AAG GTC TGC AGG ACT TTA TTA-3' | 71 |
| Influenza PA1 Site 2 (Amino Acid Sequence Encoded by MRE-Strand) | G K V C R T L L | 72 |
| Influenza PA1 Site 2 (MRE-Strand) | 5'-ggc aag gta tgt agg aca ctg tta-3' | 73 |
| Mean Free Energy | −25.6 kcal/mol | |
| Influenza PA1 Site 2 (Amino Acids 709-716) | S F L T H A L S | 74 |
| Influenza PA1 Site 2 (Coding Strand) | 5'-TTC TTC CTT ACA CAT GCA TTG AGT-3' | 75 |
| Influenza PA1 Site 2 (Amino Acid Sequence Encoded by MRE-Strand) | S F L T H A L S | 76 |
| Influenza PA1 Site 2 (MRE-Strand) | 5'-ttc ttc ctg act cat gca ctg tca-3' | 77 |
| Mean Free Energy | −24.2 kcal/mol | |

TABLE 7 miR-92 MRE Sequences Incorporated within an Influenza A HA Coding Region

| | | SEQ ID |
|---|---|---|
| miR-92 | 5'-UAU UGC ACU UGU CCC GGC CUG-3' | 6 |
| miR-92 MRE Nucleotide Sequence | 5'-CAG GCC GGG ACA AGT GCA ATA-3' | 78 |
| miR-92 MRE + 1 Nucleotide Sequence | 5'-CA GGC CGG GAC AAG TGC AAT A-3' | 79 |

TABLE 7-continued miR-92 MRE Sequences Incorporated-
within an Influenza A HA Coding Region

| | | SEQ ID |
|---|---|---|
| Influenza HA Site 1 (Amino Acids 68-74) | Q L G K C N I | 80 |
| Influenza HA Site 1 (Coding Strand) | 5'-CTA CAA TTG GGG AAA TGT AAC-3' | 81 |
| Influenza HA Site 1 (Amino Acid Sequence Encoded by MRE-Strand) | Q L G K C N I | 82 |
| Influenza HA Site 1 (MRE-Strand) | 5'-cta cag ttg ggg aag tgc aat-3' | 83 |
| Mean Free Energy | -26.1 kcal/mol | |
| Influenza HA Site 2 (Amino Acids 195-201) | N A Y V S V V | 84 |
| Influenza HA Site 2 (Coding Strand) | 5'-AAT GCT TAT GTC TCT GTA GTG-3' | 85 |
| Influenza HA Site 2 (Amino Acid Sequence Encoded by MRE-Strand) | N A Y V S V V | 86 |
| Influenza HA Site 2 (MRE-Strand) | 5'-aac gcc tat gta agt gta gta-3' | 87 |
| Mean Free Energy | -20.0 kcal/mol | |
| Influenza HA Site 3 (Amino Acids 526-532) | L V S L G A I | 88 |
| Influenza HA Site 3 (Coding Strand) | 5'-TTG GTC TCC CTG GGG GCA ATC-3' | 89 |
| Influenza HA Site 3 (Amino Acid Sequence Encoded by MRE-Strand) | L V S L G A I | 90 |
| Influenza HA Site 3 (MRE-Strand) | 5'-ttg gtc agt tta ggt gca ata-3' | 91 |
| Mean Free Energy | -24.9 kcal/mol | |

TABLE 8 miR-92 MRE Sequences Incorporated within an Influenza A NS1 Coding Region

| | | SEQ ID |
|---|---|---|
| miR-92 | 5'-UAU UGC ACU UGU CCC GGC CUG-3' | 6 |
| miR-92 MRE Nucleotide Sequence | 5'-CAG GCC GGG ACA AGT GCA ATA-3' | 92 |
| miR-92 MRE + 1 Nucleotide Sequence | 5'-CA GGC CGG GAC AAG TGC AAT A-3' | 93 |
| Influenza NS1 Site 1 (Amino Acids 131-137) | K A N F S V I | 94 |
| Influenza NS1 Site 1 (Coding Strand) | 5'-AAA GCA AAC TTC AGT GTG ATT-3' | 95 |

TABLE 8-continued miR-92 MRE Sequences Incorporated within an Influenza A NS1 Coding Region

| | | SEQ ID |
|---|---|---|
| Influenza NS1 Site 1 (Amino Acid Sequence Encoded by MRE-Strand) | K A N F S V I | 96 |
| Influenza NS1 Site 1 (MRE-Strand) | 5'-aag gcc aac ttc agt gta ata-3' | 97 |
| Mean Free Energy | -23.9 kcal/mo | |
| Influenza NS1 Site 2 (Amino Acids 150-156) | F T E E G A I | 98 |
| Influenza NS1 Site 2 (Coding Strand) | 5'-TTC ACC GAA GAG GGA GCA ATT-3' | 99 |
| Influenza NS1 Site 2 (Amino Acid Sequence Encoded by MRE-Strand) | F T E E G A I | 100 |
| Influenza NS1 Site 2 (MRE-Strand) | 5'-ttc acc gag gaa ggt gca ata-3' | 101 |
| Mean Free Energy | -24.7 kcal/mol | |

TABLE 9 miR-93 MRE Sequences Incorporated within an Influenza A NP Coding Region

| | | SEQ ID |
|---|---|---|
| miR-93 | 5'-CAA AGU GCU GUU CGU GCA GGU AG-3' | 7 |
| miR-93 MRE Nucleotide Sequence | 5'-CT ACC TGC ACG AAC AGC ACT TTG-3' | 102 |
| miR-93 MRE + 1 Nucleotide Sequence | 5'-C TAC CTG CAC GAA CAG CAC TTT G-3' | 103 |
| Influenza NP Site 1 (Amino Acids 62-69) | T I E R M V L S | 104 |
| Influenza NP Site 1 (Coding Strand) | 5'-ACA ATA GAG AGA ATG GTG CTC TCT-3' | 105 |
| Influenza NP Site 1 (Amino Acid Sequence Encoded by MRE-Strand) | T I E R M V L S | 106 |
| Influenza NP Site 1 (MRE-Strand) | 5'-aca att gaa cga atg gta ctt tct-3' | 107 |
| Mean Free Energy | -23.8 kcal/mol | |
| Influenza NP Site 2 (Amino Acids 258-265) | F L A R S A L I | 108 |
| Influenza NP Site 2 (Coding Strand) | 5'-TTT CTG GCA CGG TCT GCA CTC ATA-3' | 109 |
| Influenza NP Site 2 (Amino Acid Sequence Encoded by MRE-Strand) | F L A R S A L I | 110 |
| Influenza NP Site 2 (MRE-Strand) | 5'-ttc ctt gca cgg tca gca ctt ata-3' | 111 |
| Mean Free Energy | -32.1 kcal/mol | |

The MREs useful for the present invention can be derived, e.g., from any miRNA which is highly expressed in mammalian (e.g., human) cells (including, e.g., epithelial, secretory [Clara], ciliated, apical, goblet [mucous], hematopoeitic [e.g., dendritic cells, macrophages, lymphocytes], bronchial, and other cells of the lung and upper respiratory tract targeted by the influenza virus) but is not expressed or is expressed at very low levels in the regions where viral propagation occurs within embryonated chicken eggs (*Gallus gallus*) or a cell line used for vaccine production (e.g. MDCK cells [e.g., ATCC Catalog No. CCL-34]). This allows efficient vaccine production in ovo or in vitro but renders the vaccine virus susceptible to attenuation in mammalian (e.g., human) cells expressing a cognate miRNA.

Table 10 shows relative data of miRNA expression in the allantoic membrane of 10 day old chicken (*Gallus gallus*) eggs versus human A549 lung epithelial cells. It is based on high throughput parallel sequencing of more than 3000000 assembled sequences ("reads") formed by ligating RNA adaptors to purified cellular RNAs. The percent given represents the total number of miRNA specific reads divided by the total number of miRNA reads.

TABLE 10

Comparative miRNA expression

| microRNA | Human lung epithelium | Chicken egg membrane |
|---|---|---|
| miR-16 | 0.3% | ND |
| miR-17 | 1.2% | .01% |
| miR-19 | 2.3% | 0.01% |
| miR-25 | 1.3% | ND |
| miR-34 | 2.1% | ND |
| miR-92 | 0.12% | 0.01% |
| miR-93 | 1.7% | ND |

Percents were derived as number of reads/total reads as follows:
ND denotes "not detected"

Based on the above data, miR-16, miR-17, miR-19, miR-25, miR-34, miR-92, and miR-93 represent strong candidates for the generation of mammalian-specific, MRE-containing LAIV vaccines.

Additional useful miRNAs can be identified by parallel sequencing and determination of the relative expression levels between the two species, tissues, or cell lines of interest. See the current database of miRNA sequences on the WorldWideWeb at mirbase.org (miRBase).

The recombinant LAIV of the present invention can further comprise additional attenuating mutations, including, e.g., mutations which result in a temperature-sensitive viral propagation (e.g., a mutation which is used in FLUMIST) and removal of a pathogenic factor (e.g., removal of NS1 protein).

Production of Recombinant Live Attenuated Influenza Viruses

After the generation of MRE-containing recombinant constructs, live attenuated MRE-containing viruses of the invention can be produced recombinantly in cultured cells (e.g., in human embryonic kidney HEK-293 cells [ATCC Catalog No. CRL-1573], chicken fibroblasts DF1 [ATCC Catalog No. CRL-12203], Madin-Darby Canine Kidney (MCK) cells [ATCC Catalog Nos. CCL-34, CRL-2285, CRL-2286, CRL-2935, or CRL-2936], African green monkey kidney cells (Vero) [ATCC Catalog Nos. CCL-81, CRL-1586, CRL-1587, or CRL-2783], human PER-C6 cells (Pau et al. Vaccine 19(17-19) 2716, (2001)), chicken fibroblasts DF1 [ATCC Catalog No. CRL-12203]. Production in cell lines may be followed by propagation in embryonated chicken eggs to obtain higher titers.

At each step, viral particles can be purified, e.g., by ultrafiltration or ultracentrifugation, preferably continuous centrifugation (see Furminger, In: Nicholson, Webster and May (eds.), Textbook of Influenza, Chapter 24, pp. 324-332). Viral titers can be determined by plaque assay, tissue culture infectious dose, egg infectious dose, hemagglutination inhibition, or by antibody-dependent fluorescence. Huprikar et al., J Virol Methods, 1980, 1(2):117-120, Rimmelzwaan et al., J Virol Methods. 1998, 74(1): 57-66.

The recombinant attenuated influenza viruses of the invention can be derived from various influenza genetic backgrounds, including without limitation, H5N1 virus (e.g., A/Vietnam/1203/04, A/chicken/Scotland/59, A/duck/Hong Kong/308/78), H1N1 virus (e.g., A/PuertoRico/8/1934, A/NewYork/616/1995, A/California/04/2009), H3N2 virus (e.g., A/HongKong/16/68, A/USSR/039/68, A/Yokohama/C5/85), or any other influenza A virus, including cold-adapted strains A/Leningrad/134/17/57, A/Leningrad/134/47/57 and A/Ann Arbor/6/60.

The recombinant attenuated influenza viruses of the invention can be made in cultured cells by any means known to those of skill in the art, including through a genetic engineering method such as the "plasmid only" system wherein the plasmid-driven expression of eight influenza vRNAs from a pol I promoter and all mRNAs from a pol II promoter results in the formation of an infectious influenza virus (Hoffmann et al., Proc. Natl. Acad. Sci. USA 2000, 97:6108; Hoffmann et al., Vaccine 2002, 20:3165; U.S. Pat. No. 6,951,754; Quinlivan et al., *J. Virol.* 79(13):8431 (2005)). In order to avoid attenuation during viral propagation in mammalian cells, the MRE-containing plasmid is driven only by RNA pol I to produce vRNA containing the MRE in an inverse, and therefore ineffective, orientation and another plasmid (not containing the MRE) is driven only by RNA pol II promoter to produce a wild-type mRNA. For example, as specified in the Example 11, below, to produce recombinant attenuated influenza viruses containing MRE in the NP open reading frame, the inventors used one plasmid (pCAGGs NP) driven only by RNA pol II promoter to produce wild type NP mRNA and another plasmid (pPol I MRE-encoded NP) driven only by RNA pol I to produce vRNA containing MRE in the NP open reading frame.

In an alternative method, the MRE-containing vRNA segment of interest can be overexpressed and then the cell can be infected with a viral strain of interest at a very low multiplicity of infection (MOD, e.g., 1 virus/100 cells. Overexpression of the viral segment of interest will result in its incorporation. Following inoculation in eggs, the heterogenous viruses can be plaque purified and can be distinguished from the wild-type virus by plaque size in cultured cells. Alternatively, additional selection pressure can be added during rescue by transfecting a short interfering RNA (siRNA) targeted to only the wild-type—unmodified strand. This would select for recombinants only.

In order to achieve a large-scale virus production, supernatant and/or cultured cells used for the initial virus production can be injected into 10-day old embryonated chicken eggs. Alternatively, MDCK cells may be engineered to propagate an MRE-containing virus by (i) stable knockdown of the corresponding miRNA through lentiviral integration (Gentner et al., *Nature Methods* (2009) 63-66) or (ii) expression of a zinc-finger nuclease specific for Dicer or Drosha (Miller et al., *Nature Biotechnology* (2007); 778-85) or (iii) by incorporating MREs corresponding to miRNAs that are not expressed or are expressed at very low levels in MDCK cells.

Because the miRNAs corresponding to MREs present in the recombinant live attenuated influenza viruses of the present invention are absent from or expressed at very low levels in allantoic membranes of chickens or in cell lines used for vaccine production, but are abundant in mammalian tissues (e.g., lung tissue and other tissues targeted by the influenza virus), these vaccines are selectively attenuated in mammalian cells yet can be propagated to very high titers in chicken allantoic membranes or in a cell line of choice (e.g., Madin-Darby Canine Kidney (MCK) cells [ATCC Catalog Nos. CCL-34, CRL-2285, CRL-2286, CRL-2935, or CRL-2936], African green monkey kidney cells (Vero) [ATCC Catalog No. CCL-81, CRL-1586, CRL-1587, or CRL-2783], human PER-C6 cells (Pau et al. Vaccine 19(17-19) 2716, (2001), or chicken fibroblasts DF1 [ATCC Catalog No. CRL-12203]). Thus, MRE-containing influenza virus vaccines of the present invention allow to achieve viral titers of greater than $1 \times 10^7$ plaque forming units per milliliter (pfu/mL) and permit vaccine propagation using standard tissue culture or high-density cell fermentation technology (Meghrou et al, Vaccine 28(2) 309 (2009)).

Vaccine Compositions of the Invention

The present invention also provides novel improved LAIV vaccine compositions comprising an MRE-containing live attenuated influenza virus and a pharmaceutically acceptable carrier or diluent. The vaccine may be used in a method of prophylaxis of a disease condition caused by the influenza virus by administering to a subject in need thereof a therapeutically effective amount of the vaccine.

Strategies to further enhance influenza vaccine effectiveness include, e.g., the conjoint administration of adjuvants (see above) or immunostimulatory molecules such as cytokines, lymphokines, or chemokines (e.g., interleukins IL-1, IL-2, IL-3, IL-4, IL-12, IL-13, granulocyte-macrophage colony stimulating factor (GM-CSF) and other colony stimulating factors, macrophage inflammatory factor, Flt3 ligand, B7.1, B7.2, etc.). Salgaller and Lodge, J. Surg. Oncol. 1998, 68: 122; Lyman, Curr. Opin. Hematol., 5: 192, 1998. Adjuvants or immunostimulatory molecules can be delivered systemically or locally (e.g., directly as proteins or by expression from a vector). See Wood and Williams, In: Nicholson, Webster and May (eds.), Textbook of Influenza, Chapter 23, pp. 317-323; Salgaller and Lodge, J. Surg. Oncol. 1998, 68:122.

A therapeutically effective protective dose of the LAIV vaccine of the invention can be administered by various administration routes known in the art. Mucosal administration is particularly preferred for live attenuated vaccines, since influenza infection occurs via the mucosa and the mucosa harbors dendritic cells, which are important targets for immunotherapy. Examples of useful mucosal vaccination strategies include, among others, encapsulating the virus in microcapsules (U.S. Pat. Nos. 5,075,109; 5,820,883, 5,853, 763) and using an immunopotentiating membranous carrier (PCT Publication No. WO 98/0558). In a specific embodiment, the vaccines of the invention can be administered mucosally in an admixture with, or as a conjugate or chimeric fusion protein with, cholera toxin (CT), such as CT B or a CT A/B chimera (Hajishengallis, J. Immunol., 154: 4322-32, 1995; Jobling and Holmes, Infect Immun., 60: 4915-24, 1992). Mucosal vaccines based on the use of the CT B subunit have been described (Lebens and Holmgren, Dev Biol Stand 82: 215-27, 1994). In another embodiment, an admixture with heat labile enterotoxin (LT) can be prepared for mucosal vaccination. The immunogenicity of inhalation-based administered vaccine can be also enhanced by using red blood cells (rbc) or rbc ghosts (U.S. Pat. No. 5,643,577), or by using blue tongue antigen (U.S. Pat. No. 5,690,938).

Although the above approaches are promising for improved future vaccination strategies, their use in specific situations requires validation and surveillance to ensure vaccine effectiveness.

To assess the potency of the vaccine, the single radial immunodiffusion (SRD) test can be used. Schild et al., Bull. World Health Organ. 1975, 52: 43-50 and 223-31 Mostow et al., J. Clin. Microbiol. 1975, 2: 531. The dose needed for a satisfactory immune response has been standardized and is 15 μg HA/strain/dose for SRD or a minimum of neutralizing activity in.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Virus Infections

Animal infections were performed in accordance with NIH standards. 5 week-old Balb/c mice were purchased from Taconic Farms, Inc. (Albany, N.Y.). Mice were put under general anesthetic for approximately 5 min via inhalation of isoflorane, and a 50 μL volume of virus (resuspended in PBS) was placed on the snares of the mice as they regained consciousness. Viruses were titered by standard plaque assay and pathogenic studies were performed on cohorts of 3-5 mice/ inoculating dose. Mice were weighed daily and sacrificed if they lost 20% of the original body mass. Vaccination studies using $1 \times 10^3$ plaque forming units (pfu) of MRE-containing H5N1 virus or mock PBS infections were performed intranasally (PBS, n=2; MRE-containing H5N1, n=7). 21 days post infection, mice were re-challenged intranasally with $1 \times 10^6$ PRNTL H5N1 and were monitored daily for signs of morbidity and mortality.

Example 2

Passaging and Sequencing of Viral NP

Human lung epithelial cells were infected with PRNTL or MRE-containing H5N1 at an MOI of 0.01 in the presence of TPCK trypsin. 24 hrs post-infection, supernatant was transferred to naive cells and repeated the following day for a total of 10 passages. 10 dpi, RT-PCR was performed on total RNA and NP PCR products were cloned for sequencing purposes. For in vivo studies, 5 week old Balb/c mice were treated with virus as above. 5 dpi, total RNA was harvested, and used to clone NP for sequencing. Depicted sequences represent over 25 individual colonies per cohort.

Example 3 miRNA Expression and Targeted Luciferase Vectors

The red fluorescent protein minigene expressing miR-124 was generated by E. Makeyev. Makeyev et al., *Molecular Cell* 27(3):435 (2007). For generation of pRFP-miR-93, a 500 bp genomic fragment containing the pri-miR-93 locus was isolated from mouse genomic DNA by PCR amplification with High Fidelity PCR Master Kit (Roche Applied Science, Indianapolis, Ind.) per the provided protocol, using forward 5'-TAGTGGTCCTCTCTGTGCTACCG-3' (SEQ ID NO: 112) and reverse 5'-ATTGAACAAAAATGGGGACTCCT-3' (SEQ ID NO: 113) primers. The resulting PCR product was subcloned into pCR® 2.1-TOPO (Invitrogen Corporation, Carlsbad, Calif.) according to the manufacturer's suggestions, and subsequently cloned into the pRFP minigene via PmeI-SpeI sites. Firefly luciferase constructs containing miR-124 MREs and control SV40 3' UTRs were obtained from E. Makeyev. Makeyev et al., *Molecular Cell* 27(3):435 (2007).

Example 4

Tissue Culture and Ex Vivo Infection

Human embryonic kidney HEK-293 cells, human lung epithelial A549 cells, human astrocytoma U373 cells, and murine fibroblasts were grown in Dulbecco's minimal essential medium (DMEM, Mediatech, Inc., Manassas, Va.), supplemented with 10% fetal bovine serum (JM Bioscience, San Diego, Calif.) and 1% penicillin/streptomycin (Mediatech), unless otherwise indicated. Dicer–/– murine fibroblasts were a kind gift from A. Tarahkovsy (Rockefeller University, New York City, N.Y.), and were grown in DMEM supplemented with 15% FBS, 1% nonessential amino acids (GIBCO, Invitrogen), and 1% penicillin/streptomycin. Jurkat cells were grown in alpha minimal essential medium, supplemented with 10% fetal bovine serum, and 1% penicillin/streptomycin. Primary human dendritic cell RNA was provided by A. Fernendez-Sesma (Mount Sinai School of Medicine, New York City, N.Y.). Ex vivo infections of fibroblasts were performed in complete media and the absence of trypsin at an MOI of one for wild type fibroblasts and five for Dicer–/– fibroblasts and harvested at the indicated time points.

Example 5

RT-PCR and Western Blot

RT-PCR and immunoblots were performed as recently described. tenOever et al., *Science* 315(5816):1274 (2007). Actin (Cat. No. 8226; Abcam Inc., Cambridge, Mass.), polyclonal PR8 (from A. Garcia-Sastre, Mount Sinai School of Medicine, New York City, N.Y.), IRF1 (sc-640; Santa Cruz Biotechnology, Inc., Santa Cruz, Calif.), STAT1 (sc-417, Santa Cruz Biotechnology, Inc.), and ISG54 (from G. Sen, Cleveland Clinic, Cleveland, Ohio) antibodies were all used at a concentration of 1 µg/µL and incubated overnight at 4° C. Secondary mouse and rabbit antibodies (GE Healthcare, Chalfont St. Giles, United Kingdom) were used at a 1:1000 dilution for one hour at room temperature. miRNA RT-PCR primers are presented in Table 1.

TABLE 1 miRNA RT-PCR Primer Sequences

| | SEQUENCE | SEQ ID |
|---|---|---|
| miR-342 | 5'-AACACCTTCAGAGTCGTTGGAGT-3' | 114 |
| miR-342 | 5'-GGAGGCCCACTACATGAGAC-3' | 115 |
| Let-7a | 5'-GTCCTGGCGCGGTGCTCT-3' | 116 |
| Let-7a | 5'-TCTCTTGCTCCTTCCMGC-3' | 117 |
| miR-155 | 5'-CATTTCAAGAACAACCTACCAGAGA-3' | 118 |
| miR-155 | 5'-AAGTTTATCCAGCAGGGTGACTC-3' | 119 |
| mIR-16 | 5'-TCTGATGTGAACACAAGGACATTCA-3' | 120 |
| mIR-16 | 5'-'TTTCCACCATCTTTACCCTGTTT-3' | 121 |
| miR-93 | 5'-GAAGCTCATGAGGCGTTACATAG-3' | 122 |
| miR-93 | 5'-ATTGACCTGCCAGACATTGAG-3' | 123 |
| miR-128-1 | 5'-TTCCCAGTCCACTGTGGTTCTTC-3' | 124 |
| miR-128-1 | 5'-TGGCACTGAAGTATAGGGGATG-3' | 125 |
| miR-128-2 | 5'-CCCAGCTATGTAATCGCCTCTA-3' | 126 |
| miR-128-2 | 5'-CTGCCTGGTTAGGTAGCATGA-3' | 127 |
| miR-30e | 5'-GATGAACTGAAACCTCCAAAGC-3' | 128 |
| miR-30e | 5'-ATCTGCTGGATCTCTCCTGTGT-3' | 129 |
| miR-181 | 5'-CAACGGTTTCTGTCAGGATGAAT-3' | 130 |
| miR-181 | 5'-AGGGGAACTGTGGTCACTATCAC-3' | 131 |
| mIR-21 | 5'-TGCTTGGGAGGAAAATAAACAAT-3' | 132 |
| mIR-21 | 5'-GACTCTAAGTGCCACCAGACAGA-3' | 133 |
| tubulin | 5'-GCCTGGACCACAAGTTTGAC-3' | 134 |
| tubulin | 5'-TGAAATTCTGGGAGCATGAC-3' | 135 |

Example 6 pRFP and Luciferase Reporter Transfections

Transfections for fluorescence confirmation of pRFP constructs were performed with HEK293s grown in DMEM with 10% FBS, using 4 µg appropriate pRFP vector and Lipofectamine 2000 (Invitrogen), according to the provided protocol. Fluorescence was imaged 24 hours post transfection. For subsequent infection with WT influenza A/Puerto Rico/8/34, HEK293s were transfected using Lipofectamine 2000 (Invitrogen) and a mixture containing 100 ng appropriate firefly luciferase 3' UTR construct, 10 ng constitutive firefly *Renilla*, and 700 ng appropriate pRFP construct. Cells were infected at an MOI=1 at 6 hours post transfection, and subsequently harvested for the Dual-Luciferase® Reporter Assay (Promega, Madison, Wis.) 18 hours post infection. For co-transfection with either pBluescript SK+ (Stratagene, Agilent Technologies, La Jolla, Calif.) or pDZ-NS1 (all pDZ constructs were from P. Palese, Mount Sinai School of Medicine, New York City, N.Y.), HEK293s were transfected using Lipofectamine 2000 (Invitrogen) and a mixture containing 50 ng appropriate firefly luciferase 3' UTR, 10 ng constitutive firefly *Renilla,* 350 ng appropriate pRFP construct, and 350 ng either pBluescript SK+ (Stratagene) or pDZ-NS1 (vector described below). Cells were harvested 24 hours post transfection for Dual-Luciferase® Reporter Assay (Promega) per the manufacturer's protocol. All firefly luciferase readings were expressed as a ratio to firefly Renilla expression per sample, and subsequently averaged over three replicates.

Example 7

Statistical Analyses

Statistical analysis was performed using a two-tailed student's T-test with an n=3-8. p-values<0.05 were considered significant, and error bars reflect +/−standard deviation.

Example 8 miRNA Northern Blot Analysis

Total RNA was extracted using Trizol Reagent (Invitrogen) per the supplied protocol, and separated by polyacrylamide gel electrophoresis (PAGE) with a 15% denaturing polyacrylamide gel containing 7.5M urea and 1×TBE. Makeyev et al., Molecular Cell 27(3):435 (2007). The RNA was subsequently transferred to Hybond N+ membrane (Amersham, GE Healthcare Life Sciences) in 0.5×TBE at 360 mA for 60 minutes, cross-linked to the membrane by UV irradiation at 200,000 microJoules/cm$^2$, and the membrane was blocked overnight at 65° C. in 6×SSC, 7% SDS. Hybridization probes are presented in Table 2.

TABLE 2

Primer Sequences

| | SEQUENCE | SEQ ID |
|---|---|---|
| anti-miR-124 | 5'-TGGCATTCACCGCGTGCCTTAA-3' | 136 |
| anti-miR-93 | 5'-CTACCTGCACGAACAGCACTTTG-3' | 137 |
| anti-U6 | 5'-GCCATGCTAATCTTCTCTGTATC-3' | 138 |

Oligonucleotides depicted in Table 2 were radiolabeled using T4 polynucleotide kinase (Invitrogen) and [γ$^{32}$P]ATP (PerkinElmer, Waltham, Mass.) and purified by Sephadex G-25 columns (GE Healthcare). Probes were added to the blocking solution at approximately 10 million counts per minute and incubated overnight at 42° C. The blots were subsequently washed four times with 3×SSC, 0.1% SDS at 42° C., and imaged overnight by autoradiogram.

Example 9

Incorporation of MREs into Influenza A/Puerto Rico/8/34 Nucleocapsid

Sites within influenza A/Puerto Rico/8/34 nucleocapsid with partial complementarity to miR-93 were identified using Bibiserv's RNAhybrid algorithm (Bielefeld University Bioinformatics Service, Centrum für Biotechnologie—CeBiTec, Bielefeld, Germany). Nearly full complementarity was achieved with 3-5 steps of site-directed mutagenesis using the QuickChange® kit and protocol (Stratagene) on the pPol-I driven NP vector for viral RNA expression.

Example 10

RNA-Dependent RNA Polymerase Activity of Mutant NP

The PRNTL1/2 site was cloned from the pPol-I vector into the pDZ backbone for expression of protein in vitro. For RdRp driven Luciferase expression, 250 ng of pDZ-NP-PRNTL1/2 or WT pDZ-NP was transfected into HEK293s along with 100 ng firefly luciferase driven by a pPol-I based plasmid, 10 ng constitutive firefly Renilla, and the remaining influenza virus polymerase segments: 62.5 ng PB1, 62.5 ng PA, and 25 ng PB2. Hoffmann et al., Antiviral Research 80(2):124 (2008). Firefly luciferase activity was determined using the Dual-Luciferase® Reporter Assay (Promega) and expressed as a ratio to firefly Renilla expression per sample, with the average calculated over three replicates.

Example 11

Rescue of Recombinant Influenza A Viruses

The pPol-I NP mutants described herein were used to rescue live virus. HEK 293 cells were transfected using Lipofectamine 2000 (Invitrogen) with mutant pPol-I NP constructs along with WT pCAGGS NP and the seven pDZ constructs corresponding to the remaining seven influenza segments as previously described. Park et al., Proc. Natl. Acad. Sci. U.S.A. 103(21):8203 (2006). Cells were harvested 24 hours post transfection and injected into the Chorioallontoic fluid of fertilized chicken eggs. Live virus was isolated 48 hours post injection and quantified both by hemagglutination assay and plaque assay. H5N1 recombinant influenza A viruses were generated in a similar manner, using constructs previously described.

Example 12

Exogenous miRNA Hairpin Expression and Post-Transcriptional Gene Silencing

To express miRNAs exogenously, the miRNA hairpin within its genomic context was cloned as an intron of the red fluorescent protein (RFP), thereby allowing it to be processed following its excision and providing a correlation with RFP expression (FIG. 1A). For these studies, miR-93—a highly ubiquitous miRNA whose endogenous targets remain to be determined—and miR-124—a tissue specific miRNA involved in promoting neuronal differentiation—were chosen. Makeyev et al., Molecular Cell 27(3):435 (2007).

Figures 1C, 1D:
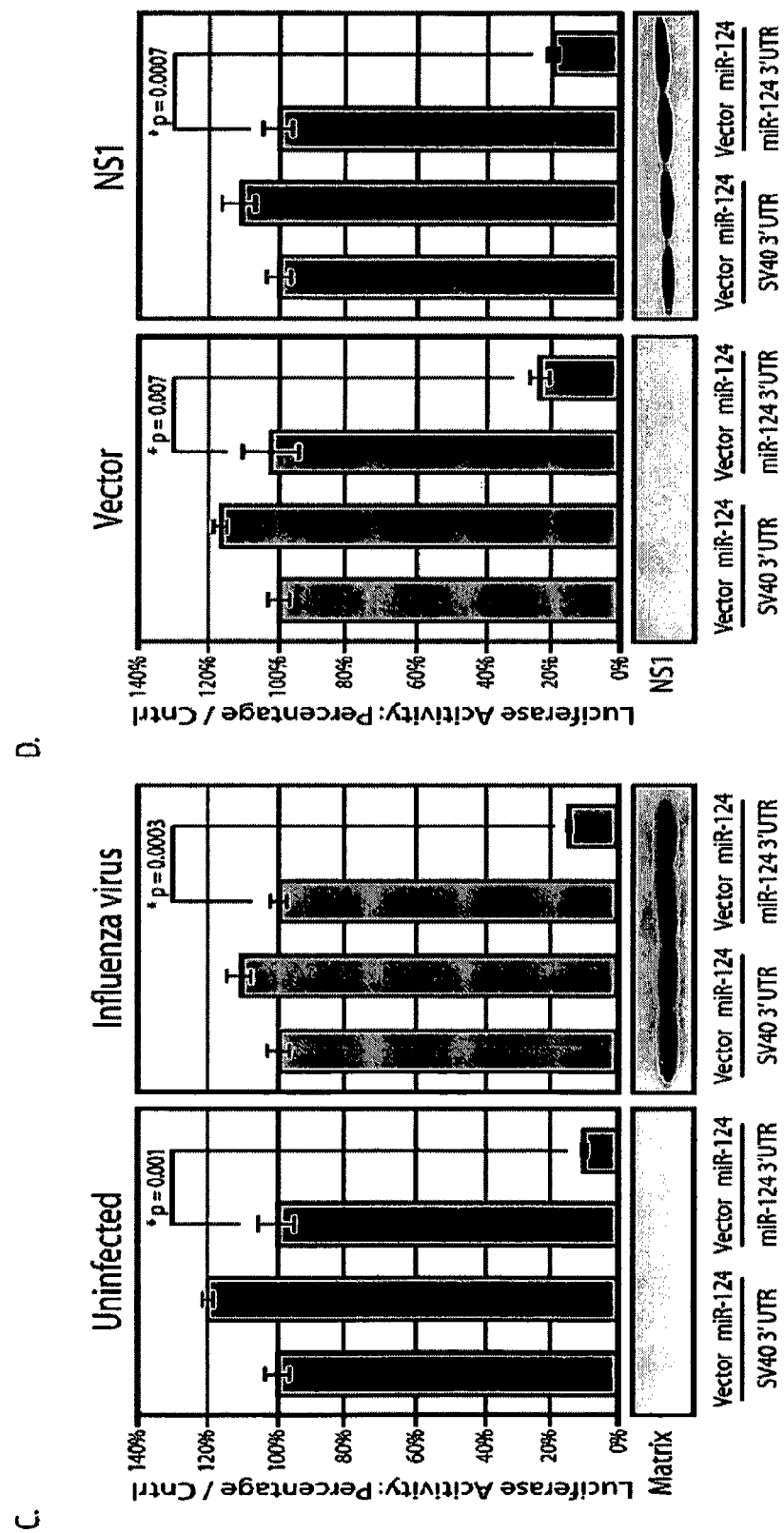

Expression of pRFP-miR-93 or pRFP-miR-124 resulted in the appearance of both pre-miRNA products as well as an increase in their mature forms (FIG. 1B). These results suggested that miRNA processing was not significantly affected during in vivo influenza virus infection. To investigate whether miRNA-mediated post-transcriptional gene silencing (PTGS) was affected during influenza virus infection, miR-124-mediated PTGS of a luciferase reporter containing known miR-124 target sequences was monitored. Makeyev et al., Molecular Cell 27(3):435 (2007). Although miR-124 failed to repress luciferase activity derived from mRNA containing a control SV40 3' UTR, it did inhibit 90% of the activity from mRNA containing the miR-124 MREs (FIG. 1C). Furthermore, this activity was not inhibited in the presence of influenza virus (A/Puerto Rico/8/34) or as a result of NS1 expression (FIG. 1C/D)—the non-structural RNA-binding protein responsible for host defense shut-off. Lu et al., Genes & Development 8(15):1817 (1994); Talon et al., Proc. Natl. Acad. Sci. U.S.A. 97(8):4309 (2000); and Jackson et al., Proc. Natl. Acad. Sci. U.S.A. 105(11):4381 (2008). These data suggested that influenza virus infection permitted miRNA biogenesis and PTGS, thereby permitting the use of MRE incorporation as a tool to induce attenuation.

Example 13

Incorporation of miRNA Target Sequences into an Influenza NP Coding Region

Figures 2A, 2B:
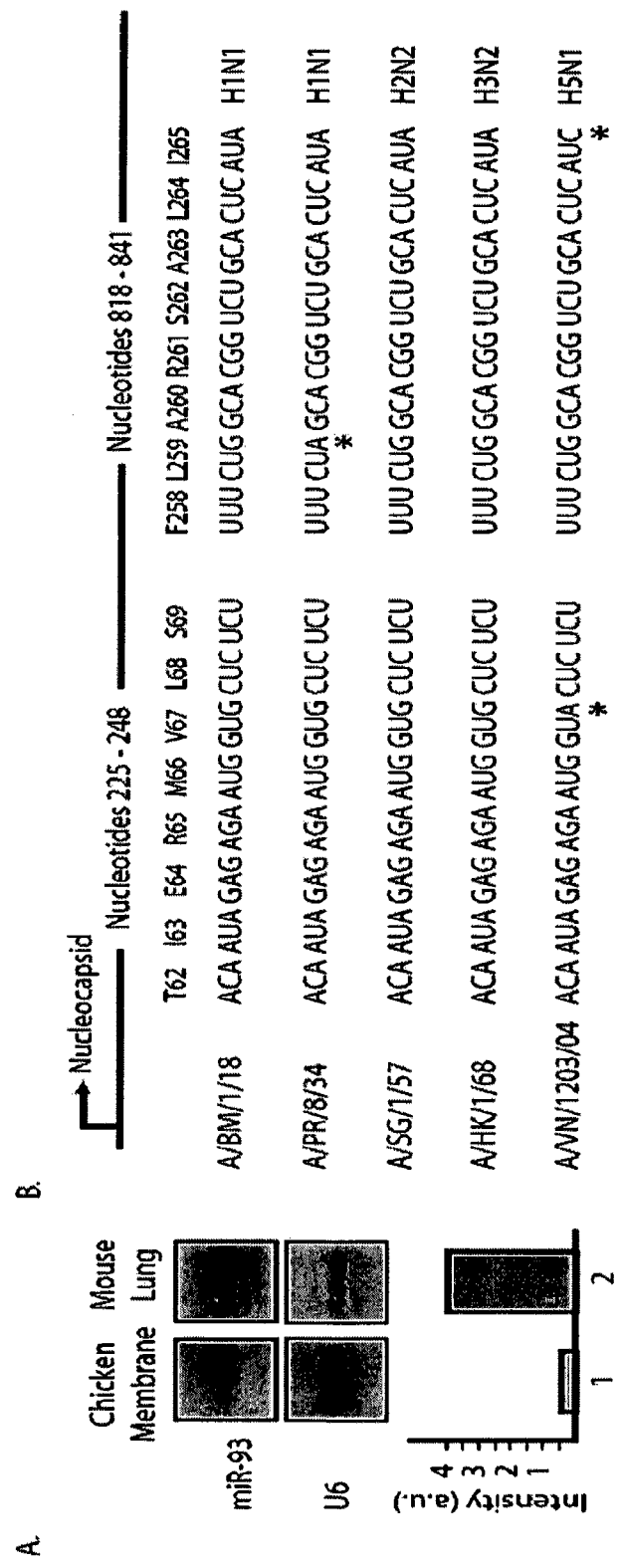
FIG. 2. (A) Top: Northern blot from 10-day old embryonated chicken egg membrane and primary murine lung tissue. Probes for miR-93 and the U6 snRNA loading control are depicted. Graph below shows quantification of the corresponding band intensities performed by detecting chemiluminescence with a CCD camera and represented as arbitrary units (a.u.). (B) Schematic of influenza virus nucleocapsid (NP) mRNA sites for the incorporation of miR-93 response elements and the overall conservation in influenza viral strains. Single synonymous mutations are indicated by "*". Nucleic acid sequences appear in two columns; in the left column (under nucleotides 225-248), the sequences shown, from top to bottom, have the following sequence identifiers: the first four sequences (A/BM/1/18, A/PR/8/34, A/SG/1/57 and A/HK/1/68) correspond to SEQ ID NO:12, and the last sequence (A/VN/1203/04) corresponds to SEQ ID NO: 174; in the right column (under nucleotides 818-841), the nucleic acid sequences for A/BM/1/18, A/PR/8/34, A/SG/1/57, A/HK/1/68, and A/VN/1203/04 correspond to SEQ ID NOs 175, 14, 175, 175 and 176, respectively. (C) Schematic of RNA base substitutions generated to transform site 1 and site 2 in non-responsive parental (PRNTL) or miR-93-responsive (93NP1/2) sites ("*" denotes amino acid substitutions). Five nucleic acid sequences are shown under "Site 1" column on the left, these sequences correspond, from top to bottom, to the following sequence identifier nos: SEQ ID NOs: 12, 139, 7, 13, and 7; five nucleic acid sequences are shown under "Site 2" column on the right, these sequences correspond, from top to bottom, to the following sequence identifiers: SEQ ID NOs: 14, 177, 7, 178 and 7. (D) Influenza virus polymerase-based luciferase reporter assay in the context of no nucleocapsid (−), wild type NP (WT), or PRNTL NP (PRNTL). Luciferase activity was measured 24 hrs post-transfection and was normalized to a *Renilla* control vector. Data are the means of three independent transfections, each done in triplicate, error bars represent +/−SD. (E) Viral titers from PRNTL and MRE-containing influenza virus infections of 10-day old embryonated eggs. Titers determined by hemagglutination and plaque assay from allantoic fluid 2 days post infection and expressed as plaque forming units per milliliter (pfu/mL). Data are the means of two independent infections.
Figure 5:
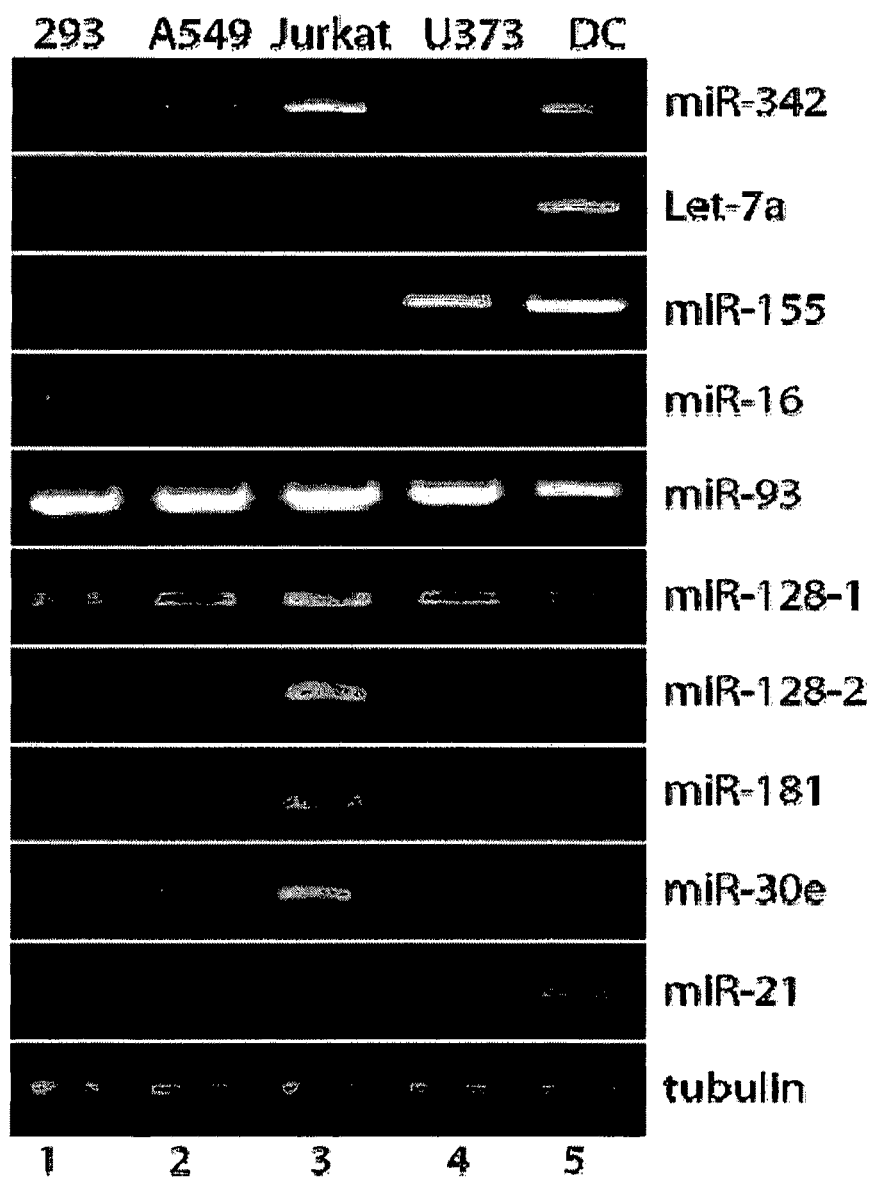
FIG. 5. RT-PCR of human miRNA-containing transcripts. Unstimulated total cellular RNA derived from embryonic kidney (HEK-293), lung epithelial (A549), T lymphocyte (Jurkat), and astrocyte (U373) cell lines as well as primary dendritic cells (DC). miRNA expression determined by PCR amplification. Tubulin is shown as an RNA loading control.
Figure 6:
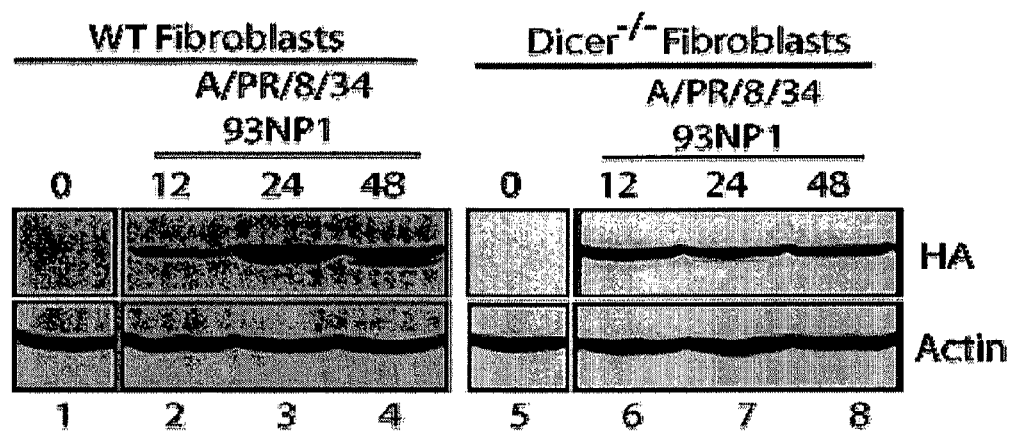
FIG. 6. Western blot of influenza A/Puerto Rico/8/1934 (93NP1) infection in wild type (WT) and Dicer−/− murine fibroblasts. Immunoblots depict hemagglutinin (HA) and Actin protein levels.

Influenza virus is traditionally propagated to high titers in the Chorioallantoic membrane of embryonated chicken eggs. Thus, for the purposes of the present invention, miRNA species were identified that were not expressed in this membrane but were ubiquitous in both murine and human lung tissue. Using in silico screens of publicly available miRNA profiles, as well as published reports of miRNAs expressed in *Gallus gallus*, miR-93 was identified as a strong candidate (FIG. 5 and Burnside et al., BMC Genomics 9:185 (2008)). These data were corroborated by Northern blot analysis (FIG. 2A).

In order to incorporate miR-93 sites into influenza virus, regions in the viral genome were identified that maintained high conservation between circulating strains. As influenza virus transcripts do not encode sufficient 3' UTRs and demonstrate packaging defects with the addition of exogenous RNA, the miRNA targets were incorporated directly into the coding region of NP. The coding region of NP was chosen because this segment demonstrated little genetic drift between strains dating from 1918 to present day, making the emergence of escape mutants unlikely (FIG. 2B).

Sequence scanning for miR-93-like sites was performed using an RNA folding algorithm, which led to the identification of two stretches of RNA that could be transformed into miR-93 target sites without the need for structural substitutions to the overall protein. To ensure efficient and effective targeting, as well as to decrease the possibility of escape mutants, two near-perfect complementary MREs were designed at positions 225 (site one) and 818 (site two) of segment five. Site one replaced the sequence: 5'-ACAAUA-GAGAGAAUGGUG CUCUCU-3' (SEQ ID NO: 12) to 5'-ACACUUGAACGAAUGGUACUUUCU-3 (SEQ ID NO: 13) (herein referred to as 93NP1) or 5'-ACCUUA-GAGAGGAUGGUCCUAUCU-3' (SEQ ID NO: 139) (herein referred to as PRNTL1). Site two replaced the sequence: 5'-UUUCUAGC ACGGUCUGCACUCAUA-3' (SEQ ID NO: 14) to 5'-UUCCUUGCACGGACAGCACU UUUA-3' (SEQ ID NO: 15) (herein referred to as 93NP2) or 5'-UUUCUAGCCAGAA CUGCACUCUUA-3' (SEQ ID NO: 140) (herein referred to as PRNTL2).

Figure 2C:
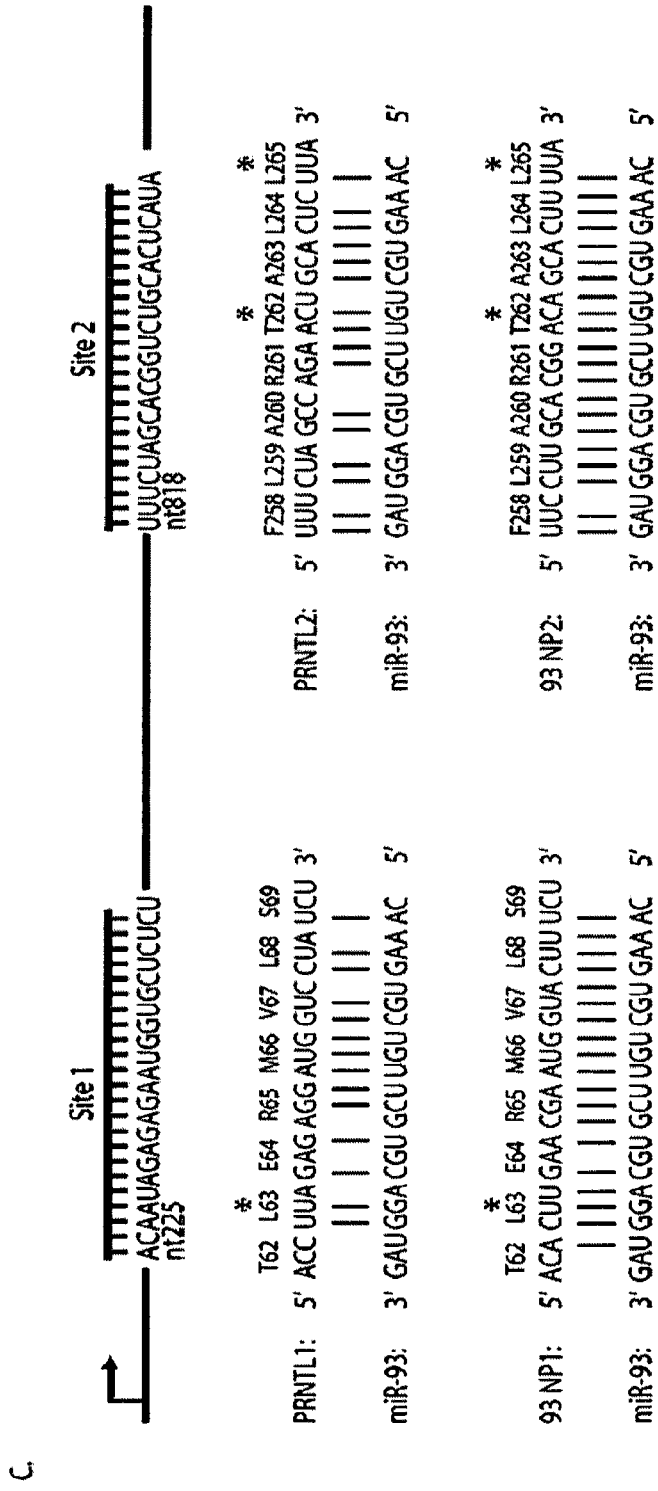
Figure 2E:
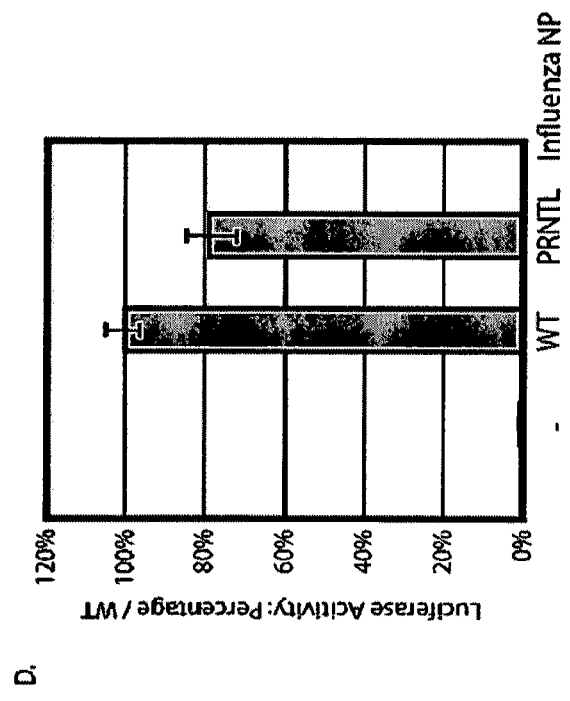
Figure 2D:
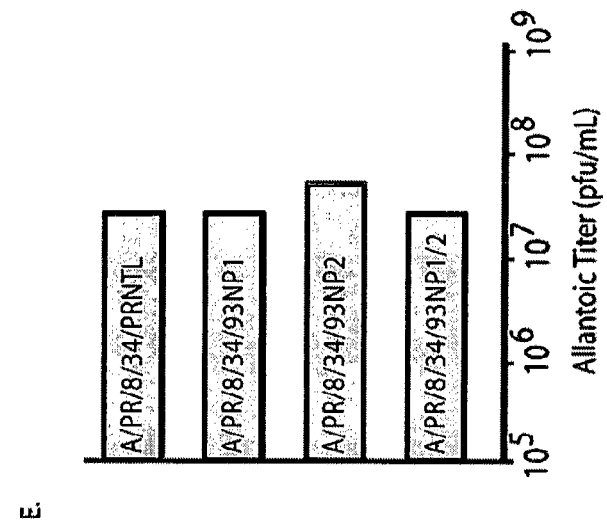

The calculated mean free energy (MFE) of sites one and two were −28 and −37.1 kcal/mol, respectively (FIG. 2C). Generating miR-93 sites resulted in three amino acid substitutions, all of which remained within their hierarchical order. Thus, it was first determined whether NP function was compromised. For this, an antisense reporter construct encoding an influenza virus polymerase site was transfected with the necessary RNA-dependent RNA polymerase (RdRp) components PB1, PB2, PA, and either wild-type or the parental NP constructs. Pleschka et al., J. Virol. 70(6):4188 (1996) and Hoffmann et al., Antiviral Research 80(2):124 (2008). These data demonstrated that incorporation of 163L, S262T, and/or I265L into NP did not affect overall function of the protein, although it did result in an approximate 20% decrease in polymerase activity (FIG. 2D).

Following verification of NP functionality, human embryonic kidney cells were transfected with the various MRE-containing NP segments alongside plasmids encoding the remaining seven influenza viral segments (A/Puerto Rico/8/34) transcribed bidirectionally by RNA polymerase I and II, thereby simultaneously generating viral RNA (vRNA) and mRNA. Quinlivan et al., J. Virol. 79(13):8431 (2005) and Park et al., Proc. Natl. Acad. Sci. U.S.A. 103(21):8203 (2006). Cells were harvested 24 hours post transfection and were injected into 10-day old embryonated chicken eggs. All influenza virus strains (PRNTL, miR-93NP1, miR-93NP2, and miR-93NP1/2) were rescued with equal efficiency, demonstrating no attenuation in ovo, generating titers greater than $1 \times 10^7$ plaque forming units per milliliter (pfu/mL) (FIG. 2E).

Example 14

Figure 3A:
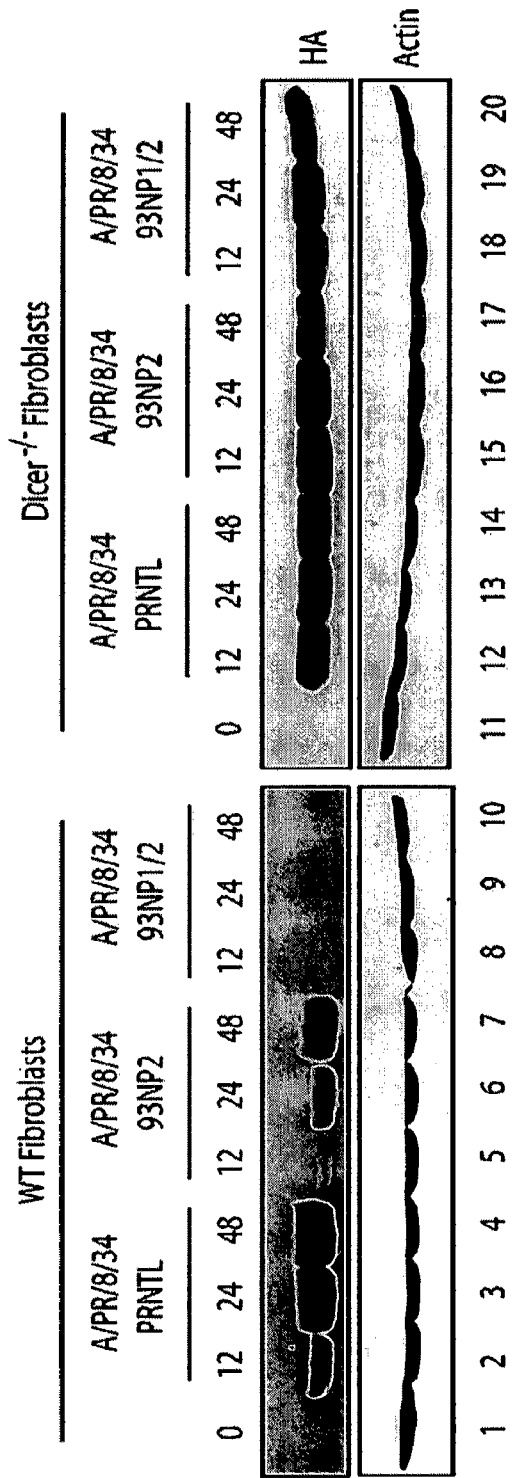
FIG. 3. (A) Western blot of influenza A/Puerto Rico/8/1934 (A/PR/8/34) PRNTL, 93NP2, and 93NP1/2 infections harvested at 12, 24, and 48 hrs post-infection (hpi) in wild-type (WT) and Dicer−/− murine fibroblasts. Immunoblots of hemagglutinin (HA) and Actin protein levels are shown. (B) Northern blot from unstimulated WT and Dicer−/− fibroblasts. Probes for miR-93 and U6 snRNA are depicted. Graph below shows quantification of the corresponding band intensities as a measure of miR-93 over control U6 snRNA intensity expressed in arbitrary units (a.u.). (C) RT-PCR analysis of infected murine lung five days post-infection (dpi). Viruses include PRNTL, 93NP1, 93NP2, and 93NP112. Primers specific for Interferon Regulatory Factor 7 (IRF7), Interferon beta (IFNβ), Interleukin 6 (IL6), and Hypoxanthine-guanine phosphoribosyltransferase (HPRT) are shown. (D) Western blot of murine infections as described in (C) depicting IRF1, STAT1, Interferon Stimulated Gene 54 (ISG54), and Actin protein levels. (E) Representative sequences of influenza virus NP clones isolated following multiple passages ex vivo or five days post-infection in vivo. Nucleic acid sequences appear in two columns, under "Site 1" on the left, and "Site 2" on the right. The first three sequences (from the top) under Site 1 correspond to SEQ ID NO: 139, and the last four sequences under Site 1 correspond to SEQ ID NO: 13. The first three sequences (from the top) under Site 2 correspond to SEQ ID NO: 177, and the last eight sequences under Site 2 correspond to SEQ ID NO: 178.

Ex Vivo and In Vivo Attenuation of Influenza A Viruses Containing MRE-Containing NP Segments To determine if incorporation of MRE-containing NP segments resulted in miR-93-mediated attenuation, wild-type and Dicer−/− murine fibroblasts were infected with parental A/Puerto Rico/8/34 (PRNTL), A/Puerto Rico/8/34/93NP1 (93NP1), 93NP2, or 93NP1/2 (FIGS. 3A and S2). At a multiplicity of infection (MOI) of 1.0, PRNTL virus produced abundant levels of hemagglutinin (HA) in wild-type fibroblasts at 12 hours post-infection (hpi). This rate of viral transcription showed a mild attenuation with the incorporation of a single MRE, whereas 93NP1/2 demonstrated a complete loss of protein production (FIG. 3A). This attenuation could be attributed to the incorporated MRE sites as these same viral strains replicated to high titers in the absence of Dicer, which prevented miRNA processing (FIGS. 3A and B). These data demonstrated that incorporation of MREs into influenza viral transcripts induced miRNA-mediated attenuation ex vivo.

Figure 3D:
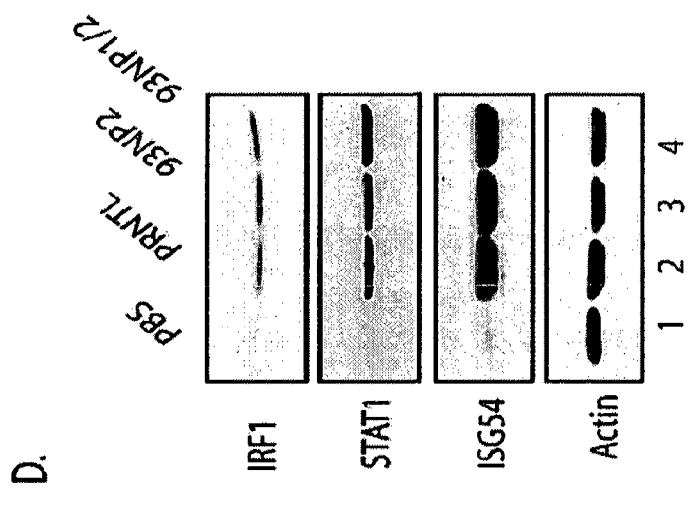
Figure 3C:
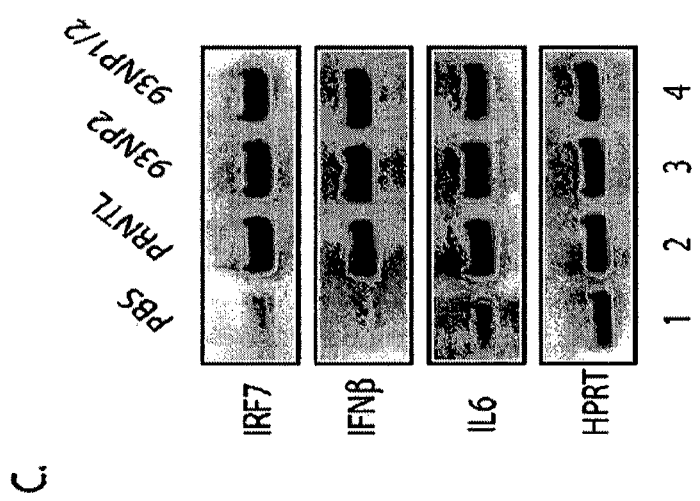
Figure 3B:
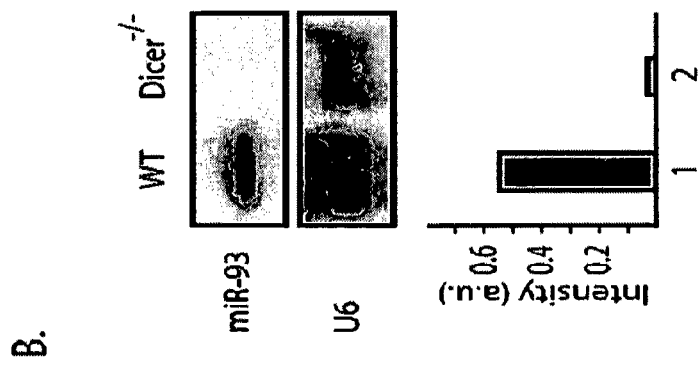
Figure 7:
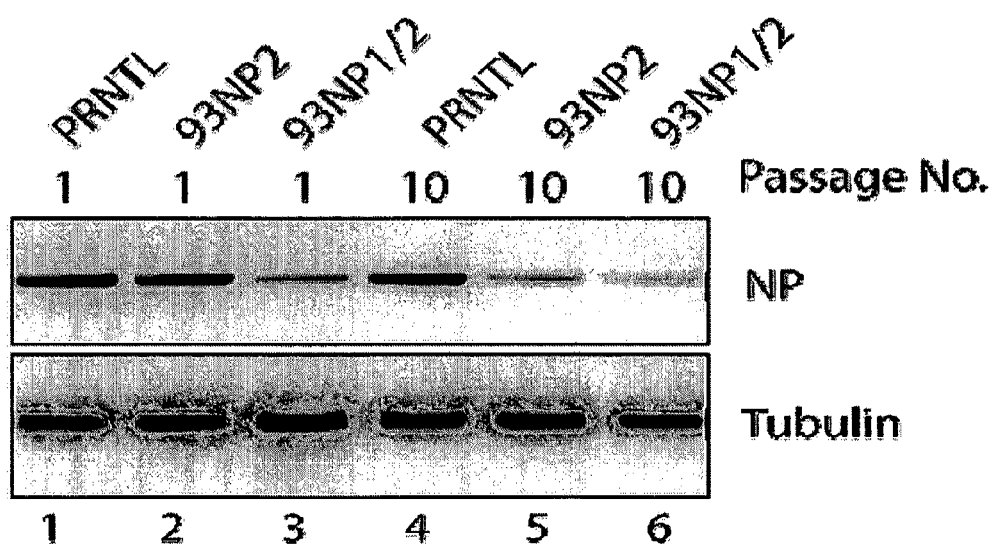
FIG. 7. RT-PCR of influenza virus nucleocapsid (NP) and tubulin transcripts from A549 lung epithelial cells. A/Puerto Rico/8/1934 (PRNTL), (93NP2), and (93NP1/2) were used to infect at a low MOI and were passaged as indicated. Total RNA from infected cells at the time of harvest was amplified by RT-PCR with a high fidelity polymerase and resolved on 2% agarose.

To characterize the MRE-containing influenza strains in vivo, mice were infected intranasally with $10^4$ pfu and harvested total lung extract at 5 days post-infection (dpi). RT-PCR analysis of the cardiac lobe demonstrated no discernable difference between the immune response to PRNTL and MRE-containing strains. In response to each individual strain, there was robust upregulation of Interferon Regulatory Factor 7 (IRF7) mRNA and the induction of key antiviral cytokines including Interferon beta (IFNβ) and Interleukin 6 (IL6) (FIG. 3C). Furthermore, protein analysis of the left lobe also demonstrated robust induction of both IFNβ- and IFNγ-regulated genes such as STAT1, IRF1, and IFN stimulated gene 54 (ISG54) (FIG. 3D). In addition, as influenza virus has a high propensity to mutate (tenOever et al., Science 315 (5816):1274 (2007)), a multi-cycle infection was performed ex vivo in human lung epithelial cells A549 (ATCC Catalog No. CCL-185) and in vivo in mice, harvesting RNA after several serial passages or 5 dpi, respectively (FIGS. 3E and 7). Surprisingly, both in vivo and ex vivo infections yielded no revertants, suggesting that the flexible nature of miRNA targeting, combined with the opposing rigid conservation of NP, prevents the generation of escape mutants.

Example 15

In Vivo Protection with MRE-Containing Influenza A Virus Vaccines

To determine whether miRNA-mediated attenuation ex vivo could be demonstrated in vivo and used as a successful vaccine, pathogenesis studies were performed in mice. To illustrate the versatility of this potential vaccine strategy, the MRE-containing segment five of A/Puerto Rico/8/34 (H1N1) was used to rescue a chimeric strain containing avian hemagglutinin (H5) and neuraminidase (N1) from A/Vietnam/1203/04 through standard reverse genetics. Park et al., Proc. Natl. Acad. Sci. U.S.A. 103(21):8203 (2006) and Tumpey et al., Science 310(5745):77 (2005).

To elucidate whether our H5N1 MRE-containing viral strain was attenuated in vivo, mice were infected with increasing concentrations of either H5N1 PRNTL or H5N1 93NP1/2. At viral titers of $10^5$, the PRNTL strain of influenza resulted in 3/3 deaths as compared to only a single mortality for the MRE-containing strain (FIG. 4A). Furthermore, mortality was limited to infections with the PRNTL strain at intranasal inocula of $10^4$ and $10^3$ (n=8/cohort), with a calculated 50% lethal dose that was approximately three logs higher than the MRE-containing strain (FIG. 4A). Weight loss occurred in response to MRE-containing H5N1, like the parental strain; however, miR-93NP1/2 virus was neutralized thereafter and mice showed complete recovery (FIG. 4B).

Figure 4D:
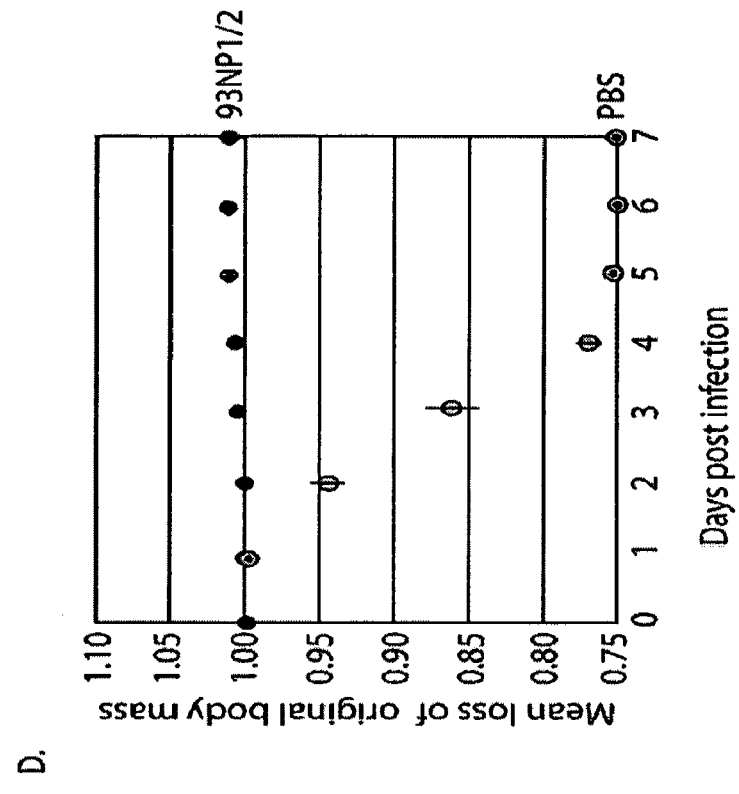
FIG. 4. (A) Graphic representation of percent survival following intranasal challenge with PRNTL or MRE-containing (93NP1/2) H5N1 chimeric viruses over a time course of ten days. Data represents the mean of each inoculating dose and virus treatment (n=4/cohort) (B) Morbidity expressed as average mean loss of original weight from mice described in (A) at an inoculating dose of 1×10$^4$ plaque forming units (pfu)/infection. (C) Graphic representation depicting percent survival following vaccination and secondary lethal challenge of chimeric H5N1 influenza virus. Data from the unchallenged cohorts (n=2/treatment) and the H5N1 challenge (n=7/treatment) is represented as mean survival. (D) Morbidity expressed as average mean loss of original weight from mice vaccinated with PBS or 93NP1/2 and subsequently rechallenged with 1×10$^6$ pfu PRNTL H5N1 per animal. Data represents mean weight loss among cohorts described in (C). Error bars represent +/−SD of the mean.
Figure 4C:
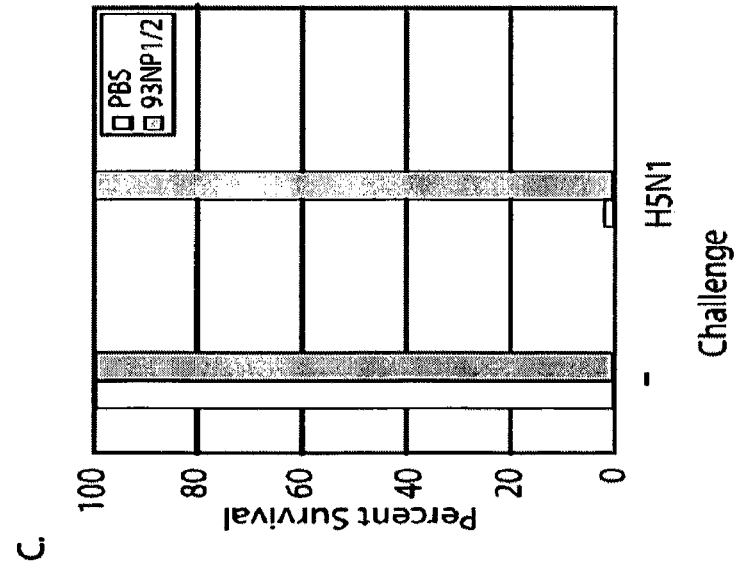

These data suggest that the in vivo attenuation of MRE-containing influenza virus still permits a low-grade level of replication, thus demanding an adaptive immune response. This implies that MRE-containing influenza virus strains would generate very high levels of neutralizing antibodies and would therefore serve as excellent vaccine candidates. To test this hypothesis, mice were re-challenged 21 days post infection with the parental H5N1 strain at ten times the lethal dose ($10^6$ pfu/mouse) and again monitored for survival (FIG. 4C). In comparison with mock vaccination, where 100% mortality and rapid weight loss was observed (FIGS. 4C and 4D), MRE-containing H5N1-innoculated mice displayed no signs of morbidity, indicating complete protection and the presence of neutralizing antibodies (FIGS. 4C and 4D).

Example 16

Immunological Assessment of Recombinant Viruses

Figure 8A:
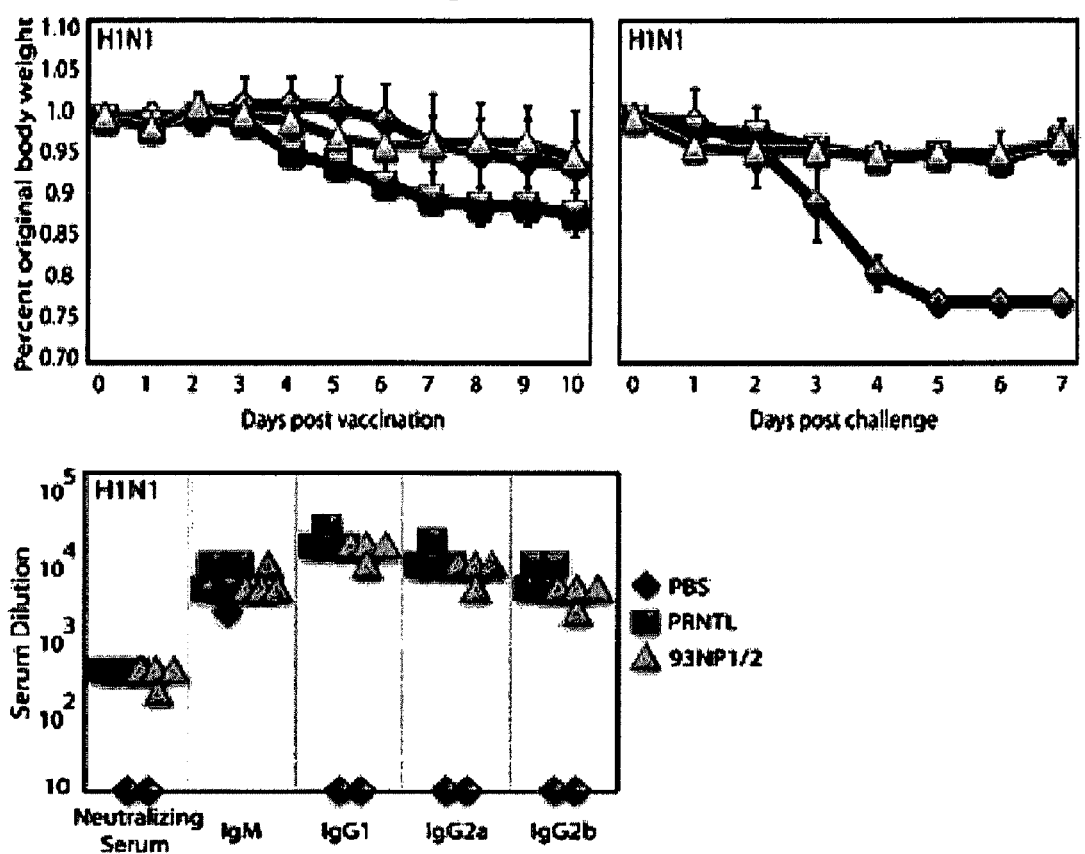
Figures 8B, 8C:
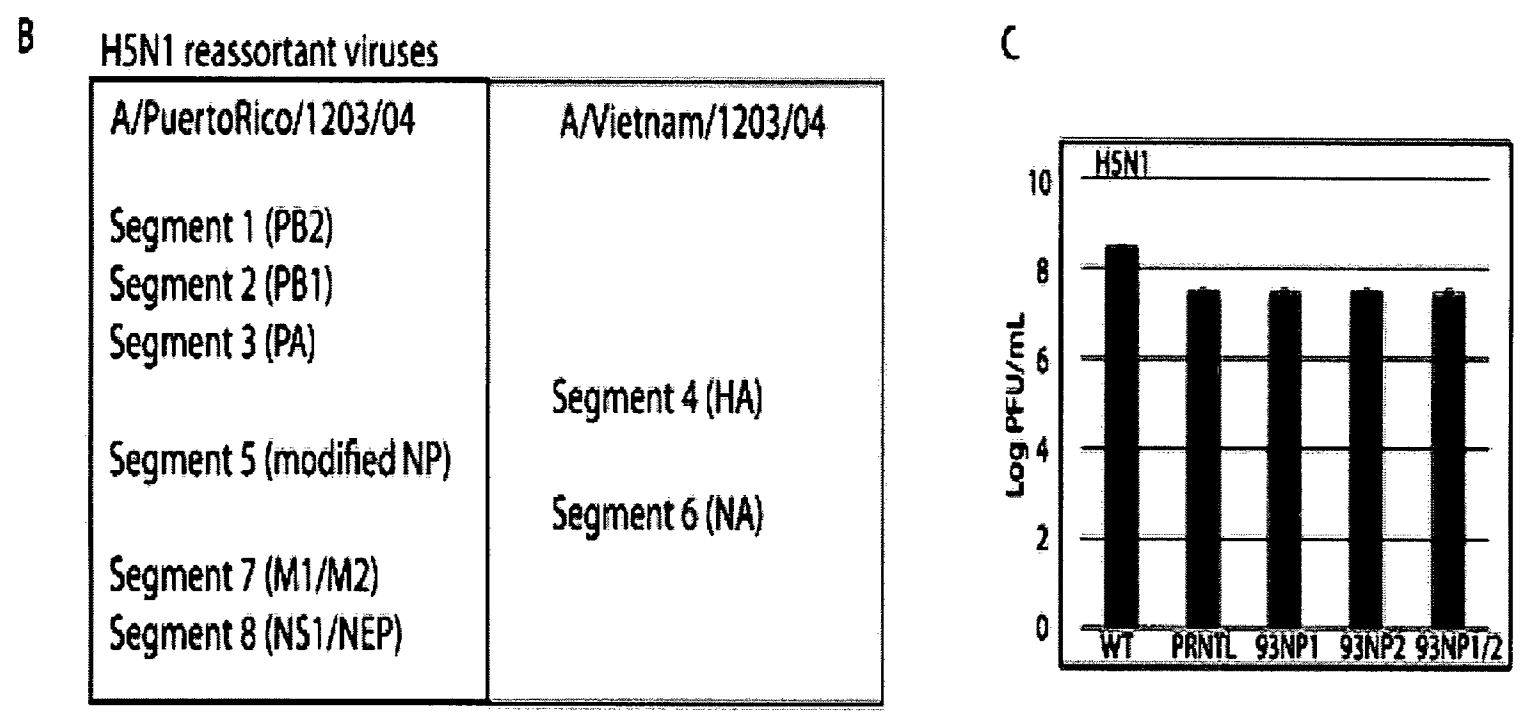
Figure 8D:
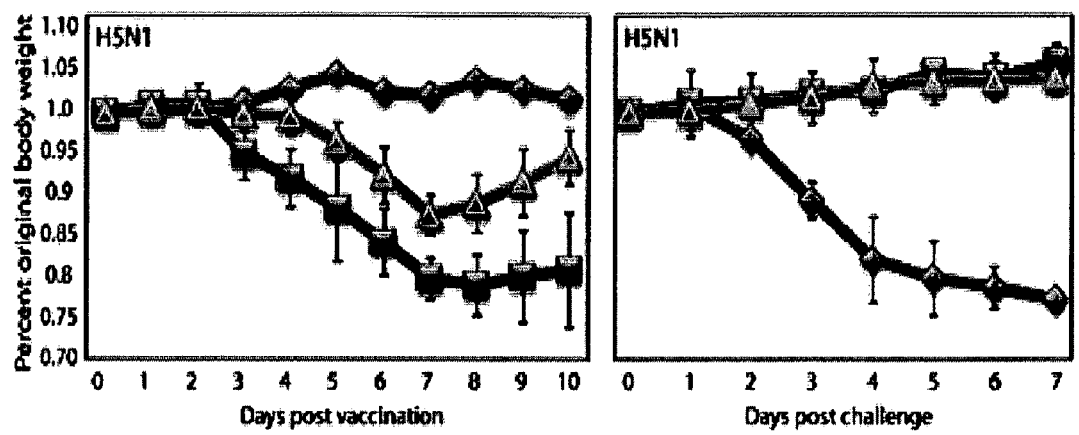
Figure 8D:
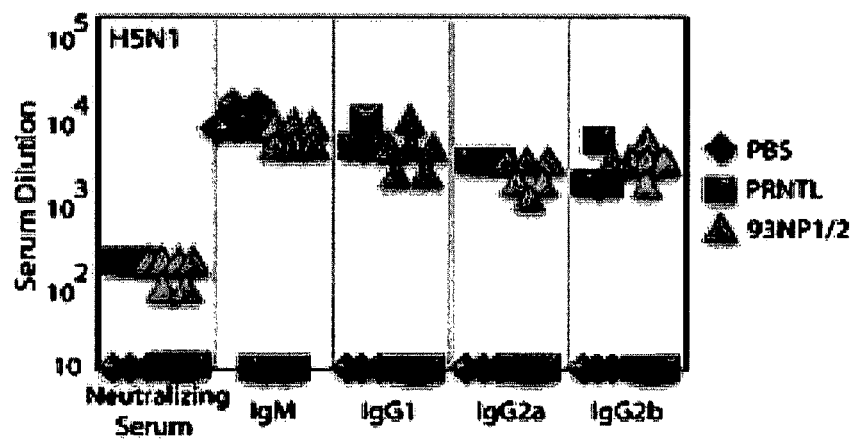

To ascertain whether miR-93 targeted strains would induce a neutralizing and robust immune response, studies in mice were performed with the A/PR/8/34 H1N1 PRNTL and 93NP1/2 recombinants (FIG. 8A). Inoculation of the PRNTL strain resulted in greater than 10% weight loss as compared to 93NP1/2 or PBS administration. Furthermore, a lethal challenge of these mice, 21 days post vaccination, resulted in 100% survival and a robust repertoire of neutralizing antibodies including: IgM, IgG1, IgG2a, and IgG2b (FIG. 8A). To expand on the utilization of species-specific, miRNA-mediated vaccine development, a miR-93 targeted H5N1 reassortant virus was further tested. For this, the MRE-seeded NP segment (described in Perez et al. Nature Biotechnology 27(6) 572 (2009)) and wild type segment 1-3 and 7-8 of A/PR/8/34 (Accession numbers AF389115.1 AF389116.1 AF389117.1 AF389121.1 AF389122.1), were utilized to rescue H5N1 6:2 reassortants, generating viruses antigenically recognized as A/Vietnam/1203/04/H5N1 (described in Perez et al. Nature Biotechnology 27(6) 572 (2009)) via HA and NA gene expression (FIG. 8B). Genetic rescue and propagation of these viruses demonstrated no attenuation in ovo (FIG. 8C). Unlike the H1N1 vaccinations, administration of H5N1 PRNTL resulted in 50% mortality and an average 20% loss in body weight. In contrast, MRE-seeded H5N1 demonstrated complete survival, but induced a mild loss in body weight (FIG. 8D). Subsequent to vaccination, mice were challenged 21 days post infection with a lethal dose of H5N1. In comparison with mock vaccination, where 100% mortality and rapid weight loss were observed, MRE-seeded H5N1-inoculated mice displayed no signs of morbidity, indicating complete protection (FIG. 8D). Furthermore, serum from these mice were also positive for neutralizing activity against wild type H5N1 virus and, like H1N1 vaccinations, generated high titers of IgM, IgG1, IgG2a, and IgG2b (FIG. 8D).

Example 17

Generation of an Additional Recombinant Virus

Figure 9:
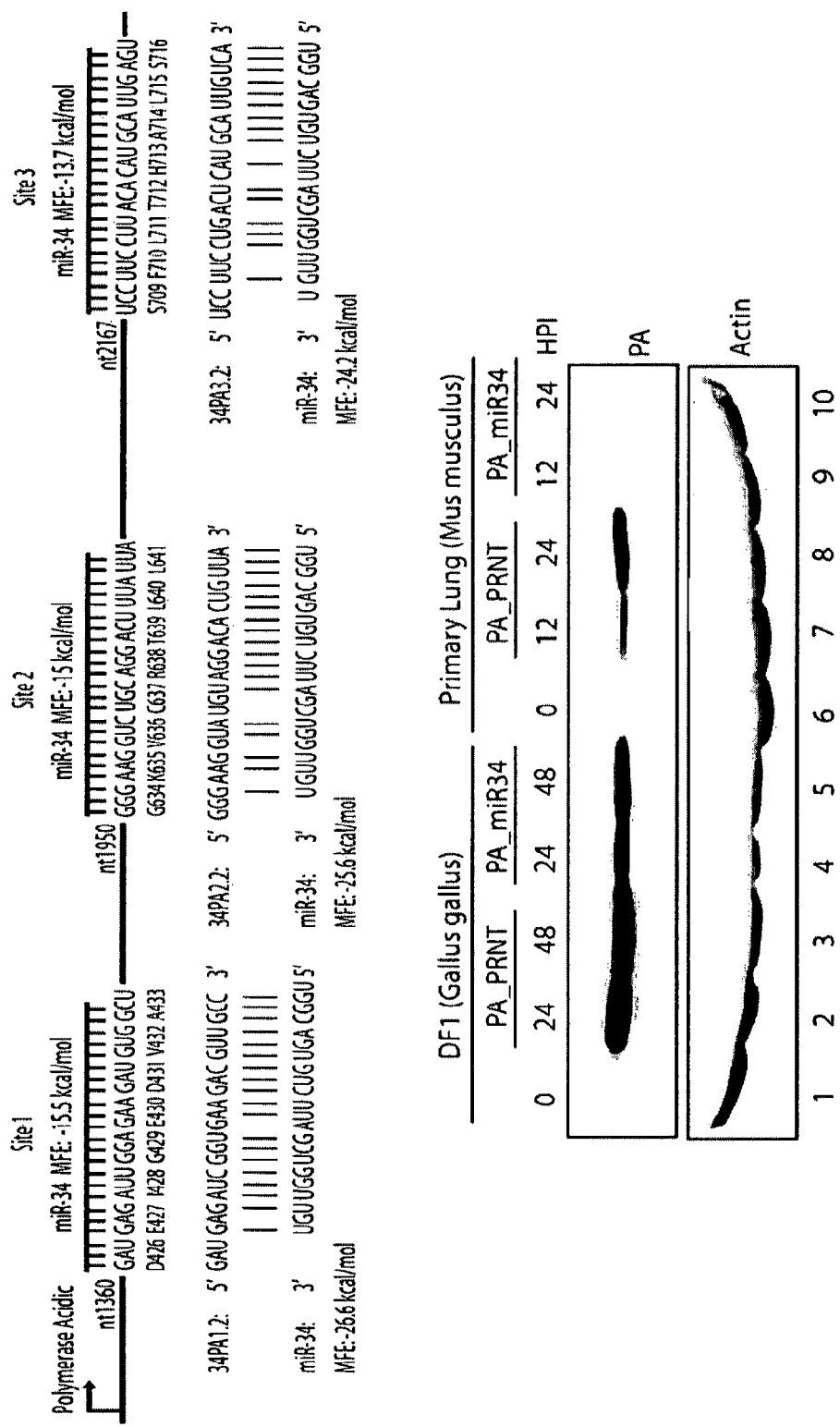
FIG. 9. Design strategy for species-specific attenuation. Schematic of RNA base substitutions generated to transform site one, two, and three into miR-34-targeted PA. miR-34 is a mammalian specific miRNA. Mean free energy is included as kcal/mol for each respective site. Virus was rescued in eggs and used to infect DF1 chicken (Gallus gallus) fibroblasts or mouse (Mus musculus) primary lung fibroblasts at the time points indicated (HPI: hours post infection). PA_PRNT is wild type virus not targeted by miR-34, PA_miR34 is the virus in which PA is targeted at the three sites indicated. Nucleic acid sequences are shown in three columns, under "Site 1", "Site 2" and "Site 3." The sequences under Site 1 correspond, from top to bottom, to SEQ ID NOs: 179, 180 and 5. The sequences under Site 2 correspond, from top to bottom, to SEQ ID NOs: 181, 182, and 5. The sequences under Site 3 correspond, from top to bottom, to SEQ ID NOs: 183, 184, and 5.

To expand on the above findings that segment 5 (encoding NP) can be targeted by the mammalian-specific miR-93, a second species-specific, MRE-targeted influenza A virus strain was designed that exploited a different mammalian specific miRNA and targeted a different influenza A segment. Specifically, using the general template and approach described above, three near-perfect miR-34 target sites were incorporated into the open reading frame of PA (encoded on segment 3). Incorporation of miR-34 target sites were generated by standard site-directed mutatgenesis (as described in Kunkel, Proc. Natl. Acad. Sci. USA 82: 488-492 (1985), U.S. Pat. No. 5,071,743). Primers for site directed mutagenesis included complementary sets of 5-GATTGGAGAAGAcGT-tGCcCCAATTGAACAC-3' (SEQ ID NO: 148) and 5'-AGCTTGATGAGATcGGtGAAGACGTTGCC-3' (SEQ ID NO: 149) for site one; 5'-GGAAGGTCTGCAGGACacT-gTTAGCAAAGT-3' (SEQ ID NO: 150) and 5'-GAAAGT-TCCATTGGcAAGGTaTGtAGGACACT-3' (SEQ ID NO: 151) for site two, and 5'-CCTTACACATGCATTGtcaTAGT-TGTGGCAG-3' (SEQ ID NO: 152) and 5'-ACTCCTTCCT-gACtCATGCAcTGTCATAGTT-3' (SEQ ID NO: 153) for site three (with the non capitalized bases representing the base changes made at each step to generate miR-34 MREs). As miR-34, like miR-93, is absent in chicken cells (Table 10), rescue of this virus demonstrated no attenuation when propagated in DF1 chicken fibroblasts (FIG. 9). In contrast, this same virus, when passaged in cells derived from mouse lung, showed a robust attenuation at both 12 and 24 hours post infection (hpi).

Example 18

Generation of a Tissue/Cell-Specific Recombinant Virus

Figure 10A:
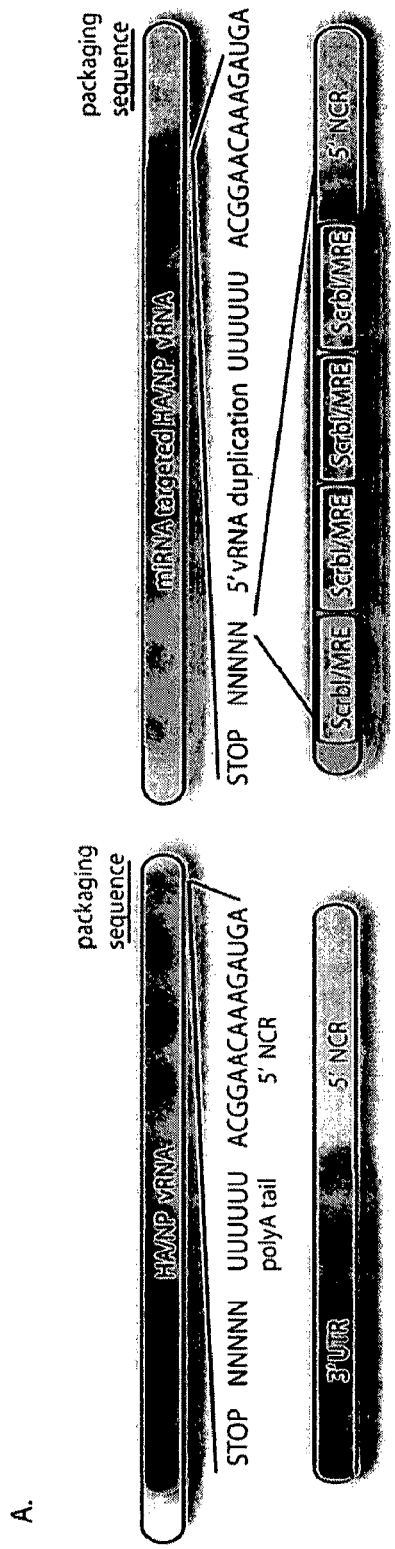
FIGS. 10A-F. (A) A schematic drawing showing influenza A virus untranslated region (UTR) targeting in tissue culture. To expand the mRNA 3' UTR without disrupting the packaging sequence (drawn to scale above vRNA cartoon), the last 80-120 base pairs were duplicated allowing for the insertion of scrambled (scrbl) or miRNA-targeted elements (MRE) between the stop codon (STOP) and the polyA tail (UUU-UUU) (SEQ ID NO: 185). NCR depicts non-coding region of the viral RNA and the sequence shown corresponds to SEQ ID NO: 186 in the schematic drawings on both the left and right sides of the figure. (B) Schematic drawing of the red fluorescent protein minigene containing a single intron (pRFP) used for the exogenous delivery of miRNAs. (C) Northern blot of miR-142 from fibroblasts (MDCK cells), transfected fibroblasts (MDCK cells transfected with pRFP-miR-142) and primary murine macrophages. (D) Northern blot of miR-142 in MDCK cells. (E) Western blots depicting expression of influenza A/PR/8/34 NP, M1, and active from mock infection or viruses encoding an NP with a scrambled 3' UTR (NP UTR) or a UTR encoding miR-142 responsive elements (NP_142). Protein extracts were harvested 12 hours post infection (MOI 1) from MDCK control cells or MDCK cells expressing miR-142 (MDCK_142). (F) Western blots of matrix (M1), NS1 and actin from primary lung fibroblasts or macrophages (produced using an adapted protocol to that described in Zhu et al., Nature Protocols, 2010, 5(3):550) infected with control virus (NS1_UTR) or miR-93 targeted NS1 virus at the time points indicated. Viruses used include NS1_UTR and miR-142-targeted NS1 (NS1_142).
Figure 10B:
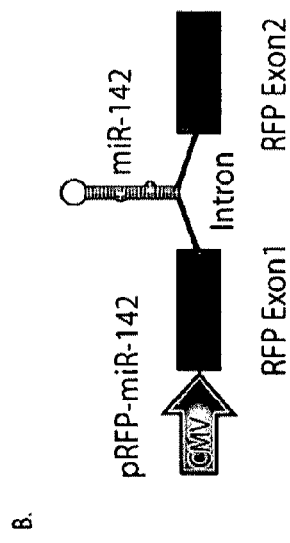
Figure 10C:
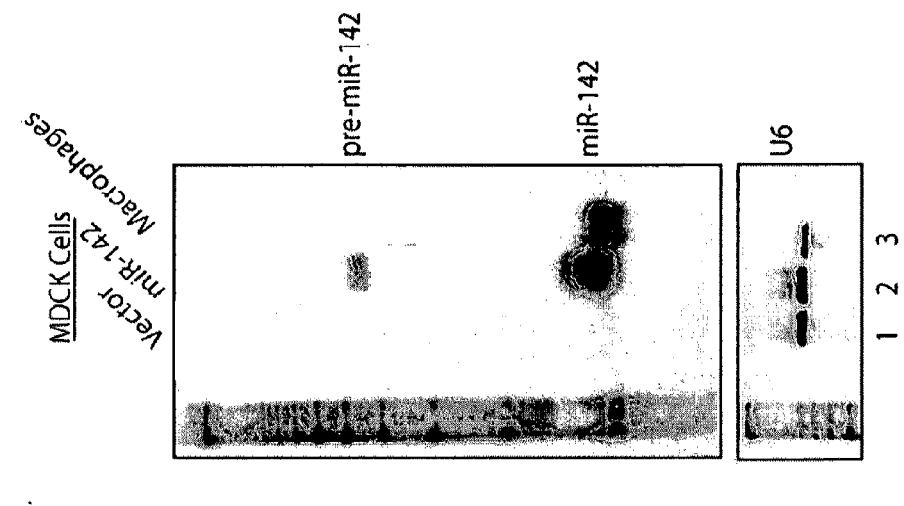
Figure 10D:
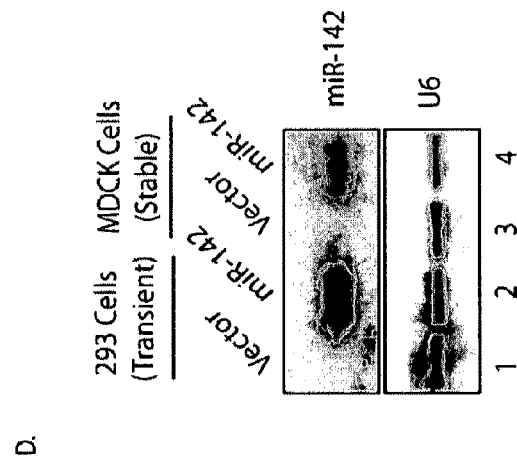
Figures 10E, 10F:
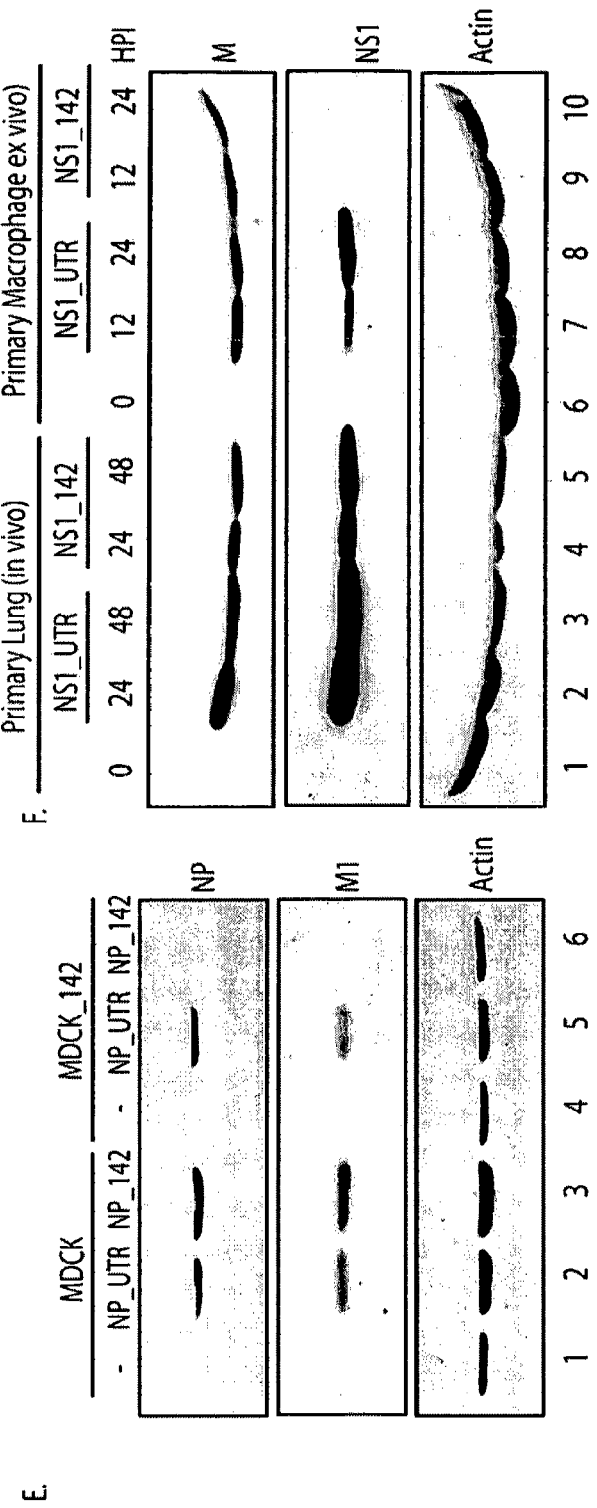

To expand on both the targeting strategy (open reading frame (ORF) versus untranslated region (UTR)) and to ascertain whether MRE-mediated attenuation could be adapted to tissue/cell culture systems for large-scale influenza production, NS1 or NP influenza genes were targeted with tandem repeats of either a scrambled sequence (Scrbl) or an MRE unique to the hematopoietic cells (miR-142 [5'-UGUAGU-GUUUCCUACUUUAUGGA-3'SEQ ID NO: 141]; see Landgraf et al., Cell 129:1401 (2007)). To perform this, the 5' packaging sequence was duplicated on the viral RNA and this genetic information was inserted between the stop codon and the polyA tail sequence (FIG. 10A) To engineer viral transcripts targed by miRNA through an artificial 3'UTR, the general structure of the viral segment was manipulated to encode both a 3' UTR and contain a duplicated RNA packaging sequence. A unique Sal1 restriction site was introduced between the stop codon and the polyadenylation site of the vRNA through standard site-directed mutagenesis. Primers for the generation of an artificial NP 3'UTR included complementary sets of 5'-GTACGACAATTAAA GtcgAcTACCCTTGTTTCTAC-3' (SEQ ID NO: 154) where the undercase bases are the nucleotides that were changed and the underlined sequence is the Sal1 site. Once developed, the viral packaging sequence, previously established to be 120 base pairs for NP (Fields et al., Lippincott Williams & Wilkins, Philadelphia, Pa., 2007) was inserted. NP packaging sequence primers included 5'-CgTCGAcCTCTCGGACGAAAAGG-3 (SEQ ID NO: 155) and 5'-CTCGAGTAGAAA-CAAGGGTATTTTTCTTTAATTG-3'(SEQ ID NO: 156) which contain Sal1 and Xho1 linkers (underlined). PCR-generated product was cut with Xho1 and Sal1 and ligated into the Sal1 site, thereby generating a 3'UTR. As the Xho1 and Sal1 ligations destroy the palindromic sequence, the single remaining Sal1 site, located between the stop codon and the poly U tract (which serves to generate the polyA tail), provides an insertion point for the subsequent ligations of scrambled sequence or specific miRNA response elements (MREs) (FIG. 10). This same strategy was used to target NS1, except in this case, the duplicated region included the entire NS2 (NEP) ORF beginning with the splice acceptor site to the 5' end of the vRNA. 5'-GTCGACCTCTTCCAGGACAT-ACTGCTG-3' (SEQ ID NO: 157) and 5'-CTCGAGAGAAACAAGGGTGTTTTTTATTA-3' (SEQ ID NO: 158). The miR-142 MRE insertion oligo was four copies of the insert 5'-TCCATAAAGTAGGAAACACTACA-3' (SEQ ID NO: 159) or four copies of a scrambled untargeted sequence 5'-GATCGGTAGCTACGTAGCTAGC-3' (SEQ ID NO: 160). To test whether this targeting strategy could be applied to cell culture, a plasmid was also adapted to express exogenous miR-142 using the same strategy outlined for FIG. 1 and described in Perez et al. Nature Biotechnology 27(6) 572 (2009) (FIG. 10B). To produce miR-142, a human genomic 318 bp fragment having sequence: 5'-CCAGTGCT-GTTAGTAGTGCTTTCTACTTTATGGGT-GACTGCACTGTCTGTCTGTCC GTCGGCGTG-TACTCTTCAGGCTGCCCAGGCCTCCTGACTCCTG-CTCCAAGAGCCCCC CAGCCCTCCTTGTGGCTTC-CTAAGATCCCCCCAACCCTGCCAGGGC-CCCCCGAGGGC CCGCCCTGGGCCTTGTGGGCGGT-GACTCAGCATGGCGCCAGACTTGCCTCCTCTACC TCCCTCCCCCACTTCCTCTTCAGTTC-CCTCTTCCCTTCCCCCTAAAGGCTCCACCCCAT CCCCCCAGTTTCAGAGACACTCAGGTAGAGAC-3' (SEQ ID NO: 163) encoding the miR-142 locus was amplified with primers 5'-CCAGTGCTGTTAGTAGTGCTTTC-3' (SEQ ID NO: 161) and 5'-GTCTCTACCTGAGTGTCTCT-GAAAC-3' (SEQ ID NO: 162). This plasmid demonstrated robust expression when transfected into MDCK cells as compared to endogenous miR-142 expressed in macrophages (FIG. 10C). MDCK cells (ATCC Catalog No. CCL-34) were selected for stable plasmid expression by cell sorting for red fluorescence. Sorted MDCK cells expressing either vector alone or miR-142 were maintained and expanded as new cell lines (FIG. 10D). When virus replication of miR-142 targeted NP (FIG. 10E) was compared in vector expressing MDCK cells versus MDCK cells expressing miR-142, the miR-142 targeted NP viral strain demonstrated a dramatic attenuation in a miRNA-specific manner as opposed to the scrambled UTR control counterparts. These results were similar to those comparing miR-142 targeted NS1 where the MRE-encoding viruses was selectively attenuated in primary macrophages expressing miR-142 (FIG. 10C) but not in primary lung fibroblasts where miR-142 is absent (FIG. 10F). These results demonstrate the feasibility of adapting this MRE-based technology to cell culture and that MRE targeting can be directed against either the coding region or an artificial 3'UTR of influenza viral segments. Furthermore, these results demonstrate that MDCK cells or other cell culture lines can be exploited for virus growth by incorporating miRNAs not normally expressed in these cells.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A composition comprising a recombinant influenza virus wherein said influenza virus comprises a microRNA Response Element (MRE) sequence, wherein the MRE sequence is selected such that the mean free energy (MFE) of MRE interaction with its corresponding microRNA is less than −35 kcal/mol.

2. The composition of claim 1, wherein the influenza virus comprises one or more additional MRE sequences.

3. The composition of claim 1, wherein the MRE sequence is inserted within a coding region of one or more influenza virus genes.

4. The composition of claim 3, wherein the influenza virus gene encodes an influenza virus protein selected from the group consisting of HA, NA, PB1, PB2, PA, M1, M2, NP, NS1, and NS2/NEP.

5. The composition of claim 3, wherein the influenza virus gene encodes an influenza virus protein selected from the group consisting of PB1, PB2, PA, M1, M2, NP, NS1, and NS2/NEP.

6. The composition of claim 1, wherein the MRE sequence is inserted within an artificially generated influenza virus 3' UTR.

7. The composition of claim 1, wherein the MRE sequence corresponds to miRNA which is characterized by species-specific expression.

8. The composition of claim 7, wherein the MRE sequence corresponds to miRNA which is highly expressed in influenza-targeted cells of an animal in need of vaccination but is not expressed or is expressed at very low levels in the regions where influenza viral propagation occurs within embryonated chicken eggs.

9. The composition of claim 1, wherein the MRE sequence corresponds to miRNA which is characterized by tissue-specific or cell-specific expression.

10. The composition of claim 9, wherein the MRE sequence corresponds to miRNA which is highly expressed in influenza-targeted cells of an animal in need of vaccination but is not expressed or is expressed at very low levels in a cell line used for vaccine production.

11. The composition of claim 10, wherein the cell line used for vaccine production is selected from the group consisting of chicken fibroblasts DF1, Madin-Darby Canine Kidney (MCK) cells, African green monkey kidney cells (Vero), and human PER-C6 cells.

12. The composition of claim 1, wherein the MRE sequence corresponds to miRNA selected from the group consisting of miR-16, miR-17, miR-19, miR-25, miR-34, miR-92, miR-93, miR-142, miR-222, miR-149, miR-1977, miR-181b-2, miR-1259, and miR-1978.

13. The composition of claim 12, wherein the MRE sequence corresponds to miRNA selected from the group consisting of miR-16 having sequence 5'-UAGCAG-CACGUAAAUAUUGGCG-3' (SEQ ID NO: 1), miR-17 having sequence 5'-CAAAGUGCUUACAGUGCAGGUAG-3' (SEQ ID NO: 2), miR-19 having sequence 5'-UGUG-CAAAUCUAUGCAAAACUGA-3' (SEQ ID NO: 3), miR-25 having sequence 5'-CAUUGCACUUGUCUCGGU-CUGA-3' (SEQ ID NO: 4), miR-34 having sequence 5'-UGGCAGUGUCUUAGCUGGUUGU-3' (SEQ ID NO: 5), miR-92 having sequence 5'-UAUUGCACUUGUCCCG-GCCUG-3' (SEQ ID NO: 6), miR-93 having sequence 5'-CAAAGUGCUGUUCGUGCAGGUAG-3' (SEQ ID NO: 7), miR-142 having sequence 5'-UGUAGUGUUUC-CUACUUUAUGGA-3' (SEQ ID NO: 141), miR-222 having sequence 5'-AGCUACAUCUGGCUACUGGU-3' (SEQ ID NO: 142), miR-149 having sequence 5'-UCUGGUCCGU-GUCUUCACUCCC-3' (SEQ ID NO: 143), miR-1977 having sequence 5'-GAUUAGGGUGCUUAGCUGUUAA-3' (SEQ ID NO: 144), miR-181b-2 having sequence 5'-AACA-UUCAUUGCUGUCGGUGGGU-3' (SEQ ID NO: 145), miR-1259 having sequence 5'-AUAUAUGAUGACU-UAGCUUUU-3' (SEQ ID NO: 146), and miR-1978 having sequence 5'-GGUUUGGUCCUAGCCUUUCUA-3' (SEQ ID NO: 147).

14. The composition of claim 1, wherein the recombinant influenza virus is derived from an influenza subtype selected from the group consisting of H5N1, H1N1, H2N2, and H3N2.

15. The composition of claim 1, wherein the recombinant influenza virus is derived from an isolate selected from the group consisting of A/Vietnam/1203/04, A/chicken/Scotland/59, A/duck/Hong Kong/308/78, A/PuertoRico/8/1934, A/NewYork/616/1995, A/California/04/2009, A/HongKong/16/68, A/USSR/039/68, A/Yokohama/C5/85, A/Leningrad/134/17/57, A/Leningrad/134/47/57, and A/Ann Arbor/6/60.

16. The composition of any one of claims 1-15 which is a vaccine composition.

17. The vaccine composition of claim 16 further comprising an adjuvant.

18. A method of inducing a protective immune response to an influenza infection in an animal, said method comprising administering to said animal the vaccine composition of claim 16.

19. The method of claim 18, wherein said animal is human.

20. The method of claim 18, wherein said vaccine composition is administered mucosally.

21. The method of claim 18, wherein said vaccine composition is administered conjointly with an adjuvant.

22. An isolated nucleic acid molecule comprising an influenza virus coding sequence and a MRE sequence inserted within said coding sequence, wherein the MRE sequence is selected such that the MFE of MRE interaction with its corresponding microRNA is less than −35 kcal/mol.

23. The nucleic acid molecule of claim 22, wherein the influenza virus coding sequence encodes an influenza virus protein selected from the group consisting of HA, NA, PB1, PB2, PA, M1, M2, NP, NS1, and NS2/NEP.

24. The nucleic acid molecule of claim 22, wherein the influenza virus coding sequence encodes an influenza virus protein selected from the group consisting of PB1, PB2, PA, M1, M2, NP, NS1, and NS2/NEP.

25. An isolated nucleic acid molecule comprising an influenza virus coding sequence and an artificial 3' untranslated region (3' UTR) comprising a MRE sequence inserted between the stop codon of the transcript and the polyadenylation site, wherein the MRE sequence is selected such that the MFE of MRE interaction with its corresponding microRNA is less than −35 kcal/mol.

26. The nucleic acid molecule of claim 22 or 25, wherein the MRE sequence corresponds to miRNA which is characterized by species-specific expression.

27. The nucleic acid molecule of claim 26, wherein the MRE sequence corresponds to miRNA which is highly expressed in influenza-targeted cells of an animal in need of vaccination but is not expressed or is expressed at very low levels in the regions where influenza viral propagation occurs within embryonated chicken eggs.

28. The nucleic acid molecule of claim 22 or 25, wherein the MRE sequence corresponds to miRNA which is characterized by tissue-specific or cell-specific expression.

29. The nucleic acid molecule of claim 28, wherein the MRE sequence corresponds to miRNA which is highly expressed in influenza-targeted cells of an animal in need of vaccination but is not expressed or is expressed at very low levels in a cell line used for vaccine production.

30. The nucleic acid molecule of claim 29, wherein the cell line used for vaccine production is selected from the group consisting of chicken fibroblasts DF1, Madin-Darby Canine Kidney (MCK) cells, African green monkey kidney cells (Vero), or human PER-C6 cells.

31. The nucleic acid molecule of claim 22 or 25, wherein the MRE sequence corresponds to miRNA selected from the group consisting of miR-16, miR-17, miR-19, miR-25, miR-34, miR-92, miR-93, miR-222, miR-149, miR-1977, miR-181b-2, miR-1259, and miR-1978.

32. The nucleic acid molecule of claim 31, wherein the MRE sequence corresponds to miRNA selected from the group consisting of miR-16 having sequence 5'-UAGCAG-CACGUAAAUAUUGGCG-3' (SEQ ID NO: 1), miR-17 having sequence 5'-CAAAGUGCUUACAGUGCAGGUAG-3' (SEQ ID NO: 2), miR-19 having sequence 5'-UGUG-CAAAUCUAUGCAAAACUGA-3' (SEQ ID NO: 3), miR-25 having sequence 5'-CAUUGCACUUGUCUCGGU-CUGA-3' (SEQ ID NO: 4), miR-34 having sequence 5'-UGGCAGUGUCUUAGCUGGUUGU-3' (SEQ ID NO: 5), miR-92 having sequence 5'-UAUUGCACUUGUCCCG-GCCUG-3' (SEQ ID NO: 6), miR-93 having sequence 5'-CAAAGUGCUGUUCGUGCAGGUAG-3' (SEQ ID NO: 7), miR-142 having sequence 5'-UGUAGUGUUUC-CUACUUUAUGGA-3' (SEQ ID NO: 141), miR-222 having sequence 5'-AGCUACAUCUGGCUACUGGU-3' (SEQ ID NO: 142), miR-149 having sequence 5'-UCUGGUCCGU-GUCUUCACUCCC-3' (SEQ ID NO: 143), miR-1977 having sequence 5'-GAUUAGGGUGCUUAGCUGUUAA-3' (SEQ ID NO: 144), miR-181b-2 having sequence 5'-AACA-UUCAUUGCUGUCGGUGGGU-3' (SEQ ID NO: 145), miR-1259 having sequence 5'-AUAUAUGAUGACU-UAGCUUUU-3' (SEQ ID NO: 146), and miR-1978 having sequence 5'-GGUUUGGUCCUAGCCUUUCUA-3' (SEQ ID NO: 147).

33. The nucleic acid molecule of claim 22 or 25 comprising one or more additional MRE sequences.

34. An isolated nucleic acid molecule comprising an influenza virus coding sequence and a first MRE sequence inserted within said coding sequence, wherein the MRE sequence is selected such that the MFE of MRE interaction with its corresponding microRNA is less than −25 kcal/mol;
wherein the isolated nucleic acid molecule further comprises a second MRE sequence; and
wherein both of the MRE sequences correspond to miR-93 and are inserted into the coding sequence of influenza virus protein NP, wherein the first MRE sequence is at the nucleotide sequence encoding NP amino acids 62-69 and the second MRE sequence is at the nucleotide sequence encoding NP amino acids 258-265.

35. The nucleic acid molecule of claim 34, wherein the first MRE sequence comprises the nucleotide sequence 5'-ACAATTGAACGAATGGTACTTTCT-3' (SEQ ID NO: 107).

36. The nucleic acid molecule of claim 34, wherein the second MRE sequence comprises the nucleotide sequence 5'-TTCCTTGCACGGTCAGCACTTATA-3' (SEQ ID NO: 111).

37. An isolated nucleic acid molecule comprising an influenza virus coding sequence and a first MRE sequence inserted within said coding sequence, wherein the MRE sequence is selected such that the MFE of MRE interaction with its corresponding microRNA is less than −25 kcal/mol;
wherein the isolated nucleic acid molecule further comprises a second MRE sequence; and
wherein both of the MRE sequences correspond to miR-92 and are inserted into the coding sequence of influenza virus protein NS1, wherein the first MRE sequence is at the nucleotide sequence encoding NS1 amino acids 131-137 and the second MRE sequence is at the nucleotide sequence encoding NS1 amino acids 150-156.

38. The nucleic acid molecule of claim 37, wherein the first MRE sequence comprises the nucleotide sequence 5'-AAGGCCAACTTCAGTGTAATA-3' (SEQ ID NO: 97).

39. The nucleic acid molecule of claim 37, wherein the second MRE sequence comprises the nucleotide sequence 5'-TTCACCGAGGAAGGTGCAATA-3' (SEQ ID NO: 101).

40. An isolated nucleic acid molecule comprising an influenza virus coding sequence and a first MRE sequence inserted within said coding sequence, wherein the MRE sequence is selected such that the MFE of MRE interaction with its corresponding microRNA is less than −25 kcal/mol;
wherein the isolated nucleic acid molecule further comprises a second and a third MRE sequence; and
wherein all three of the MRE sequences which correspond to miR-92 and are inserted into the coding sequence of influenza virus protein HA, wherein the first MRE sequence is at the nucleotide sequence encoding HA amino acids 68-74, the second MRE sequence is at the nucleotide sequence encoding HA amino acids 195-201, and the third MRE sequence is at the nucleotide sequence encoding HA amino acids 526-532.

41. The nucleic acid molecule of claim 40, wherein the first MRE sequence comprises the nucleotide sequence 5'-CTACAGTTGGGGAAGTGCAAT-3' (SEQ ID NO: 83).

42. The nucleic acid molecule of claim 40, wherein the second MRE sequence comprises the nucleotide sequence 5'-AACGCCTATGTAAGTGTAGTA-3' (SEQ ID NO: 87).

43. The nucleic acid molecule of claim 40, wherein the third MRE sequence comprises the nucleotide sequence 5'-TTGGTCAGTTTAGGTGCAATA-3' (SEQ ID NO: 91).

44. An isolated nucleic acid molecule comprising an influenza virus coding sequence and a first MRE sequence inserted within said coding sequence, wherein the MRE sequence is selected such that the MFE of MRE interaction with its corresponding microRNA is less than −25 kcal/mol;
wherein the isolated nucleic acid molecule further comprises a second and a third MRE sequence; and
wherein all three of the MRE sequences correspond to miR-19 and are inserted into the coding sequence of influenza virus protein HA, wherein the first MRE sequence is at the nucleotide sequence encoding HA amino acids 15-22, the second MRE sequence is at the nucleotide sequence encoding HA amino acids 561-568, and the third MRE sequence is at the nucleotide sequence encoding HA amino acids 327-334.

45. The nucleic acid molecule of claim 44, wherein the first MRE sequence comprises the nucleotide sequence 5'-GCCAGTGCTGACACAATTTGCATA-3' (SEQ ID NO: 45).

46. The nucleic acid molecule of claim 44, wherein the second MRE sequence comprises the nucleotide sequence 5'-TCTTTGCAGTGCAGGATTTGCATA-3' (SEQ ID NO: 49).

47. The nucleic acid molecule of claim 44, wherein the third MRE sequence comprises the nucleotide sequence 5'-TTGCGUATGGTCACAGGTTTGCGC-3' (SEQ ID NO: 53).

48. An isolated nucleic acid molecule comprising an influenza virus coding sequence and a first MRE sequence inserted within said coding sequence, wherein the MRE sequence is selected such that the MFE of MRE interaction with its corresponding microRNA is less than −25 kcal/mol;
wherein the isolated nucleic acid molecule further comprises a second MRE sequence; and
wherein both of the MRE sequences which correspond to miR-16 and are inserted into the coding sequence of influenza virus protein HA, wherein the first MRE sequence is at the nucleotide sequence encoding HA amino acids 2-9 and the second MRE sequence is at the nucleotide sequence encoding HA amino acids 439-445.

49. The nucleic acid molecule of claim 48, wherein the first MRE sequence comprises the nucleotide sequence 5'-AAGGCCAACCTATTAGTGCTGCTA-3' (SEQ ID NO: 21).

50. The nucleic acid molecule of claim 48, wherein the second MRE sequence comprises the nucleotide sequence 5'-AACGCCGAACTATTAGTGCTGCTA-3' (SEQ ID NO: 25).

51. An isolated nucleic acid molecule comprising an influenza virus coding sequence and a first MRE sequence inserted within said coding sequence, wherein the MRE sequence is selected such that the MFE of MRE interaction with its corresponding microRNA is less than −25 kcal/mol;
wherein the isolated nucleic acid molecule further comprises a second and a third MRE sequence; and
wherein all three of the MRE sequences which correspond to miR-34 and are inserted into the coding sequence of influenza virus protein PA, wherein the first MRE sequence is at the nucleotide sequence encoding PA amino acids 426-433, the second MRE sequence is at the nucleotide sequence encoding PA amino acids 634-641, and the third MRE sequence is at the nucleotide sequence encoding PA amino acids 709-716.

52. The nucleic acid molecule of claim 51, wherein the first MRE sequence comprises the nucleotide sequence 5'-GATGAGATCGGTGAAGACGTTGCC-3' (SEQ ID NO: 69).

53. The nucleic acid molecule of claim 51, wherein the second MRE sequence comprises the nucleotide sequence 5'-GGCAAGGTATGTAGGACACTGTTA-3' (SEQ ID NO: 73).

54. The nucleic acid molecule of claim 51, wherein the third MRE sequence comprises the nucleotide sequence 5'-TTCTTCCTGACTCATGCACTGTCA-3' (SEQ ID NO: 77).

55. An isolated nucleic acid molecule comprising an influenza virus coding sequence and a first MRE sequence inserted within said coding sequence, wherein the MRE sequence is selected such that the MFE of MRE interaction with its corresponding microRNA is less than −25 kcal/mol;
wherein the isolated nucleic acid molecule further comprises a second MRE sequence; and
wherein both of the MRE sequences which correspond to miR-25 and are inserted into the coding sequence of influenza virus protein M1, wherein the first MRE sequence is at the nucleotide sequence encoding M1 amino acids 111-118 and the second MRE sequence is at the nucleotide sequence encoding M1 amino acids 127-134.

56. The nucleic acid molecule of claim 55, wherein the first MRE sequence comprises the nucleotide sequence 5'-GGTGCCAAAGAGATAAGTGCAAGT-3' (SEQ ID NO: 59).

57. The nucleic acid molecule of claim 55, wherein the second MRE sequence comprises the nucleotide sequence 5'-ATATACAACAGGATGGGTGCAGTG-3" (SEQ ID NO: 63).

58. An isolated nucleic acid molecule comprising an influenza virus coding sequence and a first MRE sequence inserted within said coding sequence, wherein the MRE sequence is selected such that the MFE of MRE interaction with its corresponding microRNA is less than −25 kcal/mol;
wherein the isolated nucleic acid molecule further comprises a second and a third MRE sequence; and
wherein all three of the MRE sequences correspond to miR-17 and are inserted into the coding sequence of influenza virus protein PB1, wherein the first MRE sequence is at the nucleotide sequence encoding PB1 amino acids 374-381, the second MRE sequence is at the nucleotide sequence encoding PB1 amino acids 418-424, and the third MRE sequence is at the nucleotide sequence encoding PB1 amino acids 677-683.

59. The nucleic acid molecule of claim 58, wherein the first MRE sequence comprises the nucleotide sequence 5'-GCCAGCATTGATCTTAAGTACTTT-3' (SEQ ID NO: 31).

60. The nucleic acid molecule of claim 58, wherein the second MRE sequence comprises the nucleotide sequence 5'-GTGTTGGGTGTAAGCATTTTG-3' (SEQ ID NO: 35).

61. The nucleic acid molecule of claim 58, wherein the third MRE sequence comprises the nucleotide sequence 5'-ACCAGCCAAAGAGGCGTTTTG-3' (SEQ ID NO: 39).

62. An isolated nucleic acid molecule comprising an influenza virus coding sequence and an artificial 3' untranslated region (3' UTR) comprising a first MRE sequence inserted between the stop codon of the transcript and the polyadenylation site, wherein the first MRE sequence is selected such that the MFE of MRE interaction with its corresponding microRNA is less than −25 kcal/mol;
wherein the isolated nucleic acid molecule further comprises second, third, and fourth MRE sequences; and
wherein all four of the MRE sequences correspond to miR-142 and are inserted into an artificial 3' UTR of influenza virus protein NP, wherein each of the MRE sequences are found between the viral stop codon and the polyA tail sequence.

63. The nucleic acid molecule of claim 62, wherein each of the four MRE sequences comprises the nucleotide sequence 5'-TCCATAAAGTAGGAAACACTACA-3' (SEQ ID NO: 159).

64. An isolated nucleic acid molecule comprising an influenza virus coding sequence and an artificial 3' untranslated region (3' UTR) comprising a first MRE sequence inserted between the stop codon of the transcript and the polyadenylation site, wherein the first MRE sequence is selected such that the MFE of MRE interaction with its corresponding microRNA is less than −25 kcal/mol;
wherein the isolated nucleic acid molecule further comprises second, third, and fourth MRE sequences; and
wherein all four of the MRE sequences which correspond to miR-142 and are inserted into an artificial 3' UTR of influenza virus protein NS1, wherein each of the MRE sequences is found between the viral stop codon and the polyA tail sequence but before a duplicated NS2/NEP ORF.

65. The nucleic acid molecule of claim 64, wherein each of the four MRE sequences comprises the nucleotide sequence 5'-TCCATAAAGTAGGAAACACTACA-3' (SEQ ID NO: 159).

* * * * *

SEQUENCE LISTING

```
<160> NUMBER OF SEQ ID NOS: 186

<210> SEQ ID NO 1
<211> LENGTH: 22
<212> TYPE: RNA
<213> ORGANISM: Homo sapiens

<400> SEQUENCE: 1
uagcagcacg uaaauauugg cg                                              22

<210> SEQ ID NO 2
<211> LENGTH: 23
<212> TYPE: RNA
<213> ORGANISM: Homo sapiens

<400> SEQUENCE: 2
caaagugcuu acagugcagg uag                                             23

<210> SEQ ID NO 3
<211> LENGTH: 23
<212> TYPE: RNA
<213> ORGANISM: Homo sapiens
```

```
<400> SEQUENCE: 3
ugugcaaauc uaugcaaaac uga                                          23

<210> SEQ ID NO 4
<211> LENGTH: 22
<212> TYPE: RNA
<213> ORGANISM: Homo sapiens

<400> SEQUENCE: 4
cauugcacuu gucucggucu ga                                           22

<210> SEQ ID NO 5
<211> LENGTH: 22
<212> TYPE: RNA
<213> ORGANISM: Homo sapiens

<400> SEQUENCE: 5
uggcaguguc uuagcugguu gu                                           22

<210> SEQ ID NO 6
<211> LENGTH: 21
<212> TYPE: RNA
<213> ORGANISM: Homo sapiens

<400> SEQUENCE: 6
uauugcacuu gucccggccu g                                            21

<210> SEQ ID NO 7
<211> LENGTH: 23
<212> TYPE: RNA
<213> ORGANISM: Homo sapiens

<400> SEQUENCE: 7
caaagugcug uucgugcagg uag                                          23

<210> SEQ ID NO 8
<211> LENGTH: 9
<212> TYPE: RNA
<213> ORGANISM: Homo sapiens

<400> SEQUENCE: 8 uagcagcac                                                           9

<210> SEQ ID NO 9
<211> LENGTH: 9
<212> TYPE: RNA
<213> ORGANISM: Homo sapiens

<400> SEQUENCE: 9 agcagcagc                                                           9

<210> SEQ ID NO 10
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 10 gtgctgcta                                                           9

<210> SEQ ID NO 11
```

-continued

<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 11
cgtgctgcta 10

<210> SEQ ID NO 12
<211> LENGTH: 24
<212> TYPE: RNA
<213> ORGANISM: Influenza virus

<400> SEQUENCE: 12
acaauagaga gaauggugcu cucu 24

<210> SEQ ID NO 13
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 13
acacuugaac gaaugguacu uucu 24

<210> SEQ ID NO 14
<211> LENGTH: 24
<212> TYPE: RNA
<213> ORGANISM: Influenza virus

<400> SEQUENCE: 14
uuucuagcac ggucugcacu caua 24

<210> SEQ ID NO 15
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 15
uuccuugcac ggacagcacu uuua 24

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
cgccaatatt tacgtgctgc ta 22

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
cgccaatatt tacgtgctgc ta 22

```
<210> SEQ ID NO 18
<211> LENGTH: 8
<212> TYPE: PRT
<213> ORGANISM: Influenza virus

<400> SEQUENCE: 18

Lys Ala Asn Leu Leu Val Leu Leu
1               5

<210> SEQ ID NO 19
<211> LENGTH: 24
<212> TYPE: DNA
<213> ORGANISM: Influenza virus

<400> SEQUENCE: 19
aaggcaaacc tactggtcct gtta                                              24

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

<400> SEQUENCE: 20

Lys Ala Asn Leu Leu Leu Leu Leu
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
aaggccaacc tattagtgct gcta                                              24

<210> SEQ ID NO 22
<211> LENGTH: 8
<212> TYPE: PRT
<213> ORGANISM: Influenza virus

<400> SEQUENCE: 22

Asn Ala Glu Leu Leu Val Leu Leu
1               5

<210> SEQ ID NO 23
<211> LENGTH: 24
<212> TYPE: DNA
<213> ORGANISM: Influenza virus

<400> SEQUENCE: 23
aatgcagaat tgttagttct actg                                              24

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Asn Ala Glu Leu Leu Val Leu Leu
1               5
```

```
<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25
aacgccgaac tattagtgct gcta                                        24

<210> SEQ ID NO 26
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 26
ctacctgcac tgtaagcact ttg                                         23

<210> SEQ ID NO 27
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 27
ctacctgcac tgtaagcact ttg                                         23

<210> SEQ ID NO 28
<211> LENGTH: 8
<212> TYPE: PRT
<213> ORGANISM: Influenza virus

<400> SEQUENCE: 28

Ala Ser Ile Asp Leu Lys Tyr Phe
1               5

<210> SEQ ID NO 29
<211> LENGTH: 24
<212> TYPE: DNA
<213> ORGANISM: Influenza virus

<400> SEQUENCE: 29
gcaagcattg atttgaaata tttc                                        24

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide

<400> SEQUENCE: 30

Ala Ser Ile Asp Leu Lys Tyr Phe
1               5

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 31
```

```
gccagcattg atcttaagta cttt                                              24

<210> SEQ ID NO 32
<211> LENGTH: 7
<212> TYPE: PRT
<213> ORGANISM: Influenza virus

<400> SEQUENCE: 32

Val Leu Gly Val Ser Ile Leu
1               5

<210> SEQ ID NO 33
<211> LENGTH: 21
<212> TYPE: DNA
<213> ORGANISM: Influenza virus

<400> SEQUENCE: 33
gtattaggcg tctccatcct g                                                 21

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide

<400> SEQUENCE: 34

Val Leu Gly Val Ser Ile Leu
1               5

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 35
gtgttgggtg taagcatttt g                                                 21

<210> SEQ ID NO 36
<211> LENGTH: 7
<212> TYPE: PRT
<213> ORGANISM: Influenza virus

<400> SEQUENCE: 36

Thr Ser Gln Arg Gly Val Leu
1               5

<210> SEQ ID NO 37
<211> LENGTH: 21
<212> TYPE: DNA
<213> ORGANISM: Influenza virus

<400> SEQUENCE: 37
acaagtcaaa gaggagtact t                                                 21

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38
```

-continued

Thr Ser Gln Arg Gly Val Leu
1               5

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
accagccaaa gaggcgtttt g                                                 21

<210> SEQ ID NO 40
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 40
tcagttttgc atagatttgc aca                                               23

<210> SEQ ID NO 41
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 41
tcagttttgc atagatttgc aca                                               23

<210> SEQ ID NO 42
<211> LENGTH: 8
<212> TYPE: PRT
<213> ORGANISM: Influenza virus

<400> SEQUENCE: 42

Ala Asp Ala Asp Thr Ile Cys Ile
1               5

<210> SEQ ID NO 43
<211> LENGTH: 24
<212> TYPE: DNA
<213> ORGANISM: Influenza virus

<400> SEQUENCE: 43
gcagatgcag acacaatatg tata                                              24

<210> SEQ ID NO 44
<211> LENGTH: 8
<212> TYPE: PRT
<213> ORGANISM: Artificial Sequence
<220> FEATURE:
<223> OTHER INFORMATION: Synthetic peptide

<400> SEQUENCE: 44

Ala Asp Ala Asp Thr Ile Cys Ile
1               5

<210> SEQ ID NO 45
<211> LENGTH: 24
<212> TYPE: DNA
<213> ORGANISM: Artificial Sequence

```
<220> FEATURE:
<223> OTHER INFORMATION: Synthetic oligonucleotide

<400> SEQUENCE: 45
gccagtgctg acacaatttg cata                                          24

<210> SEQ ID NO 46
<211> LENGTH: 8
<212> TYPE: PRT
<213> ORGANISM: Influenza virus

<400> SEQUENCE: 46

Ser Leu Gln Cys Arg Ile Cys Ile
1               5

<210> SEQ ID NO 47
<211> LENGTH: 24
<212> TYPE: DNA
<213> ORGANISM: Influenza virus

<400> SEQUENCE: 47
tctttgcagt gcagaatatg catc                                          24

<210> SEQ ID NO 48
<211> LENGTH: 8
<212> TYPE: PRT
<213> ORGANISM: Artificial Sequence
<220> FEATURE:
<223> OTHER INFORMATION: Synthetic peptide

<400> SEQUENCE: 48

Ser Leu Gln Cys Arg Ile Cys Ile
1               5

<210> SEQ ID NO 49
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 49
tctttgcagt gcaggatttg cata                                          24

<210> SEQ ID NO 50
<211> LENGTH: 8
<212> TYPE: PRT
<213> ORGANISM: Influenza virus

<400> SEQUENCE: 50

Leu Arg Met Val Thr Gly Leu Arg
1               5

<210> SEQ ID NO 51
<211> LENGTH: 24
<212> TYPE: DNA
<213> ORGANISM: Influenza virus

<400> SEQUENCE: 51
ttgaggatgg ttacaggact aagg                                          24

<210> SEQ ID NO 52
<211> LENGTH: 8
<212> TYPE: PRT
<213> ORGANISM: Artificial Sequence
```

```
<220> FEATURE:
<223> OTHER INFORMATION: Synthetic peptide

<400> SEQUENCE: 52

Leu Arg Met Val Thr Gly Leu Arg
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<223> OTHER INFORMATION: Synthetic oligonucleotide

<400> SEQUENCE: 53
ttgcguatgg tcacaggttt gcgc                                          24

<210> SEQ ID NO 54
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 54
tcagaccgag acaagtgcaa tg                                            22

<210> SEQ ID NO 55
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 55
tcagaccggg acaagtgcaa tg                                            22

<210> SEQ ID NO 56
<211> LENGTH: 8
<212> TYPE: PRT
<213> ORGANISM: Influenza virus

<400> SEQUENCE: 56

Gly Ala Lys Glu Ile Ser Leu Ser
1               5

<210> SEQ ID NO 57
<211> LENGTH: 24
<212> TYPE: DNA
<213> ORGANISM: Influenza virus

<400> SEQUENCE: 57
ggggccaaag aaatctcact cagt                                          24

<210> SEQ ID NO 58
<211> LENGTH: 8
<212> TYPE: PRT
<213> ORGANISM: Artificial Sequence
<220> FEATURE:
<223> OTHER INFORMATION: Synthetic peptide

<400> SEQUENCE: 58

Gly Ala Lys Glu Ile Ser Leu Ser
1               5
```

```
<210> SEQ ID NO 59
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 59
ggtgccaaag agataagtgc aagt                                          24

<210> SEQ ID NO 60
<211> LENGTH: 8
<212> TYPE: PRT
<213> ORGANISM: Influenza virus

<400> SEQUENCE: 60

Ile Tyr Asn Arg Met Gly Ala Val
1               5

<210> SEQ ID NO 61
<211> LENGTH: 24
<212> TYPE: DNA
<213> ORGANISM: Influenza virus

<400> SEQUENCE: 61
atatacaaca ggatgggggc tgtg                                          24

<210> SEQ ID NO 62
<211> LENGTH: 8
<212> TYPE: PRT
<213> ORGANISM: Artificial Sequence
<220> FEATURE:
<223> OTHER INFORMATION: Synthetic peptide

<400> SEQUENCE: 62

Ile Tyr Asn Arg Met Gly Ala Val
1               5

<210> SEQ ID NO 63
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 63
atatacaaca ggatgggtgc agtg                                          24

<210> SEQ ID NO 64
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 64
acaaccagct aagacactgc ca                                            22

<210> SEQ ID NO 65
<211> LENGTH: 22
<212> TYPE: DNA
<213> ORGANISM: Artificial Sequence
<220> FEATURE:
<223> OTHER INFORMATION: Synthetic oligonucleotide
```

<400> SEQUENCE: 65
acaaccagct aagacactgc ca                                    22

<210> SEQ ID NO 66
<211> LENGTH: 8
<212> TYPE: PRT
<213> ORGANISM: Influenza virus

<400> SEQUENCE: 66

Asp Glu Ile Gly Glu Asp Val Ala
1               5

<210> SEQ ID NO 67
<211> LENGTH: 24
<212> TYPE: DNA
<213> ORGANISM: Influenza virus

<400> SEQUENCE: 67
gatgagattg gagaagatgt ggct                                  24

<210> SEQ ID NO 68
<211> LENGTH: 8
<212> TYPE: PRT
<213> ORGANISM: Artificial Sequence
<220> FEATURE:
<223> OTHER INFORMATION: Synthetic peptide

<400> SEQUENCE: 68

Asp Glu Ile Gly Glu Asp Val Ala
1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 69
gatgagatcg gtgaagacgt tgcc                                  24

<210> SEQ ID NO 70
<211> LENGTH: 8
<212> TYPE: PRT
<213> ORGANISM: Influenza virus

<400> SEQUENCE: 70

Gly Lys Val Cys Arg Thr Leu Leu
1               5

<210> SEQ ID NO 71
<211> LENGTH: 24
<212> TYPE: DNA
<213> ORGANISM: Influenza virus

<400> SEQUENCE: 71
gggaaggtct gcaggacttt atta                                  24

<210> SEQ ID NO 72
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 72

Gly Lys Val Cys Arg Thr Leu Leu
1               5

<210> SEQ ID NO 73
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 73
ggcaaggtat gtaggacact gtta                                            24

<210> SEQ ID NO 74
<211> LENGTH: 8
<212> TYPE: PRT
<213> ORGANISM: Influenza virus

<400> SEQUENCE: 74

Ser Phe Leu Thr His Ala Leu Ser
1               5

<210> SEQ ID NO 75
<211> LENGTH: 24
<212> TYPE: DNA
<213> ORGANISM: Influenza virus

<400> SEQUENCE: 75
ttcttcctta cacatgcatt gagt                                            24

<210> SEQ ID NO 76
<211> LENGTH: 8
<212> TYPE: PRT
<213> ORGANISM: Artificial Sequence
<220> FEATURE:
<223> OTHER INFORMATION: Synthetic peptide

<400> SEQUENCE: 76

Ser Phe Leu Thr His Ala Leu Ser
1               5

<210> SEQ ID NO 77
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 77
ttcttcctga ctcatgcact gtca                                            24

<210> SEQ ID NO 78
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 78
caggccggga caagtgcaat a                                               21

<210> SEQ ID NO 79
<211> LENGTH: 21
<212> TYPE: DNA
```

```
<213> ORGANISM: Artificial Sequence
<220> FEATURE:
<223> OTHER INFORMATION: Synthetic oligonucleotide

<400> SEQUENCE: 79
caggccggga caagtgcaat a                                                 21

<210> SEQ ID NO 80
<211> LENGTH: 7
<212> TYPE: PRT
<213> ORGANISM: Influenza virus

<400> SEQUENCE: 80

Gln Leu Gly Lys Cys Asn Ile
1               5

<210> SEQ ID NO 81
<211> LENGTH: 21
<212> TYPE: DNA
<213> ORGANISM: Influenza virus

<400> SEQUENCE: 81
ctacaattgg ggaaatgtaa c                                                 21

<210> SEQ ID NO 82
<211> LENGTH: 7
<212> TYPE: PRT
<213> ORGANISM: Artificial Sequence
<220> FEATURE:
<223> OTHER INFORMATION: Synthetic peptide

<400> SEQUENCE: 82

Gln Leu Gly Lys Cys Asn Ile
1               5

<210> SEQ ID NO 83
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 83
ctacagttgg ggaagtgcaa t                                                 21

<210> SEQ ID NO 84
<211> LENGTH: 7
<212> TYPE: PRT
<213> ORGANISM: Influenza virus

<400> SEQUENCE: 84

Asn Ala Tyr Val Ser Val Val
1               5

<210> SEQ ID NO 85
<211> LENGTH: 21
<212> TYPE: DNA
<213> ORGANISM: Influenza virus

<400> SEQUENCE: 85
aatgcttatg tctctgtagt g                                                 21

<210> SEQ ID NO 86
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 86

Asn Ala Tyr Val Ser Val Val
1               5

<210> SEQ ID NO 87
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 87
aacgcctatg taagtgtagt a                                              21

<210> SEQ ID NO 88
<211> LENGTH: 7
<212> TYPE: PRT
<213> ORGANISM: Influenza virus

<400> SEQUENCE: 88

Leu Val Ser Leu Gly Ala Ile
1               5

<210> SEQ ID NO 89
<211> LENGTH: 21
<212> TYPE: DNA
<213> ORGANISM: Influenza virus

<400> SEQUENCE: 89
ttggtctccc tgggggcaat c                                              21

<210> SEQ ID NO 90
<211> LENGTH: 7
<212> TYPE: PRT
<213> ORGANISM: Artificial Sequence
<220> FEATURE:
<223> OTHER INFORMATION: Synthetic peptide

<400> SEQUENCE: 90

Leu Val Ser Leu Gly Ala Ile
1               5

<210> SEQ ID NO 91
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 91
ttggtcagtt taggtgcaat a                                              21

<210> SEQ ID NO 92
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 92
caggccggga caagtgcaat a                                              21
```

<210> SEQ ID NO 93
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 93
caggccggga caagtgcaat a 21

<210> SEQ ID NO 94
<211> LENGTH: 7
<212> TYPE: PRT
<213> ORGANISM: Influenza virus

<400> SEQUENCE: 94

Lys Ala Asn Phe Ser Val Ile
1 5

<210> SEQ ID NO 95
<211> LENGTH: 21
<212> TYPE: DNA
<213> ORGANISM: Influenza virus

<400> SEQUENCE: 95
aaagcaaact tcagtgtgat t 21

<210> SEQ ID NO 96
<211> LENGTH: 7
<212> TYPE: PRT
<213> ORGANISM: Artificial Sequence
<220> FEATURE:
<223> OTHER INFORMATION: Synthetic peptide

<400> SEQUENCE: 96

Lys Ala Asn Phe Ser Val Ile
1 5

<210> SEQ ID NO 97
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 97
aaggccaact tcagtgtaat a 21

<210> SEQ ID NO 98
<211> LENGTH: 7
<212> TYPE: PRT
<213> ORGANISM: Influenza virus

<400> SEQUENCE: 98

Phe Thr Glu Glu Gly Ala Ile
1 5

<210> SEQ ID NO 99
<211> LENGTH: 21
<212> TYPE: DNA
<213> ORGANISM: Influenza virus

<400> SEQUENCE: 99
ttcaccgaag agggagcaat t 21

<210> SEQ ID NO 100
<211> LENGTH: 7
<212> TYPE: PRT
<213> ORGANISM: Artificial Sequence
<220> FEATURE:
<223> OTHER INFORMATION: Synthetic peptide

<400> SEQUENCE: 100

Phe Thr Glu Glu Gly Ala Ile
1               5

<210> SEQ ID NO 101
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 101
ttcaccgagg aaggtgcaat a                                               21

<210> SEQ ID NO 102
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 102
ctacctgcac gaacagcact ttg                                             23

<210> SEQ ID NO 103
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 103
ctacctgcac gaacagcact ttg                                             23

<210> SEQ ID NO 104
<211> LENGTH: 8
<212> TYPE: PRT
<213> ORGANISM: Influenza virus

<400> SEQUENCE: 104

Thr Ile Glu Arg Met Val Leu Ser
1               5

<210> SEQ ID NO 105
<211> LENGTH: 24
<212> TYPE: DNA
<213> ORGANISM: Influenza virus

<400> SEQUENCE: 105
acaatagaga gaatggtgct ctct                                            24

<210> SEQ ID NO 106
<211> LENGTH: 8
<212> TYPE: PRT
<213> ORGANISM: Artificial Sequence
<220> FEATURE:
<223> OTHER INFORMATION: Synthetic peptide

<400> SEQUENCE: 106

```
Thr Ile Glu Arg Met Val Leu Ser
1               5

<210> SEQ ID NO 107
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 107
acaattgaac gaatggtact ttct                                              24

<210> SEQ ID NO 108
<211> LENGTH: 8
<212> TYPE: PRT
<213> ORGANISM: Influenza virus

<400> SEQUENCE: 108

Phe Leu Ala Arg Ser Ala Leu Ile
1               5

<210> SEQ ID NO 109
<211> LENGTH: 24
<212> TYPE: DNA
<213> ORGANISM: Influenza virus

<400> SEQUENCE: 109
tttctggcac ggtctgcact cata                                              24

<210> SEQ ID NO 110
<211> LENGTH: 8
<212> TYPE: PRT
<213> ORGANISM: Artificial Sequence
<220> FEATURE:
<223> OTHER INFORMATION: Synthetic peptide

<400> SEQUENCE: 110

Phe Leu Ala Arg Ser Ala Leu Ile
1               5

<210> SEQ ID NO 111
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 111
ttccttgcac ggtcagcact tata                                              24

<210> SEQ ID NO 112
<211> LENGTH: 23
<212> TYPE: DNA
<213> ORGANISM: Artificial Sequence
<220> FEATURE:
<223> OTHER INFORMATION: Synthetic primer

<400> SEQUENCE: 112
tagtggtcct ctctgtgcta ccg                                               23

<210> SEQ ID NO 113
<211> LENGTH: 23
<212> TYPE: DNA
<213> ORGANISM: Artificial Sequence
```

```
<220> FEATURE:
<223> OTHER INFORMATION: Synthetic primer

<400> SEQUENCE: 113
attgaacaaa aatggggact cct                                        23

<210> SEQ ID NO 114
<211> LENGTH: 23
<212> TYPE: DNA
<213> ORGANISM: Artificial Sequence
<220> FEATURE:
<223> OTHER INFORMATION: Synthetic primer

<400> SEQUENCE: 114
aacaccttca gagtcgttgg agt                                        23

<210> SEQ ID NO 115
<211> LENGTH: 20
<212> TYPE: DNA
<213> ORGANISM: Artificial Sequence
<220> FEATURE:
<223> OTHER INFORMATION: Synthetic primer

<400> SEQUENCE: 115
ggaggcccac tacatgagac                                            20

<210> SEQ ID NO 116
<211> LENGTH: 18
<212> TYPE: DNA
<213> ORGANISM: Artificial Sequence
<220> FEATURE:
<223> OTHER INFORMATION: Synthetic primer

<400> SEQUENCE: 116
gtcctggcgc ggtgctct                                              18

<210> SEQ ID NO 117
<211> LENGTH: 20
<212> TYPE: DNA
<213> ORGANISM: Artificial Sequence
<220> FEATURE:
<223> OTHER INFORMATION: Synthetic primer

<400> SEQUENCE: 117
tctcttgctc cttcccttgc                                            20

<210> SEQ ID NO 118
<211> LENGTH: 25
<212> TYPE: DNA
<213> ORGANISM: Artificial Sequence
<220> FEATURE:
<223> OTHER INFORMATION: Synthetic primer

<400> SEQUENCE: 118
catttcaaga acaacctacc agaga                                      25

<210> SEQ ID NO 119
<211> LENGTH: 23
<212> TYPE: DNA
<213> ORGANISM: Artificial Sequence
<220> FEATURE:
<223> OTHER INFORMATION: Synthetic primer

<400> SEQUENCE: 119
aagtttatcc agcagggtga ctc                                        23
```

```
<210> SEQ ID NO 120
<211> LENGTH: 25
<212> TYPE: DNA
<213> ORGANISM: Artificial Sequence
<220> FEATURE:
<223> OTHER INFORMATION: Synthetic primer

<400> SEQUENCE: 120
tctgatgtga acacaaggac attca                                              25

<210> SEQ ID NO 121
<211> LENGTH: 23
<212> TYPE: DNA
<213> ORGANISM: Artificial Sequence
<220> FEATURE:
<223> OTHER INFORMATION: Synthetic primer

<400> SEQUENCE: 121
tttccaccat ctttaccctg ttt                                                23

<210> SEQ ID NO 122
<211> LENGTH: 23
<212> TYPE: DNA
<213> ORGANISM: Artificial Sequence
<220> FEATURE:
<223> OTHER INFORMATION: Synthetic primer

<400> SEQUENCE: 122
gaagctcatg aggcgttaca tag                                                23

<210> SEQ ID NO 123
<211> LENGTH: 21
<212> TYPE: DNA
<213> ORGANISM: Artificial Sequence
<220> FEATURE:
<223> OTHER INFORMATION: Synthetic primer

<400> SEQUENCE: 123
attgacctgc cagacattga g                                                  21

<210> SEQ ID NO 124
<211> LENGTH: 23
<212> TYPE: DNA
<213> ORGANISM: Artificial Sequence
<220> FEATURE:
<223> OTHER INFORMATION: Synthetic primer

<400> SEQUENCE: 124
ttcccagtcc actgtggttc ttc                                                23

<210> SEQ ID NO 125
<211> LENGTH: 22
<212> TYPE: DNA
<213> ORGANISM: Artificial Sequence
<220> FEATURE:
<223> OTHER INFORMATION: Synthetic primer

<400> SEQUENCE: 125
tggcactgaa gtatagggga tg                                                 22

<210> SEQ ID NO 126
<211> LENGTH: 22
<212> TYPE: DNA
<213> ORGANISM: Artificial Sequence
<220> FEATURE:
<223> OTHER INFORMATION: Synthetic primer
```

```
<400> SEQUENCE: 126
cccagctatg taatcgcctc ta                                          22

<210> SEQ ID NO 127
<211> LENGTH: 21
<212> TYPE: DNA
<213> ORGANISM: Artificial Sequence
<220> FEATURE:
<223> OTHER INFORMATION: Synthetic primer

<400> SEQUENCE: 127
ctgcctggtt aggtagcatg a                                           21

<210> SEQ ID NO 128
<211> LENGTH: 22
<212> TYPE: DNA
<213> ORGANISM: Artificial Sequence
<220> FEATURE:
<223> OTHER INFORMATION: Synthetic primer

<400> SEQUENCE: 128
gatgaactga aacctccaaa gc                                          22

<210> SEQ ID NO 129
<211> LENGTH: 22
<212> TYPE: DNA
<213> ORGANISM: Artificial Sequence
<220> FEATURE:
<223> OTHER INFORMATION: Synthetic primer

<400> SEQUENCE: 129
atctgctgga tctctcctgt gt                                          22

<210> SEQ ID NO 130
<211> LENGTH: 23
<212> TYPE: DNA
<213> ORGANISM: Artificial Sequence
<220> FEATURE:
<223> OTHER INFORMATION: Synthetic primer

<400> SEQUENCE: 130
caacggtttc tgtcaggatg aat                                         23

<210> SEQ ID NO 131
<211> LENGTH: 23
<212> TYPE: DNA
<213> ORGANISM: Artificial Sequence
<220> FEATURE:
<223> OTHER INFORMATION: Synthetic primer

<400> SEQUENCE: 131
aggggaactg tggtcactat cac                                         23

<210> SEQ ID NO 132
<211> LENGTH: 23
<212> TYPE: DNA
<213> ORGANISM: Artificial Sequence
<220> FEATURE:
<223> OTHER INFORMATION: Synthetic primer

<400> SEQUENCE: 132
tgcttgggag gaaataaac aat                                          23

<210> SEQ ID NO 133
```

```
<210> SEQ ID NO 133
<211> LENGTH: 23
<212> TYPE: DNA
<213> ORGANISM: Artificial Sequence
<220> FEATURE:
<223> OTHER INFORMATION: Synthetic primer

<400> SEQUENCE: 133
gactctaagt gccaccagac aga                                              23

<210> SEQ ID NO 134
<211> LENGTH: 20
<212> TYPE: DNA
<213> ORGANISM: Artificial Sequence
<220> FEATURE:
<223> OTHER INFORMATION: Synthetic primer

<400> SEQUENCE: 134
gcctggacca caagtttgac                                                  20

<210> SEQ ID NO 135
<211> LENGTH: 20
<212> TYPE: DNA
<213> ORGANISM: Artificial Sequence
<220> FEATURE:
<223> OTHER INFORMATION: Synthetic primer

<400> SEQUENCE: 135
tgaaattctg ggagcatgac                                                  20

<210> SEQ ID NO 136
<211> LENGTH: 22
<212> TYPE: DNA
<213> ORGANISM: Artificial Sequence
<220> FEATURE:
<223> OTHER INFORMATION: Synthetic probe

<400> SEQUENCE: 136
tggcattcac cgcgtgcctt aa                                               22

<210> SEQ ID NO 137
<211> LENGTH: 23
<212> TYPE: DNA
<213> ORGANISM: Artificial Sequence
<220> FEATURE:
<223> OTHER INFORMATION: Synthetic probe

<400> SEQUENCE: 137
ctacctgcac gaacagcact ttg                                              23

<210> SEQ ID NO 138
<211> LENGTH: 23
<212> TYPE: DNA
<213> ORGANISM: Artificial Sequence
<220> FEATURE:
<223> OTHER INFORMATION: Synthetic probe

<400> SEQUENCE: 138
gccatgctaa tcttctctgt atc                                              23

<210> SEQ ID NO 139
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 139
```

```
accuuagaga ggaugguccu aucu                                      24

<210> SEQ ID NO 140
<211> LENGTH: 24
<212> TYPE: RNA
<213> ORGANISM: Artificial Sequence
<220> FEATURE:
<223> OTHER INFORMATION: Synthetic oigonucleotide

<400> SEQUENCE: 140
uuucuagcca gaacugcacu cuua                                      24

<210> SEQ ID NO 141
<211> LENGTH: 23
<212> TYPE: RNA
<213> ORGANISM: Homo sapiens

<400> SEQUENCE: 141
uguaguguuu ccuacuuuau gga                                       23

<210> SEQ ID NO 142
<211> LENGTH: 20
<212> TYPE: RNA
<213> ORGANISM: Homo sapiens

<400> SEQUENCE: 142
agcuacaucu ggcuacuggu                                           20

<210> SEQ ID NO 143
<211> LENGTH: 22
<212> TYPE: RNA
<213> ORGANISM: Homo sapiens

<400> SEQUENCE: 143
ucugguccgu gucuucacuc cc                                        22

<210> SEQ ID NO 144
<211> LENGTH: 22
<212> TYPE: RNA
<213> ORGANISM: Homo sapiens

<400> SEQUENCE: 144
gauuagggug cuuagcuguu aa                                        22

<210> SEQ ID NO 145
<211> LENGTH: 23
<212> TYPE: RNA
<213> ORGANISM: Homo sapiens

<400> SEQUENCE: 145
aacauucauu gcugucggug ggu                                       23

<210> SEQ ID NO 146
<211> LENGTH: 21
<212> TYPE: RNA
<213> ORGANISM: Homo sapiens

<400> SEQUENCE: 146
auauaugaug acuuagcuuu u                                         21

<210> SEQ ID NO 147
<211> LENGTH: 21
<212> TYPE: RNA
```

<213> ORGANISM: Homo sapiens

<400> SEQUENCE: 147
gguuuggucc uagccuuucu a                                                    21

<210> SEQ ID NO 148
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 148
gattggagaa gacgttgccc caattgaaca c                                         31

<210> SEQ ID NO 149
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 149
agcttgatga gatcggtgaa gacgttgcc                                            29

<210> SEQ ID NO 150
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 150
ggaaggtctg caggacactg ttagcaaagt                                           30

<210> SEQ ID NO 151
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 151
gaaagttcca ttggcaaggt atgtaggaca ct                                        32

<210> SEQ ID NO 152
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 152
ccttacacat gcattgtcat agttgtggca g                                         31

<210> SEQ ID NO 153
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 153
actccttcct gactcatgca ctgtcatagt t                                         31

```
<210> SEQ ID NO 154
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 154
gtacgacaat taaagtcgac taccctttgtt tctac                           35

<210> SEQ ID NO 155
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 155
cgtcgacctc tcggacgaaa agg                                         23

<210> SEQ ID NO 156
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 156
ctcgagtaga aacaagggta tttttcttta attg                             34

<210> SEQ ID NO 157
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 157
gtcgacctct tccaggacat actgctg                                     27

<210> SEQ ID NO 158
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 158
ctcgagagaa acaagggtgt tttttatta                                   29

<210> SEQ ID NO 159
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 159
tccataaagt aggaaacact aca                                         23

<210> SEQ ID NO 160
<211> LENGTH: 22
<212> TYPE: DNA
<213> ORGANISM: Artificial Sequence
<220> FEATURE:
<223> OTHER INFORMATION: Synthetic oligonucleotide
```

<400> SEQUENCE: 160
gatcggtagc tacgtagcta gc                                          22

<210> SEQ ID NO 161
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 161
ccagtgctgt tagtagtgct ttc                                         23

<210> SEQ ID NO 162
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 162
gtctctacct gagtgtctct gaaac                                       25

<210> SEQ ID NO 163
<211> LENGTH: 318
<212> TYPE: DNA
<213> ORGANISM: Homo sapiens

<400> SEQUENCE: 163
ccagtgctgt tagtagtgct ttctacttta tgggtgactg cactgtctgt ctgtccgtcg    60
gcgtgtactc ttcaggctgc ccaggcctcc tgactcctgc tccaagagcc cccagccct   120 ccttgtggct tcctaagatc cccccaaccc tgccagggcc cccgagggc cgccctggg    180 ccttgtgggc ggtgactcag catggcgcca gacttgcctc ctctacctcc ctcccccact   240
tcctcttcag ttccctcttc ccttccccct aaaggctcca cccatccccc cagtttcag    300 agacactcag gtagagac                                                 318

<210> SEQ ID NO 164
<211> LENGTH: 24
<212> TYPE: RNA
<213> ORGANISM: Influenza virus

<400> SEQUENCE: 164
acaauagaga gaauggua cu cucu                                       24

<210> SEQ ID NO 165
<211> LENGTH: 24
<212> TYPE: RNA
<213> ORGANISM: Influenza virus

<400> SEQUENCE: 165
uuucuggcac ggucugcacu caua                                        24

<210> SEQ ID NO 166
<211> LENGTH: 24
<212> TYPE: RNA
<213> ORGANISM: Influenza virus

<400> SEQUENCE: 166
uuucuggcac ggucugcacu cauc                                        24

<210> SEQ ID NO 167
<211> LENGTH: 24
<212> TYPE: RNA
<213> ORGANISM: Influenza virus

<400> SEQUENCE: 167
gaugagauug gagaagaugu ggcu 24

<210> SEQ ID NO 168
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 168
gaugagaucg gugaagacgu ugcc 24

<210> SEQ ID NO 169
<211> LENGTH: 24
<212> TYPE: RNA
<213> ORGANISM: Influenza virus

<400> SEQUENCE: 169
gggaaggucu gcaggacuuu auua 24

<210> SEQ ID NO 170
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 170
gggaagguau guaggacacu guua 24

<210> SEQ ID NO 171
<211> LENGTH: 24
<212> TYPE: RNA
<213> ORGANISM: Influenza virus

<400> SEQUENCE: 171
uccuuccuua cacaugcauu gagu 24

<210> SEQ ID NO 172
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 172
uccuuccuga cucaugcauu guca 24

<210> SEQ ID NO 173
<211> LENGTH: 15
<212> TYPE: RNA
<213> ORGANISM: Influenza virus

<400> SEQUENCE: 173
acggaacaaa gauga 15

<210> SEQ ID NO 174
<211> LENGTH: 24
<212> TYPE: RNA

```
<213> ORGANISM: influenza virus

<400> SEQUENCE: 174
acaauagaga gaaugguacu cucu                                    24

<210> SEQ ID NO 175
<211> LENGTH: 24
<212> TYPE: RNA
<213> ORGANISM: influenza virus

<400> SEQUENCE: 175
uuucuggcac ggucugcacu caua                                    24

<210> SEQ ID NO 176
<211> LENGTH: 24
<212> TYPE: RNA
<213> ORGANISM: influenza virus

<400> SEQUENCE: 176
uuucuggcac ggucugcacu cauc                                    24

<210> SEQ ID NO 177
<211> LENGTH: 24
<212> TYPE: RNA
<213> ORGANISM: influenza virus

<400> SEQUENCE: 177
uuucuagcca gaacugcacu cuua                                    24

<210> SEQ ID NO 178
<211> LENGTH: 24
<212> TYPE: RNA
<213> ORGANISM: influenza virus

<400> SEQUENCE: 178
uuccuugcac ggacagcacu uuua                                    24

<210> SEQ ID NO 179
<211> LENGTH: 24
<212> TYPE: RNA
<213> ORGANISM: Artificial Sequence
<220> FEATURE:
<223> OTHER INFORMATION: mammalian oligonucleotide

<400> SEQUENCE: 179
gaugagauug gagaagaugu ggcu                                    24

<210> SEQ ID NO 180
<211> LENGTH: 24
<212> TYPE: RNA
<213> ORGANISM: influenza virus

<400> SEQUENCE: 180
gaugagaucg gugaagacgu ugcc                                    24

<210> SEQ ID NO 181
<211> LENGTH: 24
<212> TYPE: RNA
<213> ORGANISM: Artificial Sequence
<220> FEATURE:
<223> OTHER INFORMATION: mammalian oligonucleotide

<400> SEQUENCE: 181
gggaaggucu gcaggacuuu auua                                    24
```

```
<210> SEQ ID NO 182
<211> LENGTH: 24
<212> TYPE: RNA
<213> ORGANISM: influenza virus

<400> SEQUENCE: 182
gggaagguau guaggacacu guua                                              24

<210> SEQ ID NO 183
<211> LENGTH: 24
<212> TYPE: RNA
<213> ORGANISM: Artificial Sequence
<220> FEATURE:
<223> OTHER INFORMATION: mammalian oligonucleotide

<400> SEQUENCE: 183
uccuuccuua cacaugcauu gagu                                              24

<210> SEQ ID NO 184
<211> LENGTH: 24
<212> TYPE: RNA
<213> ORGANISM: influenza virus

<400> SEQUENCE: 184
uccuuccuga cucaugcauu guca                                              24

<210> SEQ ID NO 185
<211> LENGTH: 6
<212> TYPE: RNA
<213> ORGANISM: influenza virus

<400> SEQUENCE: 185 uuuuuu                                                                   6

<210> SEQ ID NO 186
<211> LENGTH: 15
<212> TYPE: RNA
<213> ORGANISM: influenza virus

<400> SEQUENCE: 186
acggaacaaa gauga                                                        15
```